United States Patent
Koser et al.

(10) Patent No.: US 11,052,105 B2
(45) Date of Patent: *Jul. 6, 2021

(54) METHODS FOR TREATING HEPATITIS B INFECTION

(71) Applicant: Dicerna Pharmaceuticals, Inc., Lexington, MA (US)

(72) Inventors: Martin Koser, Lexington, MA (US); Marc Abrams, Lexington, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/922,033

(22) Filed: Jul. 7, 2020

(65) Prior Publication Data

US 2020/0338109 A1 Oct. 29, 2020

Related U.S. Application Data

(63) Continuation of application No. 16/790,986, filed on Feb. 14, 2020, now Pat. No. 10,799,524, which is a continuation of application No. PCT/US2018/056801, filed on Oct. 19, 2018.

(60) Provisional application No. 62/575,358, filed on Oct. 20, 2017.

(51) Int. Cl.
*A61K 31/713* (2006.01)
*A61K 47/02* (2006.01)
*C12N 15/113* (2010.01)
*A61K 9/00* (2006.01)

(52) U.S. Cl.
CPC ............ *A61K 31/713* (2013.01); *A61K 47/02* (2013.01); *C12N 15/113* (2013.01); *A61K 9/0019* (2013.01); *C12N 2310/315* (2013.01); *C12N 2310/321* (2013.01); *C12N 2310/322* (2013.01)

(58) Field of Classification Search
None
See application file for complete search history.

(56) References Cited

U.S. PATENT DOCUMENTS

| | | |
|---|---|---|
| 8,372,968 B2 | 2/2013 | Tuschl et al. |
| 8,513,207 B2 | 8/2013 | Brown |
| 8,809,293 B2 | 8/2014 | Chin et al. |
| 8,883,996 B2 | 11/2014 | Rossi et al. |
| 8,927,513 B2 | 1/2015 | Manoharan et al. |
| 8,927,705 B2 | 1/2015 | Brown |
| 9,012,138 B2 | 4/2015 | Tuschl et al. |
| 9,012,621 B2 | 4/2015 | Tuschl et al. |
| 9,193,753 B2 | 11/2015 | Tuschl et al. |
| 9,567,587 B2 | 2/2017 | Freier et al. |
| 2004/0127446 A1 | 7/2004 | Blatt et al. |
| 2007/0254362 A1 | 11/2007 | Quay et al. |
| 2008/0274462 A1 | 11/2008 | Jeon et al. |
| 2009/0099115 A1 | 4/2009 | McSwiggen et al. |
| 2010/0184840 A1 | 7/2010 | Arbuthnot et al. |
| 2010/0323001 A1 | 12/2010 | Pachuk |
| 2011/0294869 A1 | 12/2011 | Petersen |
| 2016/0369279 A1 | 12/2016 | Bartz et al. |
| 2020/0171069 A1 | 6/2020 | Koser et al. |

FOREIGN PATENT DOCUMENTS

| | | |
|---|---|---|
| CN | 104059916 A | 9/2014 |
| WO | 2004045543 A2 | 6/2004 |
| WO | 2004078181 A1 | 9/2004 |
| WO | 2008016391 A2 | 2/2008 |
| WO | 2010033225 A2 | 3/2010 |
| WO | 2011133871 A2 | 10/2011 |
| WO | 2012145697 A1 | 10/2012 |
| WO | 2014088920 A1 | 6/2014 |
| WO | 2014094645 A1 | 6/2014 |
| WO | 2015188197 A2 | 12/2015 |
| WO | 2016077321 A1 | 5/2016 |
| WO | 2016100401 A1 | 6/2016 |
| WO | 2016183009 A2 | 11/2016 |
| WO | 2017027350 A2 | 2/2017 |
| WO | 2018027106 A2 | 2/2018 |

OTHER PUBLICATIONS

Abe et al. "Dumbbell-shaped nanocircular RNAs for RNA interference," J Am Chem Soc. 2007; 129(49): 15108-15109.
Antao et al., "A thermodynamic study of unusually stable RNA and DNA hairpins," Nucleic Acids Res. 1991; 19(21) 5901-5905.
Bennett et al. "Pharmacology of Antisense Drugs," Annual Review of Pharmacology and Toxicology. 2017; 57: 81-105.
Bramsen et al., "A large-scale chemical modification screen identifies design rules to generate siRNAs with high activity, high stability and low toxicity," Nucleic Acids Res. 2009; 37(9): 2867-2881.
Bramsen et al., "Development of Therapeutic-Grade Small Interfering RNAs by Chemical Engineering," Frontiers in Genetics. 2012; 3(154): 1-22.
Bramsen et al., "Improved silencing properties using small internally segmented interfering RNAs," Nucleic Acids Res. 2007; 35(17): 5886-5897.
Chang et al., "Asymmetric shorter-duplex siRNA structures trigger efficient gene silencing with reduced nonspecific effects," Mol Ther. 2009; 17(4): 725-732.
Cheong et al., "Solution structure of an unusually stable RNA hairpin, 5'GGAC(UUCG)GUCC," Nature. 1990; 346(6285): 680-682.
Cornish-Bowden, "Nomenclature for incompletely specified bases in nucleic acid sequences: recommendations 1984," Nucl. Acids Res. 1985; 13(9): 3021-3030.
Dellinger et al., "Solid-phase chemical synthesis of phosphonoacetate and thiophosphonoacetate oligodeoxynucleotides," J. Am. Chem. Soc. 2003; 125(4): 940-950.
Elsner, "Single-stranded siRNAs for in vivo gene silencing," Nature Biotechnology. 2012; 30(11): 1063.

(Continued)

*Primary Examiner* — Tracy Vivlemore

(74) *Attorney, Agent, or Firm* — Byron V. Olsen; Dechert LLP; Andrea L. C. Reid

(57) ABSTRACT

This application relates to potent oligonucleotides useful for reducing HBsAg expression and treating HBV infections.

27 Claims, 27 Drawing Sheets

Specification includes a Sequence Listing.

(56) References Cited

OTHER PUBLICATIONS

Hamilton et al., "Two classes of short interfering RNA in RNA silencing," EMBO J. 2002; 21(17): 4671-4679.
Heermann et al., "Large surface proteins of hepatitis B virus containing the pre-s sequence," J Virol. 1984; 52(2): 396-402.
Heus et al., "Structural features that give rise to the unusual stability of RNA hairpins containing GNRA loops," Science. 1991; 253(5016): 191-194.
Hohjoh, "Enhancement of RNAi activity by improved siRNA duplexes," FEBS Letters. 2004; 557(1-3): 193-198.
Huang et al. "LncRNA NR2F1-AS1 regulates hepatocellular carcinoma oxaliplatin resistance by targeting ABCC1 via miR-363," J. Cell. Mol. Med. 2018; 22(6): 3238-3245.
Huch et al., "In vitro expansion of single Lgr5+ liver stem cells induced by Wnt-driven regeneration," Nature. 2013; 494(7436): 247-250.
Imanishi et al., "BNAs: novel nucleic acid analogs with a bridged sugar moiety," The Royal Society of Chemistry, Chem. Commun. 2002; 16: 1653-1659.
International Search Report and Written Opinion issued by the United States Patent Office as International Searching Authority for International Application No. PCT/US2018/056801, dated Apr. 15, 2019 (19 pages).
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron. 1998; 54(14): 3607-3630.
Loakes et al., "3-Nitropyrrole and 5-nitroindole as universal bases in primers for DNA sequencing and PCR," Nucleic Acids Res. 1995; 23(13): 2361-2366.
Loakes et al., "5-Nitroindole as an universal base analogue," Nucleic Acids Res. 1994; 22(20): 4039-4043.
Matsui et al., "Argonaute 2-dependent Regulation of Gene Expression by Single-stranded miRNA Mimics," Molecular Therapy. 2016; 24(5): 946-955.
Meade et al., "Efficient delivery of RNAi prodrugs containing reversible charge-neutralizing phosphotriester backbone modifications," Nature Biotechnology. 2014; 32(12): 1256-1261.
Moore et al., "Short hairpin RNA (shRNA): design, delivery, and assessment of gene knockdown," Methods Mol. Biol. 2010; 629: 141-158.
Nakano et al., "Selection for thermodynamically stable DNA tetraloops using temperature gradient gel electrophoresis reveals four motifs: d(cGNNAg), d(cGNABg),d(cCNNGg), and d(gCNNGc)," Biochemistry. 2002; 41(48): 14281-14292.
Prakash et al., "Identification of metabolically stable 5'-phosphate analogs that support single-stranded siRNA activity," Nucleic Acids Res. 2015; 43(6): 2993-3011.
Snead et al., "5' Unlocked Nucleic Acid Modification Improves siRNA Targeting," Mol Ther Nucleic Acids. 2013; 2: e103.
Sun et al., "Asymmetric RNA duplexes mediate RNA interference in mammalian cells," Nat. Biotechnol. 2008; 26(12): 1379-1382.
Van Aerschot et al., "An acyclic 5-nitroindazole nucleoside analogue as ambiguous nucleoside," Nucleic Acids Res. 1995; 23(21): 4363-4370.
Woese et al., "Architecture of ribosomal RNA: constraints on the sequence of "tetra-loops"," Proc Natl Acad Sci USA. 1990; 87(21): 8467-8471.
Huang, "Preclinical and Clinical Advances of GalNAc-Decorated Nucleic Acid Therapeutics," Mol Ther Nucleic Acids. 2017; 6:116-132.
Koser et al., "GalXC™ RNAi Platform Enables Potent and Durable RNAi-Mediated Inhibition of Hepatitis B Virus in Preclinical Models: How GalXC Delivers RNAi Conjugates to the Liver," Apr. 14, 2018; Retrieved from the Internet: https://dicerna.gcs-web.com/static-files/2bcfb940-4095-4ce5-8adb-5fb9fa6f1281 and Koser et al., "SAT-384-GalXC technology enables potent and durable RNAi-mediated inhibition of hepatitis B virus in preclinical models," Journal of Hepatology. 2018; 68(1): S781.

FIG. 7

Dose by Cohort

| Group A Cohort | Dose |
|---|---|
| A1 | 0.1 mg/kg |
| A2 | 1.5 mg/kg |
| A3 | 3.0 mg/kg |
| A4 | 6.0 mg/kg |
| A5 | 12.0 mg/kg |

| Group B Cohort | Dose |
|---|---|
| B1 | 3.0 mg/kg |

| Group C Cohort | Dose |
|---|---|
| C1 | 1.5 mg/kg x 4 |
| C2 | 3.0 mg/kg x 4 |
| C3 | 6.0 mg/kg x 4 |

FIG. 18

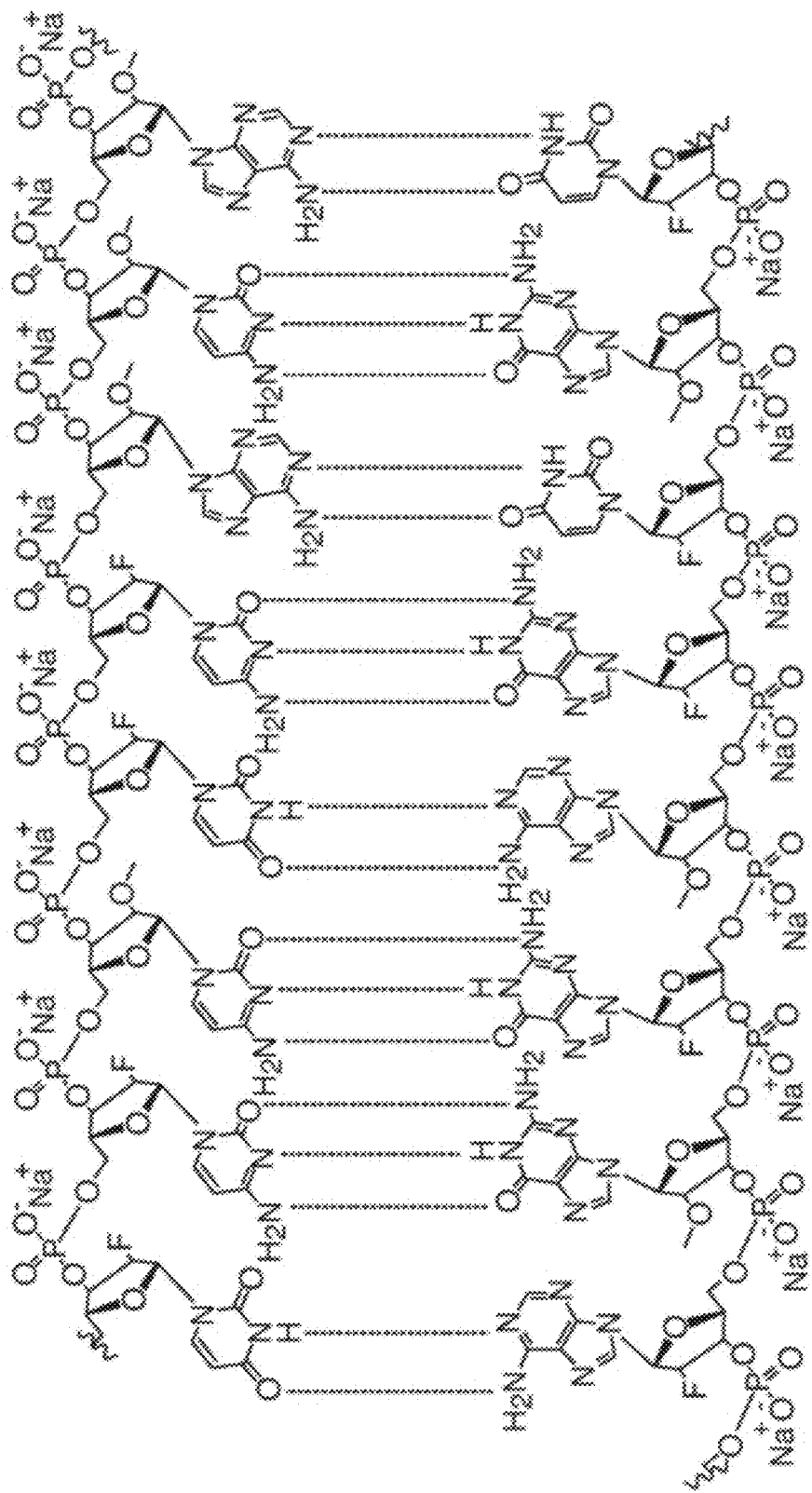
FIG. 19A - cont.

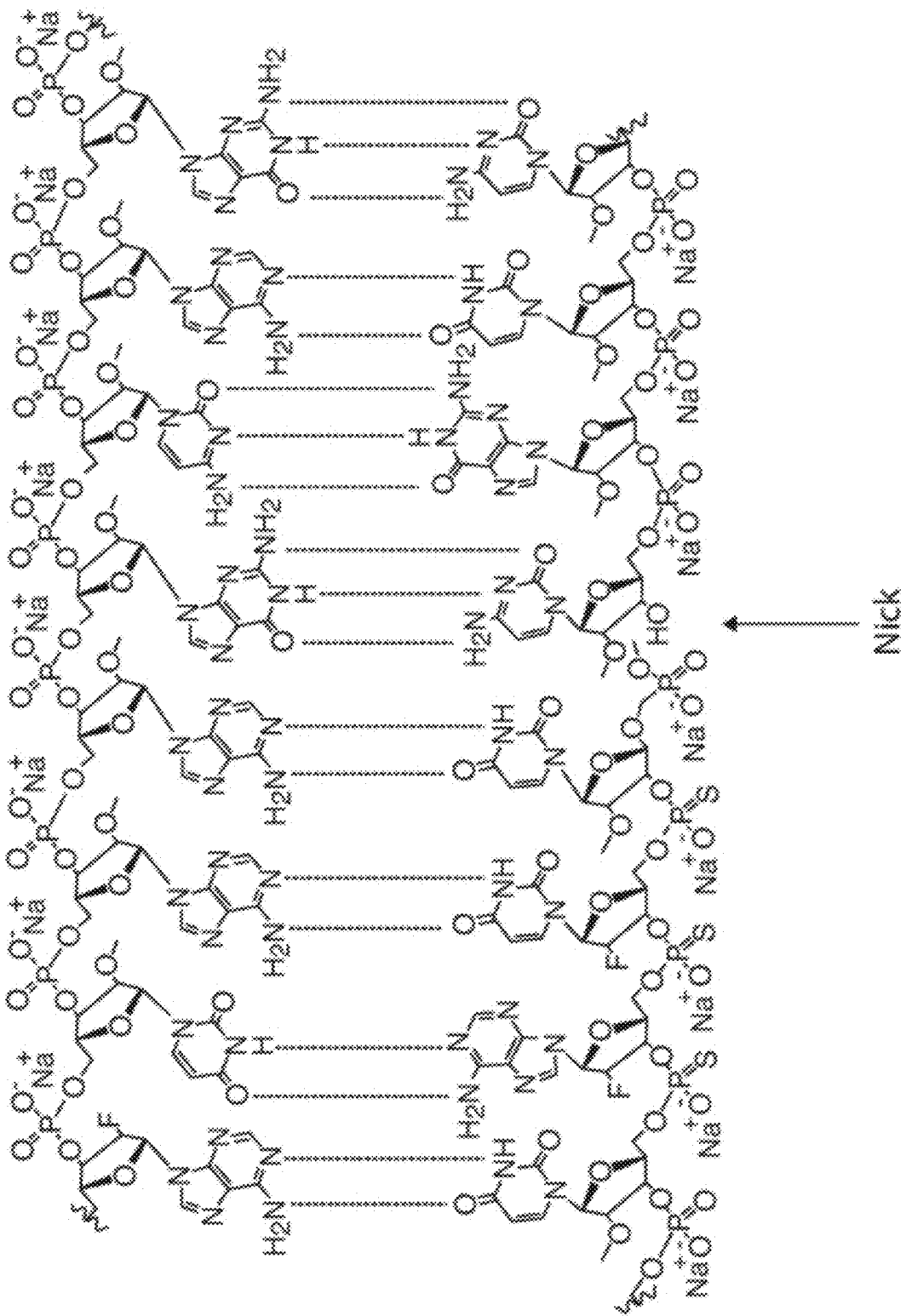
FIG. 19A - cont.

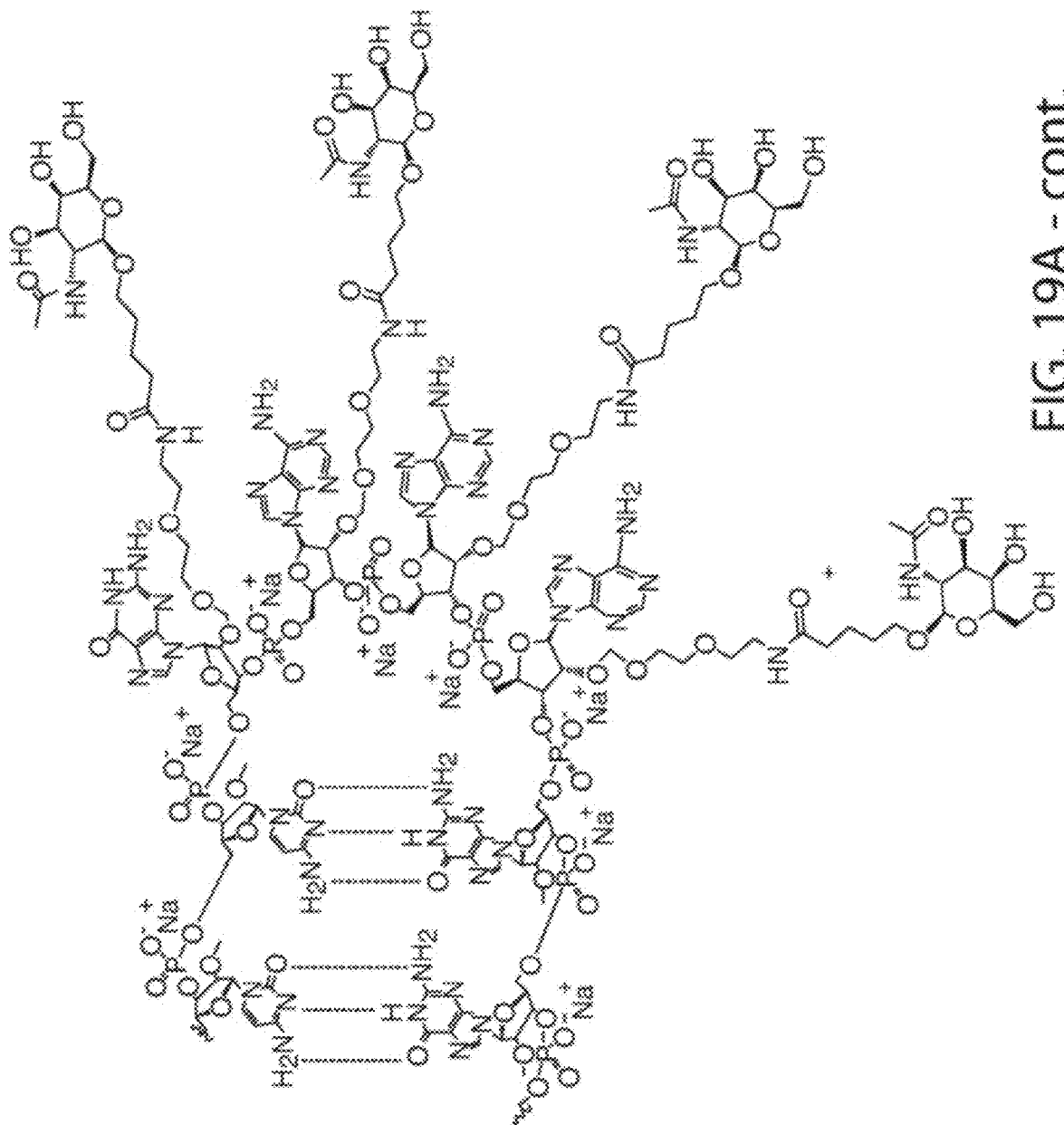
FIG. 19A - cont.

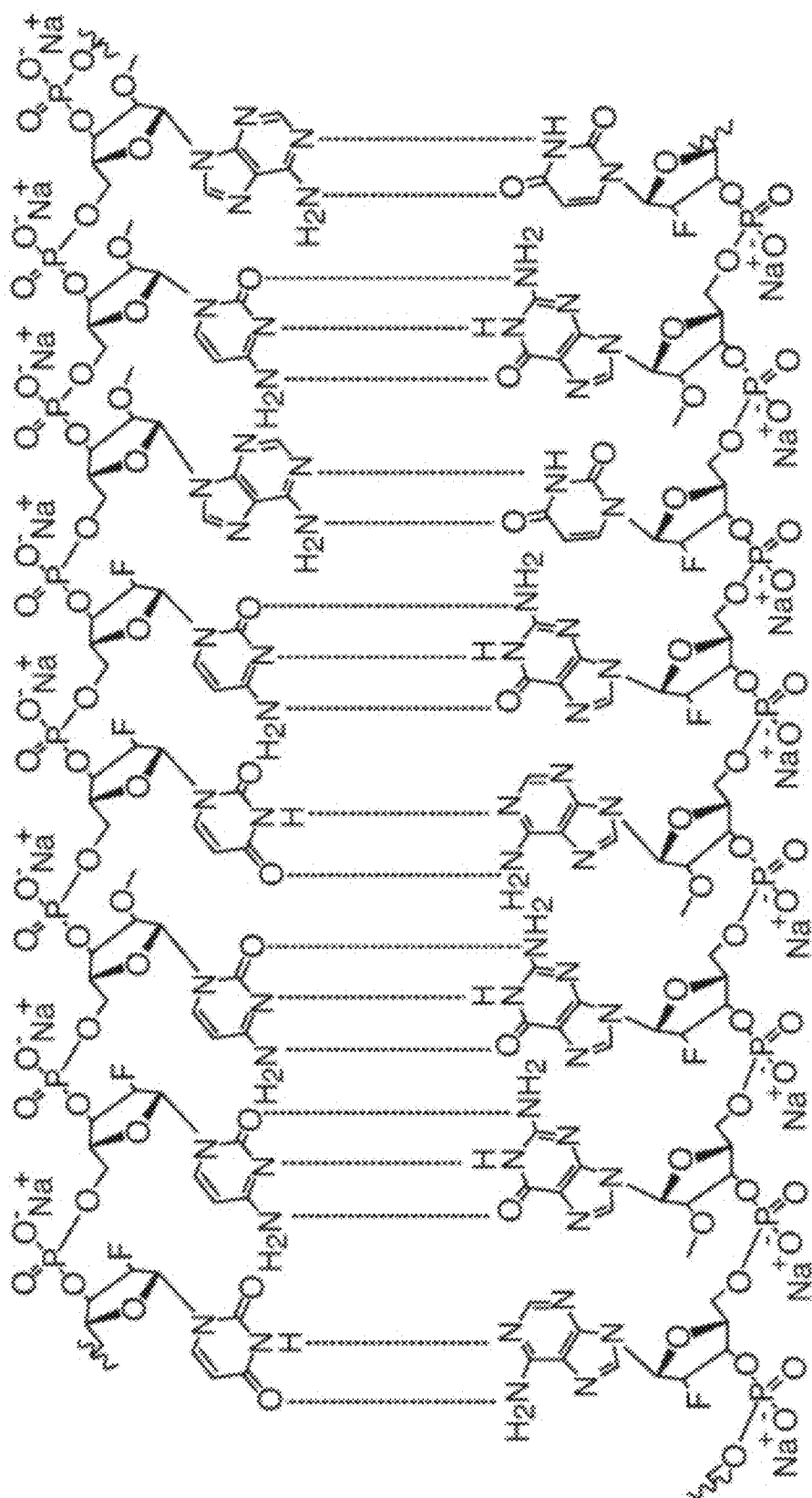
FIG. 19B - cont.

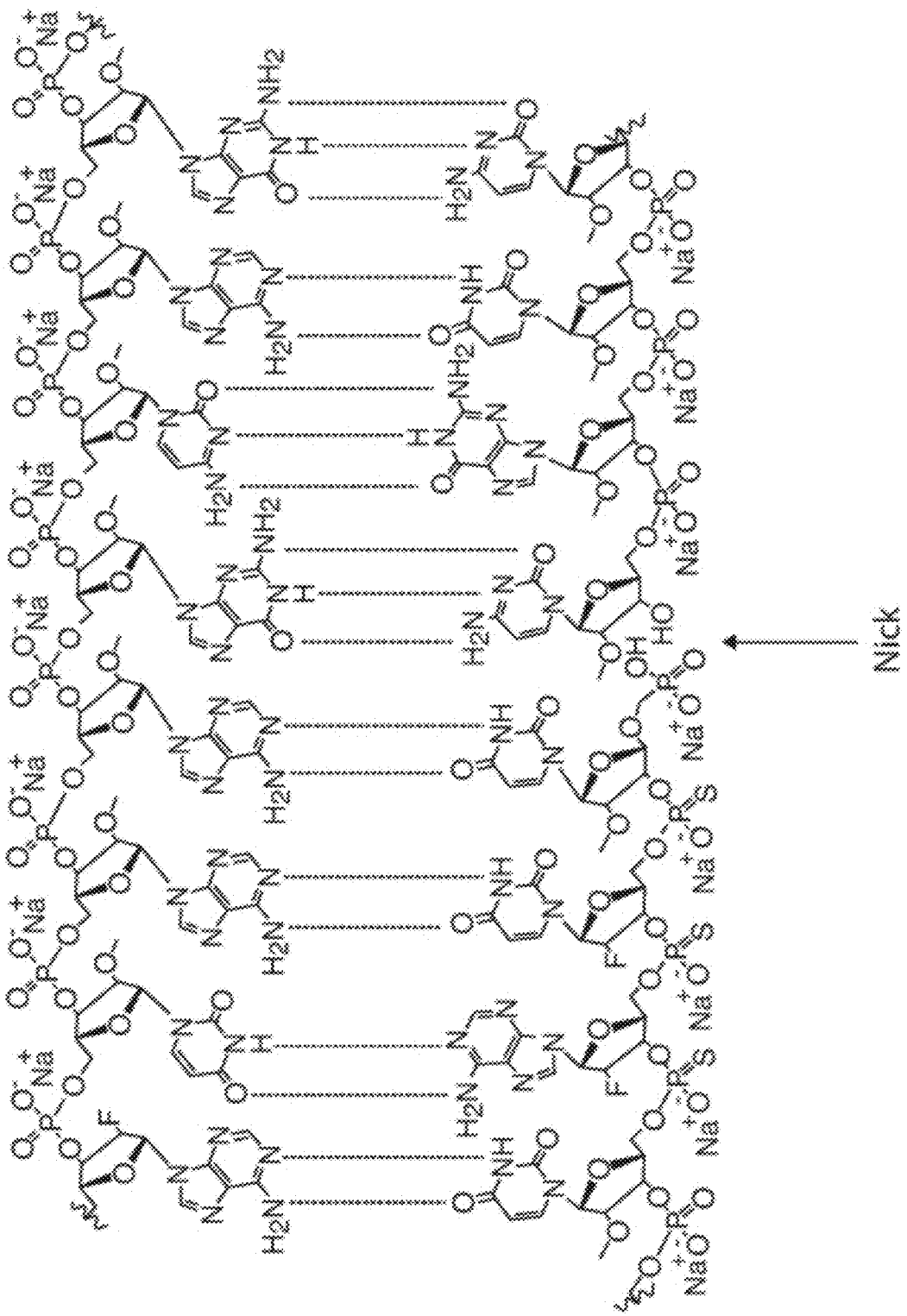
FIG. 19B - cont.

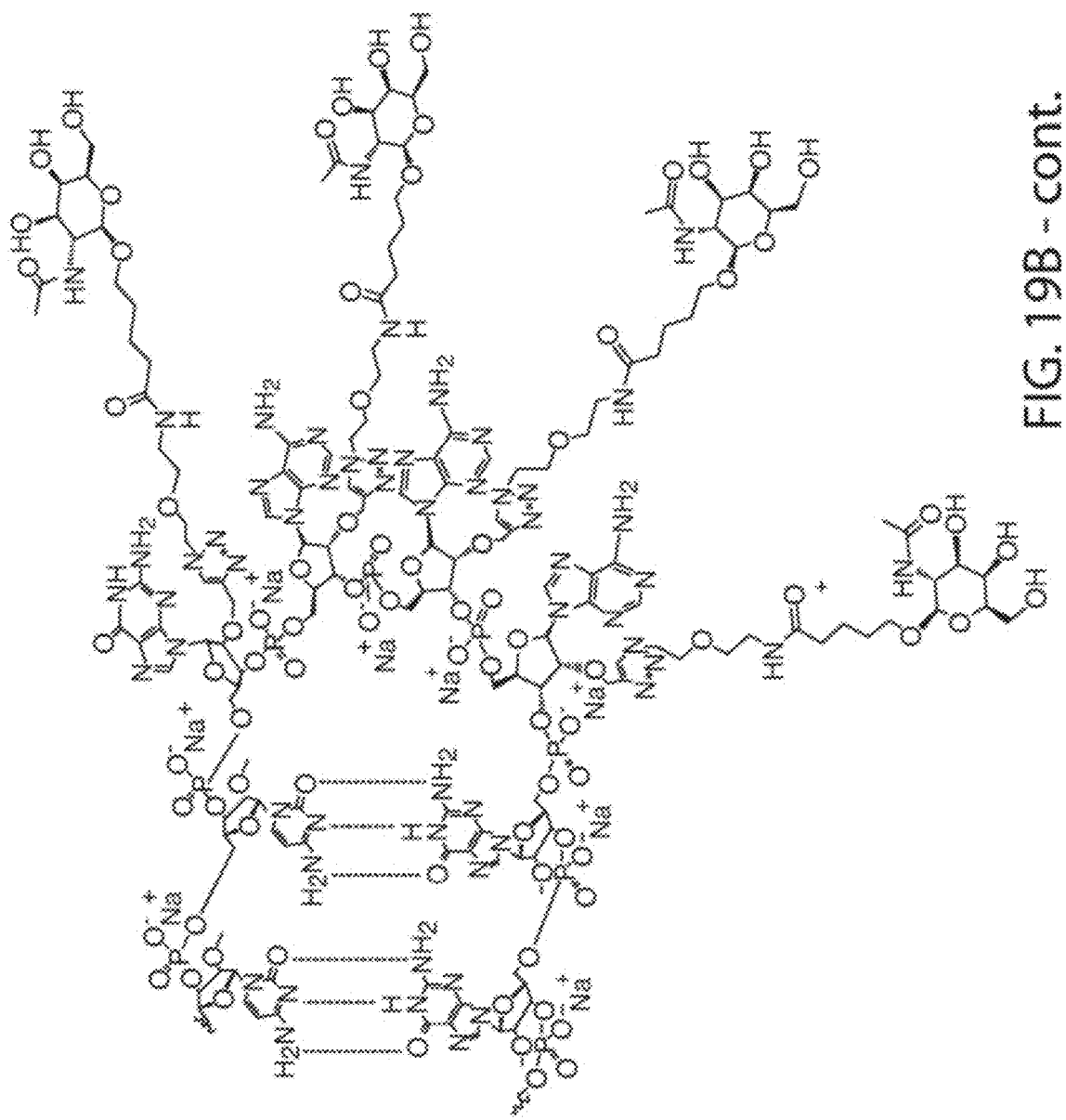
FIG. 19B - cont.

|  | HBV-219 | HBV-254 | HBV-258 |
|---|---|---|---|
| ORF Target | S | S | S |
| Sense 19-mer | GACAAGAATCCTCACAATA (SEQ ID NO: 29) | CGTGGTGGACTTCTCTCAA (SEQ ID NO: 30) | GTGGACTTCTCTCAATTTT (SEQ ID NO: 31) |
| Sense 19-mer w/ambiguous Base | GACAANAATCCTCACAATA (SEQ ID NO: 32) | CGTGGTGGACTTCTCTCAN (SEQ ID NO: 33) | GTGGACTTCTCTCANTTT (SEQ ID NO: 34) |
| Guide Position of Mismatch | 15 | 2 | 6 |
| Genotype A | 97/99 [3278] | 94/97 [4002] | 94/97 [4005] |
| Genotype B | 03/95 [2563] | 81/97 [2700] | 82/99 [2700] |
| Genotype C | 92/97 [4783] | 95/97 [4938] | 96/98 [4938] |
| Genotype D | 95/97 [4311] | 96/99 [4395] | 96/98 [4398] |
| Genotype E | 01/98 [1039] | 93/95 [1234] | 93/95 [1232] |
| Genotype F | 01/90 [425] | 94/96 [501] | 95/96 [501] |
| Genotype G | 92/99 [83] | 98/98 [85] | 99/99 [85] |
| Genotype H | 03/92 [71] | 86/97 [78] | 87/99 [78] |
| Genotype I | 00/100 [18] | 95/100 [22] | 95/100 [22] |
| TOTAL (focused analysis) | 72/97 [17021] | 93/97 [17995] | 93/98 [17959] |
| TOTAL (initial analysis) | 66/96 [5628] | 94/98 [5628] | 94/98 [5628] |

*Percent conservation reported as (*perfect/MM*), with values <90% shown in bold; [Total N#]

FIG. 20

SEQUENCE LISTING

<160> NUMBER OF SEQ ID NOS: 65

<210> SEQ ID NO 1
<211> LENGTH: 18
<212> TYPE: RNA
<213> ORGANISM: Artificial Sequence
<220> FEATURE:
<223> OTHER INFORMATION: Synthetic Polynucleotide

```
<220> FEATURE:
<221> NAME/KEY: misc_feature
<222> LOCATION: (5)..(5)
<223> OTHER INFORMATION: n is a, c, g, or u

<400> SEQUENCE: 1
acaanaaucc ucacaaua                                                 18

<210> SEQ ID NO 2
<211> LENGTH: 15
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 2
uunuugugag gauun                                                    15

<210> SEQ ID NO 3
<211> LENGTH: 20
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (15)..(15)
<223> OTHER INFORMATION: n is a, c, g, or u

<400> SEQUENCE: 3
uuauugugag gauunuuguc                                               20

<210> SEQ ID NO 4
<211> LENGTH: 22
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (15)..(15)
<223> OTHER INFORMATION: n is a, c, g, or u

<400> SEQUENCE: 4
uuauugugag gauunuuguc gg                                            22

<210> SEQ ID NO 5
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 5
uuauugugag gauucuuguc gg                                            22

<210> SEQ ID NO 6
<211> LENGTH: 22
<212> TYPE: RNA
<213> ORGANISM: Artificial Sequence
<220> FEATURE:
```

```
<223> OTHER INFORMATION: Synthetic Polynucleotide

<400> SEQUENCE: 6
uuauugugag gauuuuuguc gg                                              22

<210> SEQ ID NO 7
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is a, c, g, or u

<400> SEQUENCE: 7
acaanaaucc ucacaauaa                                                  19

<210> SEQ ID NO 8
<211> LENGTH: 36
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (6)..(6)
<223> OTHER INFORMATION: n is a, c, g, or u

<400> SEQUENCE: 8
gacaanaauc cucacaauaa gcagccgaaa ggcugc                               36

<210> SEQ ID NO 9
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 9
gacaaaaauc cucacaauaa gcagccgaaa ggcugc                               36

<210> SEQ ID NO 10
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 10
gacaagaauc cucacaauaa gcagccgaaa ggcugc                               36

<210> SEQ ID NO 11
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 11
aatcctcaca                                                            10

<210> SEQ ID NO 12
<211> LENGTH: 10
<212> TYPE: RNA
<213> ORGANISM: Artificial Sequence
```

```
<220> FEATURE:
<223> OTHER INFORMATION: Synthetic Polynucleotide

<400> SEQUENCE: 12
ugugaggauu                                                                  10

<210> SEQ ID NO 13
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 13
tgtgaggatt                                                                  10

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
tattgtgagg attcttgtca                                                       20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
cggtattgtg aggattcttg                                                       20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
tgtgaggatt cttgtcaaca                                                       20

<210> SEQ ID NO 17
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 17
uauugugagg auuuuuguca a                                                     21

<210> SEQ ID NO 18
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 18
ugcgguauug ugaggauuct t                                                     21
```

```
<210> SEQ ID NO 19
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 19
acagcattgt gaggattctt gtc                                              23

<210> SEQ ID NO 20
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 20
uauugugagg auuuuuguca aca                                              23

<210> SEQ ID NO 21
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 21
auugugagga uuuuugucaa caa                                              23

<210> SEQ ID NO 22
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 22
uugugaggau uuuugucaac aag                                              23

<210> SEQ ID NO 23
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 23 guggguggacu ucucucaaua gcagccgaaa ggcugc                               36

<210> SEQ ID NO 24
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 24
uauugagaga aguccaccac gg                                               22

<210> SEQ ID NO 25
<211> LENGTH: 22
<212> TYPE: RNA
<213> ORGANISM: Artificial Sequence
<220> FEATURE:
<223> OTHER INFORMATION: Synthetic Polynucleotide
```

```
<400> SEQUENCE: 25
uuugugagga uuuuugucaa gg                                          22

<210> SEQ ID NO 26
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 26
ucugagagaa guccaccacg gg                                          22

<210> SEQ ID NO 27
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 27
uacugagaga aguccaccac gg                                          22

<210> SEQ ID NO 28
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 28
uaaaacugag agaaguccac gg                                          22

<210> SEQ ID NO 29
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 29
gacaagaatc ctcacaata                                              19

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
cgtggtggac ttctctcaa                                              19

<210> SEQ ID NO 31
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 31
gtggacttct ctcaatttt                                              19

<210> SEQ ID NO 32
```

```
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (6)..(6)
<223> OTHER INFORMATION: n is a, c, g, or t

<400> SEQUENCE: 32
gacaanaatc ctcacaata                                                    19

<210> SEQ ID NO 33
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: n is a, c, g, or t

<400> SEQUENCE: 33
cgtggtggac ttctctcan                                                    19

<210> SEQ ID NO 34
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (15)..(15)
<223> OTHER INFORMATION: n is a, c, g, or t

<400> SEQUENCE: 34
gtggacttct ctcantttt                                                    19

<210> SEQ ID NO 35
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 35
tgttgacaag aatcctcaca at                                                22

<210> SEQ ID NO 36
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 36
tcgtggtgga cttctctcaa t                                                 21

<210> SEQ ID NO 37
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

```
<222> LOCATION: (10)..(10)
<223> OTHER INFORMATION: n is a, c, g, or t

<400> SEQUENCE: 37
tgttgacaan aatcctcaca at                                              22

<210> SEQ ID NO 38
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: n is a, c, g, or t

<400> SEQUENCE: 38
tcgtggtgga cttctctcan t                                               21

<210> SEQ ID NO 39
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 39
ugcacuucgc gucaccucua gcagccgaaa ggcugc                               36

<210> SEQ ID NO 40
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 40
uagaggugac gcgaagugca gg                                              22

<210> SEQ ID NO 41
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 41
gcaccucucu uuacgcggaa gcagccgaaa ggcugc                               36

<210> SEQ ID NO 42
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 42
uuccgcguaa agagaggugc gg                                              22

<210> SEQ ID NO 43
<211> LENGTH: 36
<212> TYPE: RNA
<213> ORGANISM: Artificial Sequence
<220> FEATURE:
<223> OTHER INFORMATION: Synthetic Polynucleotide
<220> FEATURE:
```

<220> FEATURE:
<221> NAME/KEY: misc_feature
<222> LOCATION: (1)..(1)
<223> OTHER INFORMATION: may be modified by 2'-O-methyl ribonucleotide
<220> FEATURE:
<221> NAME/KEY: misc_feature
<222> LOCATION: (1)..(2)
<223> OTHER INFORMATION: may be modified by phosphorothioate
<220> FEATURE:
<221> NAME/KEY: misc_feature
<222> LOCATION: (2)..(2)
<223> OTHER INFORMATION: may be modified by 2'-O-methyl ribonucleotide
<220> FEATURE:
<221> NAME/KEY: misc_feature
<222> LOCATION: (3)..(3)
<223> OTHER INFORMATION: may be modified by
    2'-fluoro-deoxyribonucleotide
<220> FEATURE:
<221> NAME/KEY: misc_feature
<222> LOCATION: (4)..(7)
<223> OTHER INFORMATION: may be modified by 2'-O-methyl ribonucleotide
<220> FEATURE:
<221> NAME/KEY: misc_feature
<222> LOCATION: (8)..(10)
<223> OTHER INFORMATION: may be modified by
    2'-fluoro-deoxyribonucleotide
<220> FEATURE:
<221> NAME/KEY: misc_feature
<222> LOCATION: (11)..(11)
<223> OTHER INFORMATION: may be modified by 2'-O-methyl ribonucleotide
<220> FEATURE:
<221> NAME/KEY: misc_feature
<222> LOCATION: (12)..(13)
<223> OTHER INFORMATION: may be modified by
    2'-fluoro-deoxyribonucleotide
<220> FEATURE:
<221> NAME/KEY: misc_feature
<222> LOCATION: (14)..(16)
<223> OTHER INFORMATION: may be modified by 2'-O-methyl ribonucleotide
<220> FEATURE:
<221> NAME/KEY: misc_feature
<222> LOCATION: (17)..(17)
<223> OTHER INFORMATION: may be modified by
    2'-fluoro-deoxyribonucleotide
<220> FEATURE:
<221> NAME/KEY: misc_feature
<222> LOCATION: (18)..(26)
<223> OTHER INFORMATION: may be modified by 2'-O-methyl ribonucleotide
<220> FEATURE:
<221> NAME/KEY: misc_feature
<222> LOCATION: (27)..(27)
<223> OTHER INFORMATION: may be modified by 2'-modified-GalNAc guanosine
<220> FEATURE:
<221> NAME/KEY: misc_feature
<222> LOCATION: (28)..(30)
<223> OTHER INFORMATION: may be modified by 2'-modified-GalNAc adenosine
<220> FEATURE:
<221> NAME/KEY: misc_feature
<222> LOCATION: (31)..(36)
<223> OTHER INFORMATION: may be modified by 2'-O-methyl ribonucleotide

<400> SEQUENCE: 43
gacaaaaauc cucacaauaa gcagccgaaa ggcugc                    36

<210> SEQ ID NO 44
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: may be modified by
    4'-O-monomethylphosphonate-2'-O-methyl uridine
<220> FEATURE:
<221> NAME/KEY: misc_feature
<222> LOCATION: (1)..(4)

```
<223> OTHER INFORMATION: may be modified by phosphorothioate
<220> FEATURE:
<221> NAME/KEY: misc_feature
<222> LOCATION: (2)..(3)
<223> OTHER INFORMATION: may be modified by
      2'-fluoro-deoxyribonucleotide
<220> FEATURE:
<221> NAME/KEY: misc_feature
<222> LOCATION: (4)..(4)
<223> OTHER INFORMATION: may be modified by 2'-O-methyl ribonucleotide
<220> FEATURE:
<221> NAME/KEY: misc_feature
<222> LOCATION: (5)..(5)
<223> OTHER INFORMATION: may be modified by
      2'-fluoro-deoxyribonucleotide
<220> FEATURE:
<221> NAME/KEY: misc_feature
<222> LOCATION: (6)..(6)
<223> OTHER INFORMATION: may be modified by 2'-O-methyl ribonucleotide
<220> FEATURE:
<221> NAME/KEY: misc_feature
<222> LOCATION: (7)..(8)
<223> OTHER INFORMATION: may be modified by
      2'-fluoro-deoxyribonucleotide
<220> FEATURE:
<221> NAME/KEY: misc_feature
<222> LOCATION: (9)..(9)
<223> OTHER INFORMATION: may be modified by 2'-O-methyl ribonucleotide
<220> FEATURE:
<221> NAME/KEY: misc_feature
<222> LOCATION: (10)..(10)
<223> OTHER INFORMATION: may be modified by
      2'-fluoro-deoxyribonucleotide
<220> FEATURE:
<221> NAME/KEY: misc_feature
<222> LOCATION: (11)..(11)
<223> OTHER INFORMATION: may be modified by 2'-O-methyl ribonucleotide
<220> FEATURE:
<221> NAME/KEY: misc_feature
<222> LOCATION: (12)..(12)
<223> OTHER INFORMATION: may be modified by
      2'-fluoro-deoxyribonucleotide
<220> FEATURE:
<221> NAME/KEY: misc_feature
<222> LOCATION: (13)..(13)
<223> OTHER INFORMATION: may be modified by 2'-O-methyl ribonucleotide
<220> FEATURE:
<221> NAME/KEY: misc_feature
<222> LOCATION: (14)..(14)
<223> OTHER INFORMATION: may be modified by
      2'-fluoro-deoxyribonucleotide
<220> FEATURE:
<221> NAME/KEY: misc_feature
<222> LOCATION: (15)..(15)
<223> OTHER INFORMATION: may be modified by 2'-O-methyl ribonucleotide
<220> FEATURE:
<221> NAME/KEY: misc_feature
<222> LOCATION: (16)..(16)
<223> OTHER INFORMATION: may be modified by
      2'-fluoro-deoxyribonucleotide
<220> FEATURE:
<221> NAME/KEY: misc_feature
<222> LOCATION: (17)..(18)
<223> OTHER INFORMATION: may be modified by 2'-O-methyl ribonucleotide
<220> FEATURE:
<221> NAME/KEY: misc_feature
<222> LOCATION: (19)..(19)
<223> OTHER INFORMATION: may be modified by
      2'-fluoro-deoxyribonucleotide
<220> FEATURE:
<221> NAME/KEY: misc_feature
<222> LOCATION: (20)..(22)
<223> OTHER INFORMATION: may be modified by 2'-O-methyl ribonucleotide
<220> FEATURE:
<221> NAME/KEY: misc_feature
<222> LOCATION: (20)..(22)
<223> OTHER INFORMATION: may be modified by phosphorothioate

<400> SEQUENCE: 44
```
uuauugugag gauuuuuugu cgg 23

<210> SEQ ID NO 45
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 45
tgttgacaag aatcctcaca atacctcgtg gtggacttct ctcaattttc 50

<210> SEQ ID NO 46
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 46
ggaacuguuu uuaggagugu uu 22

<210> SEQ ID NO 47
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 47
ggaacuguuc uuaggagugu uu 22

<210> SEQ ID NO 48
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 48
ggcuguuuuu aggaguguua uu 22

<210> SEQ ID NO 49
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 49
ggcuguucuu aggaguguua uu 22

<210> SEQ ID NO 50
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 50
ttgacaagaa tcctcacaat ac 22

<210> SEQ ID NO 51
<211> LENGTH: 22
<212> TYPE: RNA

<213> ORGANISM: Artificial Sequence
<220> FEATURE:
<223> OTHER INFORMATION: Synthetic Polynucleotide

<400> SEQUENCE: 51
gggcaccacc ugaagagagu cu                                          22

<210> SEQ ID NO 52
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 52
gggcaccacc ugaagagagu uu                                          22

<210> SEQ ID NO 53
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 53
ctcgtggtgg acttctctca at                                          22

<210> SEQ ID NO 54
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 54
ggcaccaccu gaagagaguc au                                          22

<210> SEQ ID NO 55
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 55
ggcaccaccu gaagagaguu au                                          22

<210> SEQ ID NO 56
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 56
tcgtggtgga cttctctcaa tt                                          22

```
<210> SEQ ID NO 57
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 57
ggcaccugaa gagagucaaa au                                              22

<210> SEQ ID NO 58
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 58
ggcaccugaa gagaguuaaa au                                              22

<210> SEQ ID NO 59
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 59
tggtggactt ctctcaattt tc                                              22

<210> SEQ ID NO 60
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 60
uuugugagga uucuugucaa gg                                              22

<210> SEQ ID NO 61
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 61
uuugagagaa guccaccacg gg                                              22

<210> SEQ ID NO 62
<211> LENGTH: 22
<212> TYPE: RNA
<213> ORGANISM: Artificial Sequence
<220> FEATURE:
<223> OTHER INFORMATION: Synthetic Polynucleotide
```

```
<400> SEQUENCE: 62
uauugagaga aguccaccac gg                                            22

<210> SEQ ID NO 63
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 63
uaaaauugag agaaguccac gg                                            22

<210> SEQ ID NO 64
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 64
tgttgacaag aatcctcaca atac                                          24

<210> SEQ ID NO 65
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 65
ctcgtggtgg acttctctca attttc                                        26
```

METHODS FOR TREATING HEPATITIS B INFECTION

REFERENCE TO SEQUENCE LISTING

A Sequence Listing is being submitted electronically via EFS in the form of a text file created Jan. 26, 2021 and named "400930 009USC2 174427 SL.txt" (17,465 bytes), the content of which is incorporated herein by reference in its entirety.

FIELD OF THE INVENTION

The present application relates to oligonucleotides and uses thereof, particularly uses relating to the treatment of hepatitis B infection.

BACKGROUND OF THE INVENTION

Chronic Hepatitis B Virus (HBV) infection is a significant cause of worldwide morbidity and mortality. Current HBV therapies, such as nucleoside analogs require lifelong therapy to reduce plasma viremia, and they are generally ineffective in the long term. Functional cure of chronic HBV has traditionally been a best treatment outcome. RNA interference (RNAi) technology offers the potential for pharmacologically intervention.

The outer envelope proteins are collectively known as hepatitis B surface antigen (HBsAg). HBsAg consists of three related polypeptides called S, M, and L encoded by overlapping open reading frames (ORF). The smallest envelope protein is S with 226 amino acids, called the S-ORF. M and L are produced from upstream translation initiation sites and add 55 and 108 amino acids, repectively, to S. HBV S, M, and L glycoproteins are found in the viral envelope of intact, infectious HBV virions, named Dane particles, and all three are produced and secreted in a vast excess that forms non-infectious subviral spherical and filamentous particles (both referred to as decoy particles) found in the blood of chronic HBV patients. The abundance of HBsAg on the surface of decoy particles is believed to inhibit humoral immunity and spontaneous clearance in patients with chronic HBV infection (CHB).

BRIEF SUMMARY OF THE INVENTION

Aspects of the disclosure relate to improved oligonucleotide-based compositions and related methods for treating HBV infection in a subject. In some embodiments, the disclosure relates to the development of potent oligonucleotides that produce durable knockdown of HBV surface antigen (HBsAg) expression. The oligonucleotide induce RNA interference (RNAi)-mediated recognition and destruction of mRNA which encodes all forms of HBsAg in hepatocytes. This includes protein translated from viral RNAs transcribed from both cccDNA and HBV DNA which has been integrated into the host genome. Oligonucleotides are provided herein designed to target an expansive set of HBsAg transcripts encoded by HBV genomes across all known genotypes. In some embodiments, it has been found that oligonucleotides disclosed herein that target HBsAg transcripts in hepatocytes can produce a stable reduction in HBsAg expression with high specificity that persists for an extended period of time (e.g., greater than 7 weeks to several months) following administration to a subject (See, e.g., Examples 1 and 3). In some embodiments, it has been discovered that targeting of HBsAg expression using oligonucleotides disclosed herein results in reduction of pre-genomic RNA (pgRNA) and other viral life cycle intermediates. It has also been found that certain RNAi oligonucleotides disclosed herein can knockdown HBsAg mRNA transcripts that originate from either cccDNA or integrated virus. In further aspects, it has been discovered that targeting of HBsAg expression using oligonucleotides disclosed herein reduces expression of all HBV proteins (with the exception of HBx), namely HBcAg, HBeAg, and HBV Polymerase, resulting in cytosolic retention of HBV core protein. Furthermore, in some embodiments, clearance of circulating HBsAg resulting from the mRNA knockdown using methods provided herein is clinically advantageous because it enables breaking of HBV immune tolerance caused by high levels of circulating HBsAg in CHB patients. Reactivation of immune system activity against HBV infection is believed to be a cornerstone of achieving functional cure, defined as permanent seroclearance of HBsAg.

Previous work has indicated that the use of a combination of RNAi agents targeting multiple different HBV genes (namely, S, C, P, and X genes), or in some cases targeting X gene transcripts alone, achieves effective inhibition of HBV replication and gene expression. However, results provided herein demonstrate that the use of RNAi oligonucleotides targeting HBsAg transcripts alone also achieves effective inhibition of HBV replication and gene expression, which provides a new therapeutic approach to treating HBV infections. In addition to the direct effect of silencing viral RNAs, HSB(s)-219 precursors prevent nuclear localization of HBV Core Antigen (HBcAg). Importantly, targeting of HBV-X or both genes simultaneously does not prevent HBcAg nuclear localization. Preclinical data strongly suggest that the inhibition of nuclear core localization caused by S-targeting RNAi therapy results in significantly improved duration of HBsAg suppression. Notably, lack of nuclear localization of HBcAg in patients has been shown to correlate to favorable responses to antiviral therapy.

Some aspects of the present disclosure provide oligonucleotides for reducing expression of hepatitis B virus surface antigen (HBsAg) mRNA, the oligonucleotide comprising an antisense strand of 19 to 30 nucleotides in length, wherein the antisense strand comprises a region of complementarity to a sequence of HBsAg mRNA as set forth in ACAANAAUCCUCACAAUA (SEQ ID NO: 1).

In some embodiments, the oligonucleotide further comprises a sense strand of 19 to 50 nucleotides in length, wherein the sense strand forms a duplex region with the antisense strand. In some embodiments, sense strand comprises a region of complementarity to a sequence as set forth in UUNUUGUGAGGAUUN (SEQ ID NO: 2). In some embodiments, the sense strand comprises a region of complementarity to a sequence as set forth in 5'-UUAUU-GUGAGGAUUNUUGUC (SEQ ID NO: 3).

In some embodiments, the antisense strand comprises a sequence as set forth in UUAUUGUGAGGAUUNUUGU-CGG (SEQ ID NO: 4). In some embodiments, the antisense strand consists of a sequence as set forth in UUAUU-GUGAGGAUUCUUGUCGG (SEQ ID NO: 5). In some embodiments, the antisense strand consists of a sequence as set forth in UUAUUGUGAGGAUUUUUGUCGG (SEQ ID NO: 6).

In some embodiments, the sense strand comprises a sequence as set forth in ACAANAAUCCUCACAAUAA (SEQ ID NO: 7). In some embodiments, the sense strand comprises a sequence as set forth in GACAANAAUCCU-CACAAUAAGCAGCCGAAAGGCUGC (SEQ ID NO: 8). In some embodiments, the sense strand consists of a sequence as set forth in GACAAAAAUCCU-CACAAUAAGCAGCCGAAAGGCUGC (SEQ ID NO: 9). In some embodiments, the sense strand consists of a sequence as set forth in GACAAGAAUCCU-CACAAUAAGCAGCCGAAAGGCUGC (SEQ ID NO: 10).

Other aspects of the present disclosure provide oligonucleotides for reducing expression of hepatitis B virus surface antigen (HBsAg) mRNA, the oligonucleotide comprising a sense strand forming a duplex region with an antisense strand, wherein the sense strand comprises a sequence as set forth in GACAAAAAUCCU-CACAAUAAGCAGCCGAAAGGCUGC (SEQ ID NO: 9), wherein the antisense strand comprises a sequence as set forth in UUAUUGUGAGGAUUUUUGUCGG(SEQ ID NO: 6), wherein each of the antisense strand and the sense strand comprises one or more 2'-fluoro and 2'-O-methyl modified nucleotides and at least one phosphorothioate linkage, wherein the 4'-carbon of the sugar of the 5'-nucleotide of the antisense strand comprises a phosphate analog, and wherein the sense strand is conjugated to one or more N-acetylgalactosamine (GalNAc) moiety.

Further provided herein are oligonucleotides for reducing expression of hepatitis B virus surface antigen (HBsAg) mRNA, the oligonucleotide comprising a sense strand forming a duplex region with an antisense strand, wherein: the sense strand comprises a sequence as set forth in GACAAAAAUCCUCACAAUAAGCAGCCGAAAGG-CUGC (SEQ ID NO: 9) and comprising 2'-fluoro modified nucleotides at positions 3, 8-10, 12, 13, and 17, 2'-O-methyl modified nucleotides at positions 1, 2, 4-7, 11, 14-16, 18-26, and 31-36, and at least one phosphorothioate internucleotide linkage, wherein the sense strand is conjugated to one or more N-acetylgalactosamine (GalNAc) moiety; and the antisense strand comprises a sequence as set forth in UUAUU-GUGAGGAUUUUUGUCGG (SEQ ID NO: 6) and comprising 2'-fluoro modified nucleotides at positions 2, 3, 5, 7, 8, 10, 12, 14, 16, and 19, 2'-O-methyl modified nucleotides at positions 1, 4, 6, 9, 11, 13, 15, 17, 18, and 20-22, and at least three phosphorothioate internucleotide linkages, wherein the 4'-carbon of the sugar of the 5'-nucleotide of the antisense strand comprises a phosphate analog. the sense strand comprises a phosphorothioate linkage between the nucleotides at postions 1 and 2.

In some embodiments, the antisense strand comprises five phosphorothioate linkages between nucleotides 1 and 2, 2 and 3, 3 and 4, 20 and 21, and 21 and 22.

In some embodiments, the 5'-nucleotide of the antisense strand has the following structure:

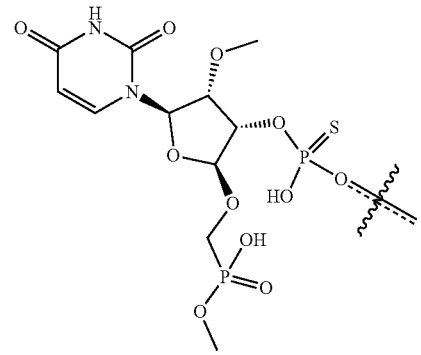

In some embodiments, one or more of the nucleotides of the -GAAA-sequence on the sense strand is conjugated to a monovalent GalNac moiety.

In some embodiments, each of the nucleotides of the -GAAA- sequence on the sense strand is conjugated to a monovalent GalNac moiety. In some embodiments, the -GAAA-motif comprises the structure:

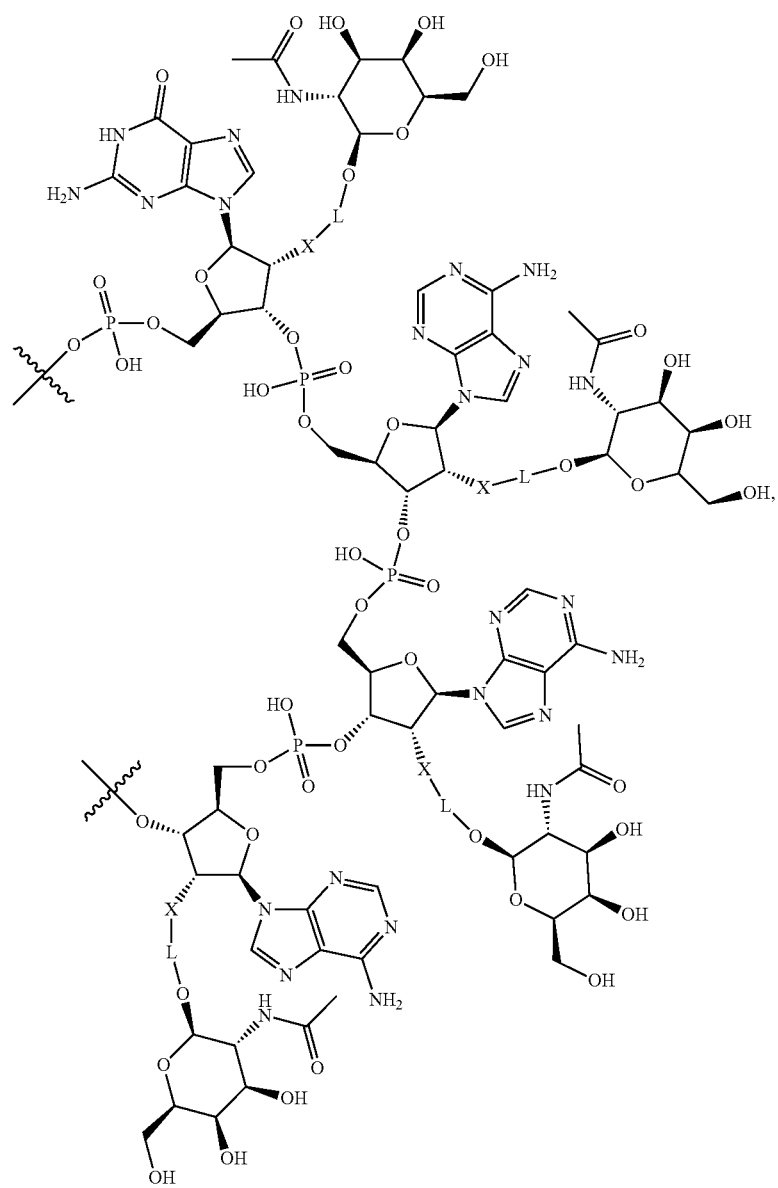

wherein:

L represents a bond, click chemistry handle, or a linker of 1 to 20, inclusive, consecutive, covalently bonded atoms in length, selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, and combinations thereof; and X is a O, S, or N.

In some embodiments, L is an acetal linker. In some embodiments, X is O.

In some embodiments, the -GAAA-sequence comprises the structure:
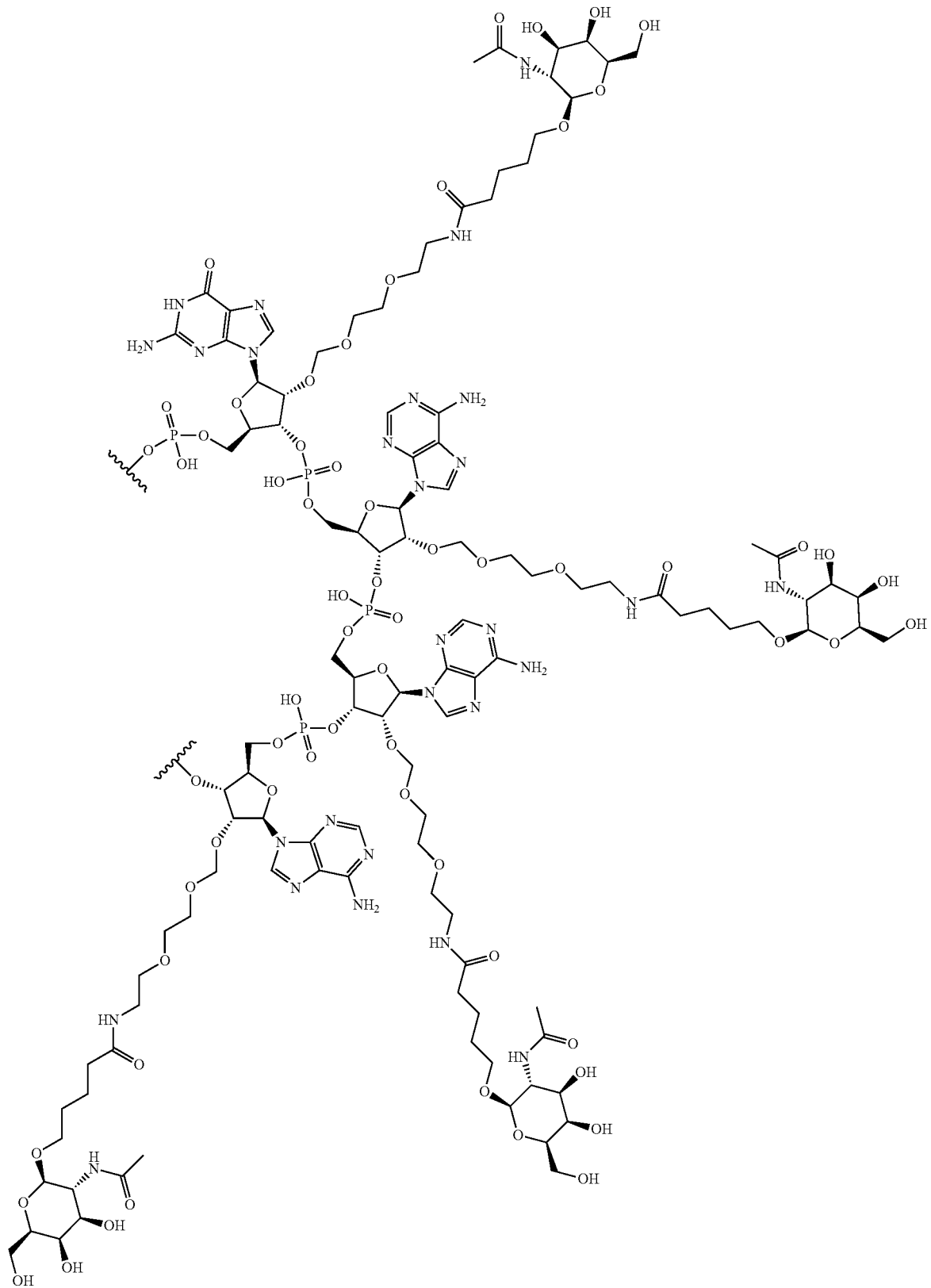 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(=O)(O)O*]

In some embodiments, the sense strand comprises at its 3'-end a stem-loop set forth as: $S_1$-L-$S_2$, wherein $S_1$ is complementary to $S_2$, and wherein L forms a loop between $S_1$ and $S_2$ of up to 6 nucleotides in length. In some embodiments, L is a tetraloop. In some embodiments, L forms a loop between $S_1$ and $S_2$ of 4 nucleotides in length. In some embodiments, L comprises a sequence set forth as GAAA. In some embodiments, up to 4 nucleotides of L of the stem-loop are each conjugated to a separate GalNAc.

In some embodiments, the oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of the oligonucleotide are modified nucleotides. In some embodiments, the oligonucleotide comprises at least one modified internucleotide linkage. In some embodiments, the at least one modified internucleotide linkage is a phosphorothioate linkage the 4'-carbon of the sugar of the 5'-nucleotide of the antisense strand comprises a phosphate analog.

In some embodiments, at least one nucleotide of the oligonucleotide is conjugated to a targeting ligand. In some embodiments, the targeting ligand is a N-acetylgalactosamine (GalNAc) moiety.

Further provided herein are compositions comprising an oligonucleotide of any one of the preceding claims and an counterion, and compositions comprising an oligonucleotide of any one of the preceding claims and a pharmaceutically acceptable carrier.

Other aspects of the present disclosure provide methods of reducing expression of hepatitis B virus (HBV) surface antigen in a cell, the method comprising delivering to the cell an oligonucleotide described herein. In some embodiments, the cell is a hepatocyte. In some embodiments, the cell is in vivo. In some embodiments, the cell is in vitro.

Other aspects of the present disclosure provide methods of treating a hepatitis B virus (HBV) infection in a subject, the method comprising administering to the subject an oligonucleotide of or a composition described herein.

Methods of treating HBV infection in a subject are also provided, the method comprising administering to the subject an RNAi oligonucleotide that selectively targets HBsAg mRNA, wherein the RNAi oligonucleotide is administered in the absence of treatment with an RNAi oligonucleotide targeting a non-surface antigen encoding HBV mRNA transcript. Methods of treating HBV infection in a subject are also provided, the method comprising administering to the subject an RNAi oligonucleotide that selectively targets HBsAg mRNA, wherein the subject is not administered an RNAi oligonucleotide that selectively targets HBxAg mRNA transcript. In some embodiments, the method further comprises administering to the subject an effective amount of Entecavir.

Other aspect of the present disclosure provide oligonucleotides for reducing expression of hepatitis B virus surface antigen (HBsAg) mRNA, the oligonucleotide comprising a sense strand forming a duplex region with an antisense strand, wherein:

the sense strand comprises a sequence as set forth in GACAAAAAUCCUCACAAUAAGCAGCCGAAAGG-CUGC (SEQ ID NO: 9) and comprising 2'-fluoro modified nucleotides at positions 3, 8-10, 12, 13, and 17, 2'-O-methyl modified nucleotides at positions 1, 2, 4-7, 11, 14-16, 18-26, and 31-36, and one phosphorothioate internucleotide linkage between the nucleotides at postions 1 and 2, wherein each of the nucleotides of the -GAAA- sequence on the sense strand is conjugated to a monovalent GalNac moiety, wherein the -GAAA- sequence comprises the structure:

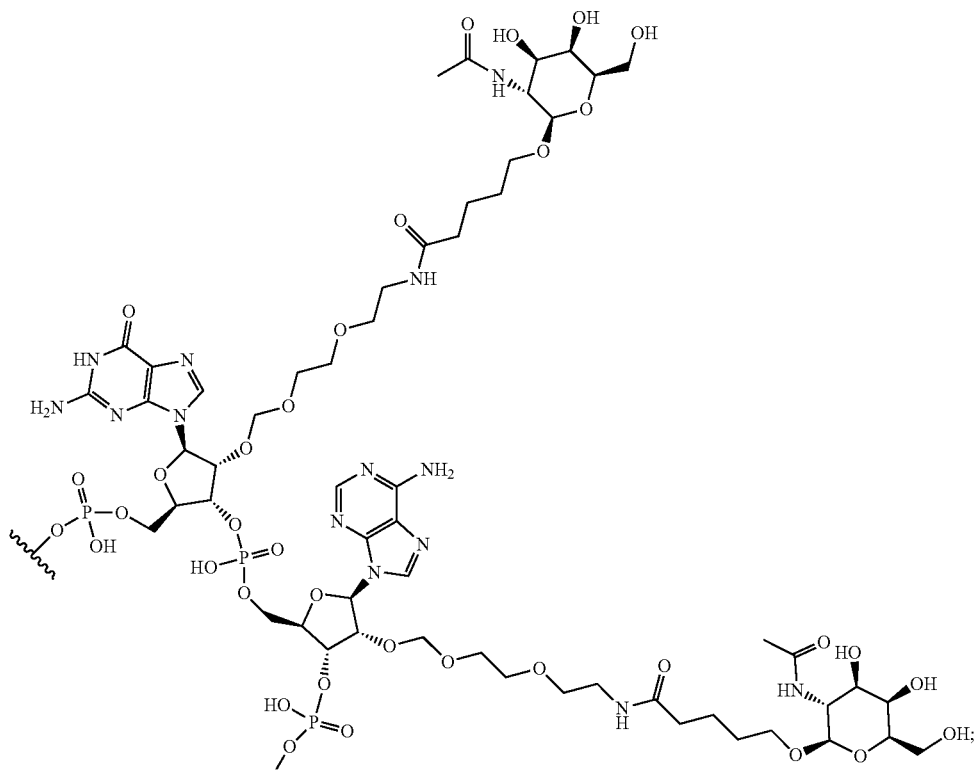

-continued

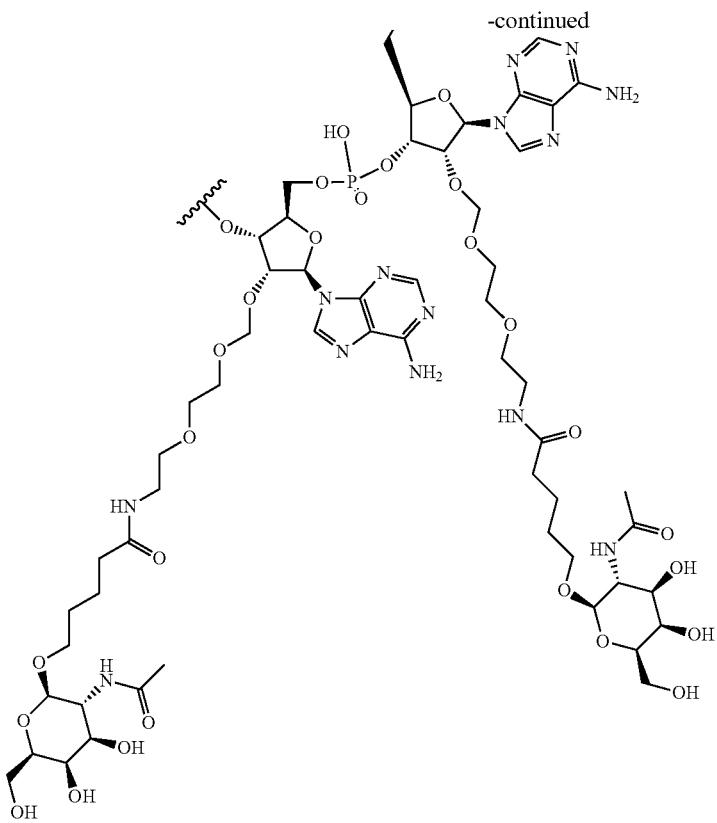

and
the antisense strand comprises a sequence as set forth in UUAUUGUGAGGAUUUUUGUCGG (SEQ ID NO: 6) and comprising 2'-fluoro modified nucleotides at positions 2, 3, 5, 7, 8, 10, 12, 14, 16, and 19, 2'-O-methyl modified nucleotides at positions 1, 4, 6, 9, 11, 13, 15, 17, 18, and 20-22, and five phosphorothioate internucleotide linkages between nucleotides 1 and 2, 2 and 3, 3 and 4, 20 and 21, and 21 and 22, wherein the 4'-carbon of the sugar of the 5'-nucleotide of the antisense strand has the following structure:

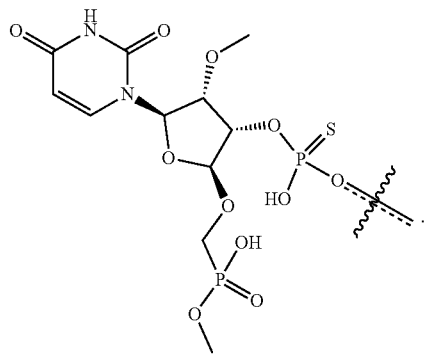

Composition comprising the oligonucleotide is also provided. In some embodiments, the composition further comprises Na+ counterions.

Also provided are methods of reducing expression of hepatitis B virus (HBV) surface antigen in a cell, the method comprising delivering to the oligonucleotide or the composition. In some embodiments, the cell is a hepatocyte. In some embodiments, the cell is in vivo. In some embodiments, the cell is in vitro.

Methods of treating a hepatitis B virus (HBV) infection in a subject are provided, the method comprising administering to the subject the oligonucleotide or the composition. In some embodiments, the method further comprises administering to the subject an effective amount of Entecavir.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIG. 7 shows several examples of oligonucleotides designed to evaluate the effects of introducing mismatches. Oligonucleotide sequences for parent and mismatch strands are shown aligned and with mismatch positions in boxes. The corresponding reporter sequences used in psiCHECK2 reporter assays are further depicted.

FIG. 16A shows the location of RNAi target site in HBV genome affects HBsAg recovery kinetics in HBV-expressing mice. FIG. 16B shows plasma HBsAg level2 weeks post-dose (left panel) and 9 weeks pose-dose (right panel), indicating that targeting the HBVX coding region, either alone or in combination with HBV(s)-219P2, results in shorter duration of activity. Individual animal data was shown. Several data points (lighest grey circles) were below limit of detection.

FIG. 17A shows representative hepatocytes in liver sections obtained at weeks 1, 2, 6, 9, and 13 post administration and stained for HBcAg. FIG. 17B shows the percentage of HBcAg-positive-cells with nuclear staining in each animal (n=3/group, 50 cells counted per animal, 2 weeks after dosing). Alternative sequences were designed and tested targeting within the X and S open reading frames. FIG. 17C shows subcellular distribution of HBcAg in hepatocytes obtained at weeks 2, 3, and 9 post administration of an alternative RNAi oligo targeting either the S antigen and the X antigen.

FIG. 18 shows the dose by cohort information for a study designed to evaluate the safety and tolerability of HBV(s)-219 in healthy patients and the therapeutic efficacy of HBV(s)-219 in HBV patients.

(FIG. 19A) Chemical structure for HBV(s)-219. (FIG. 19B) Chemical structure for HBV(s)-219P2.

FIG. 20 shows a focused conservation analysis.

DETAILED DESCRIPTION OF THE INVENTION

Figure 1:
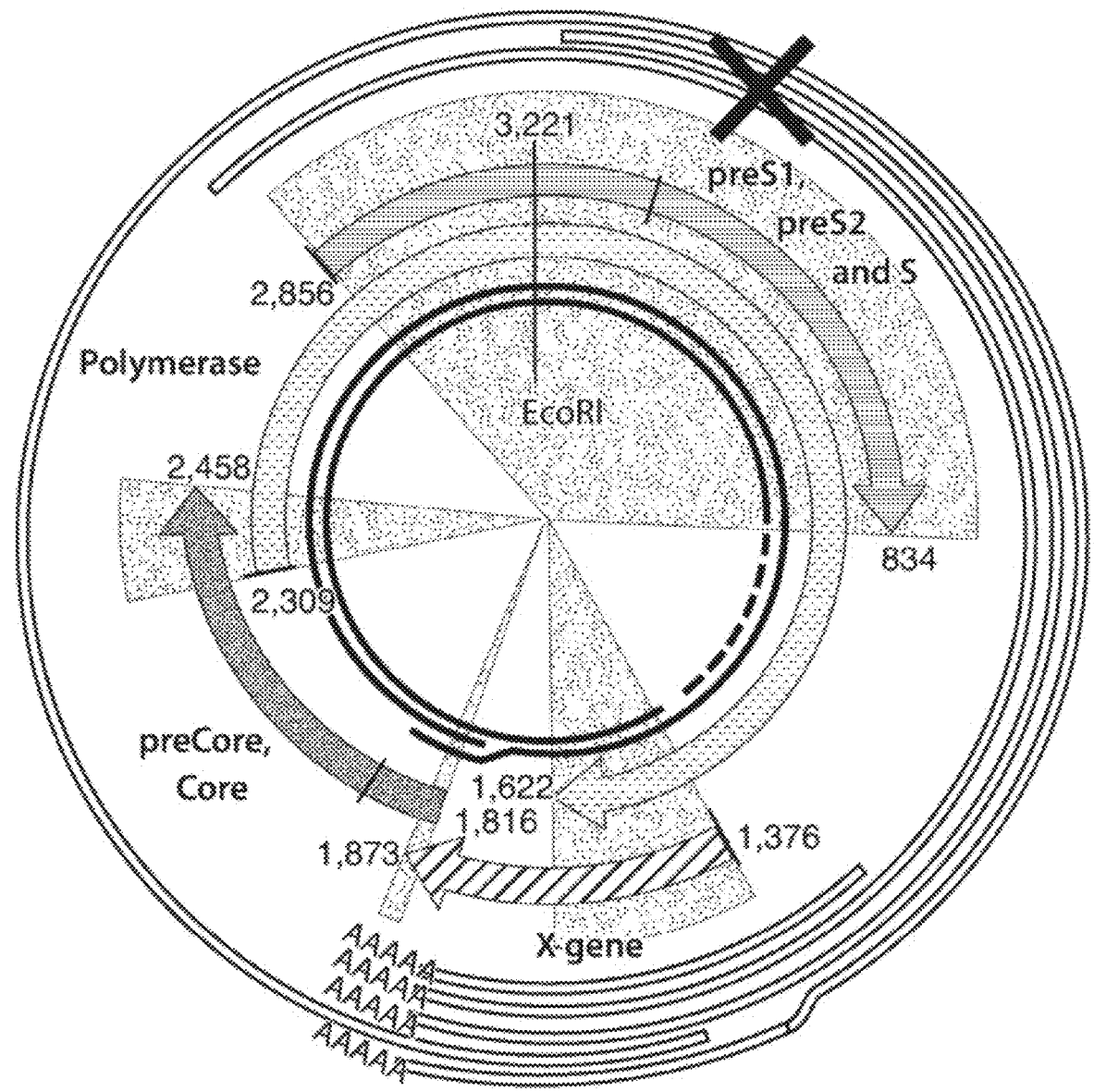
FIG. 1 shows an example of an RNAi target site on a schematic representation of the organization of the HBV genome.

According to some aspects, the disclosure provides potent oligonucleotides that are effective for reducing HBsAg expression in cells, particularly liver cells (e.g., hepatocytes) for the treatment of HBV infections. In certain embodiments, HBsAg targeting oligonucleotides provided herein are designed for delivery to selected cells of target tissues (e.g., liver hepatocytes) to treat HBV infection in those tissues. Accordingly, in related aspects, the disclosure provides methods of treating HBV infection that involve selectively reducing HBV surface antigen gene expression in cells (e.g., cells of the liver).

Further aspects of the disclosure, including a description of defined terms, are provided below.

I. Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administering: As used herein, the terms "administering" or "administration" means to provide a substance (e.g., an oligonucleotide) to a subject in a manner that is pharmacologically useful (e.g., to treat a condition in the subject).

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

Complementary: As used herein, the term "complementary" refers to a structural relationship between two nucleotides (e.g., on two opposing nucleic acids or on opposing regions of a single nucleic acid strand), or between two sequences of nucleotides, that permits the two nucleotides, or two sequences of nucleotides, to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other so as to form regions of complementarity, as described herein.

Deoxyribonucleotide: As used herein, the term "deoxyribonucleotide" refers to a nucleotide having a hydrogen in place of a hydroxyl at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base-pairing of two antiparallel sequences of nucleotides.

Excipient: As used herein, the term "excipient" refers to a non-therapeutic agent that may be included in a composition, for example, to provide or contribute to a desired consistency or stabilizing effect.

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glul), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Hepatitis B Virus: As used herein, the term "Hepatitis B Virus" or "HBV" refers to a small DNA virus belonging to the Hepadnaviridae family and classified as the type species of the genus *Orthohepadnavirus*. HBV virus particles (virions) comprise an outer lipid envelope and an icosahedral nucleocapsid core composed of protein. The nucleocapsid generally encloses viral DNA and a DNA polymerase that has reverse transcriptase activity similar to retroviruses. The HBV outer envelope contains embedded proteins which are involved in viral binding of, and entry into, susceptible cells. HBV, which attacks the liver, has been classified according to at least ten genotypes (A-J) based on sequence. In general, there are four genes encoded by the genome, which genes are referred to as C, P, S, and X. The core protein is encoded by gene C (HBcAg), and its start codon is preceded by an upstream in-frame AUG start codon from which the pre-core protein is produced. HBeAg is produced by proteolytic processing of the pre-core protein. The DNA polymerase is encoded by gene P. Gene S encodes surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. These may have a ratio of 1:1:4 (Heermann et al, 1984).

Hepatitis B Virus (HBV) proteins can be organized into several categories and functions. Polymerases function as a reverse transcriptase (RT) to make viral DNA from pregenomic RNA (pgRNA), and also as a DNA-dependent polymerase to make covalently closed circular DNA (cccDNA) from viral DNA. They are covalently attached to the 5' end of the minus strand. Core proteins make the viral capsid and the secreted E antigen. Surface antigens are the hepatocyte internalization ligands, and also the primary component of aviral spherical and filamentous particles. Aviral particles are produced >1000-fold over Dane particles (infectious virions) and may act as immune decoys.

Hepatitis B virus surface antigen: As used herein, the term "hepatitis B virus surface antigen" or "HBsAg" refers to an S-domain protein encoded by gene S (e.g., ORF S) of an HBV genome. Hepatitis B virus particles carry viral nucleic acid in core particles enveloped by three proteins encoded by gene S, which are the large surface, middle surface, and major surface proteins. Among these proteins, the major surface protein is generally about 226 amino acids and contains just the S-domain.

Infection: As used herein, the term "infection" reefs to the pathogenic invasion and/or expansion of microorganisms, such as viruses, in a subject. An infection may be lysogenic, e.g., in which viral DNA lies dormant within a cell. Alternatively, an infection may be lytic, e.g., in which viruses actively proliferates and causing destruction of infected cells. An infection may or may not cause clinically apparent symptoms. An infection may remain localized, or it may spread, e.g., through a subjects blood or lymphatic system. An individual having, for example, an HBV infection, can be identified by detecting one or more of viral load, surface antigen (HBsAg), e-antigen (HBeAg), and various other assays for detecting HBV infection known in the art. Assays for detection of HBV infection can involve testing serum or blood samples for the presence of HBsAg and/or HBeAg, and optionally further screening for the presence of one or more viral antibodies (e.g., IgM and/or IgG) to compensate for any periods in which an HBV antigen may be at an undetectable level.

Liver inflammation: As used herein, the term "liver inflammation" or "hepatitis" refers to a physical condition in which the liver becomes swollen, dysfunctional, and/or painful, especially as a result of injury or infection, as may be caused by exposure to a hepatotoxic agent. Symptoms may include jaundice (yellowing of the skin or eyes), fatigue, weakness, nausea, vomiting, appetite reduction, and weight loss. Liver inflammation, if left untreated, may progress to fibrosis, cirrhosis, liver failure, or liver cancer.

Liver fibrosis: As used herein, the term "liver fibrosis" or "fibrosis of the liver" refers to an excessive accumulation in the liver of extracellular matrix proteins, which could include collagens (I, III, and IV), fibronectin, undulin, elastin, laminin, hyaluronan, and proteoglycans resulting from inflammation and liver cell death. Liver fibrosis, if left untreated, may progress to cirrhosis, liver failure, or liver cancer.

Loop: As used herein, the term "loop" refers to a unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to a internucleotide linkage having one or more chemical modifications compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

Nicked Tetraloop Structure: A "nicked tetraloop structure" is a structure of a RNAi oligonucleotide characterized by the presence of separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

Oligonucleotide: As used herein, the term "oligonucleotide" refers to a short nucleic acid, e.g., of less than 100 nucleotides in length. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotides.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, U.S. Provisional Application No. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to an HBsAg mRNA sequence) may result in a decrease in the amount of RNA transcript, protein and/or enzymatic activity (e.g., encoded by the S gene of an HBV genome) compared to a cell that is not treated with the double-stranded oligonucleotide. Similarly, "reducing expression" as used herein refers to an act that results in reduced expression of a gene (e.g., the S gene of an HBV genome).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides to permit hybridization between the two sequences of nucleotides under appropriate hybridization conditions, e.g., in a phosphate buffer, in a cell, etc.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C. or at least 75° C. in 10 mM NaHPO$_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include but are not limited to non-Watson-Crick base-pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., an existing HBV infection) or to prevent or decrease the likelihood of the occurrence of a condition (e.g., preventing liver fibrosis, hepatitis, liver cancer or other condition associated with an HBV infection). In some embodiments, treatment involves reducing the frequency or severity of at least one sign, symptom or contributing factor of a condition (e.g., HBV infection or related condition) experienced by a subject. During an HBV infection, a subject may exhibit symptoms such as yellowing of the skin and eyes (jaundice), dark urine, extreme fatigue, nausea, vomiting and abdominal pain. Accordingly, in some embodiments, a treatment provided herein may result in a reduction in the frequency or severity of one or more of such symptoms. However, HBV infection can develop into one or more liver conditions, such as cirrhosis, liver fibrosis, liver inflammation or liver cancer. Accordingly, in some embodiments, a treatment provided herein may result in a reduction in the frequency or severity of, or prevent or attenuate, one or more of such conditions.

II. Oligonucleotide-Based Inhibitors i. HBV Surface Antigen Targeting

In some embodiments, oligonucleotide-based inhibitors of HBV surface antigen expression are provided herein that can be used to achieve a therapeutic benefit. Through examination of HBV surface antigen mRNA and testing of different oligonucleotides, potent oligonucleotides have been developed for reducing expression of HBV surface antigen (HBsAg) to treat HBV infection. Oligonucleotides provided herein, in some embodiments, are designed to target HBsAg mRNA sequences covering >95% of known HBV genomes across all known genotypes. In some embodiments, such oligonucleotides result in more than 90% reduction of HBV pre-genomic RNA (pgRNA) and HBsAg mRNAs in liver. In some embodiments, the reduction in HBsAg expression persists for an extended period of time following a single dose or treatment regimen.

Accordingly, in some embodiments, oligonucleotides provided herein are designed so as to have regions of complementarity to HBsAg mRNA for purposes of targeting the transcripts in cells and inhibiting their expression. The region of complementarity is generally of a suitable length and base content to enable annealing of the oligonucleotide (or a strand thereof) to HBsAg mRNA for purposes of inhibiting its expression. In some embodiments, the region of complementarity is at least 12, at least 13, at least 14, at least 15, at least 16, at least 17, at least 18, at least 19 or at least 20 nucleotides in length. In some embodiments, an oligonucleotide provided herein has a region of complementarity to HBsAg mRNA that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to HBsAg mRNA that is 12, 13, 14, 15, 16, 17, 18, 19, 20, 21, 22, 23, 24, 25, 26, 27, 28, 29 or 30 nucleotides in length.

In some embodiments, oligonucleotides provided herein are designed to target mRNA sequences encoding HBsAg. For example, in some embodiments, an oligonucleotide is provided that has an antisense strand having a region of complementarity to a sequence set forth as: ACAANAAUC-CUCACAAUA (SEQ ID NO: 1), which N refers to any nucleotide (A, G, T, or C). In some embodiments, the oligonucleotide further comprises a sense strand that forms a duplex region with the antisense strand. In some embodiments, the sense strand has a region of complementarity to a sequence set forth as: UUNUUGUGAGGAUUN (SEQ ID NO: 2). In some embodiments, the sense strand comprises a region of complementarity to a sequence as set forth in (shown 5' to 3'): UUAUUGUGAGGAUUNUUGUC (SEQ ID NO: 3).

In some embodiments, the antisense strand comprises, or consists of, a sequence set forth as: UUAUUGUGAGGAU-UNUUGUCGG (SEQ ID NO: 4). In some embodiments, the antisense strand comprises, or consists of, a sequence set forth as: UUAUUGUGAGGAUUCUUGUCGG (SEQ ID NO: 5). In some embodiments, the antisense strand comprises, or consists of, a sequence set forth as: UUAUU-GUGAGGAUUUUUGUCGG (SEQ ID NO: 6). In some embodiments, the sense strand comprises, or consists of, a sequence set forth as: ACAANAAUCCUCACAAUAA (SEQ ID NO: 7). In some embodiments, the sense strand comprises, or consists of, a sequence set forth as: GACAA-NAAUCCUCACAAUAAGCAGCCGAAAGGCUGC (SEQ ID NO: 8). In some embodiments, the sense strand comprises, or consists of, a sequence set forth as: GACAAAAAUCCUCACAAUAAGCAGCCGAAAGG-CUGC (SEQ ID NO: 9). In some embodiments, the sense strand comprises, or consists of, a sequence set forth as: GACAAGAAUCCUCACAAUAAGCAGCCGAAAGG-CUGC (SEQ ID NO: 10).

In some embodiments, an oligonucleotide for reducing expression of HBsAg mRNA comprises a sense strand forming a duplex region with an antisense strand, where the sense strand comprises a sequence as set forth in any one of SEQ ID NOs: 7-10, and the antisense strand comprises a sequence as set forth in any one of SEQ ID NOs: 4-6. In some embodiments, the sense strand comprises 2'-fluoro and 2'-O-methyl modified nucleotides and at least one phosphorothioate internucleotide linkage. In some embodiments, the sense strand is conjugated to a N-acetylgalactosamine (GalNAc) moiety. In some embodiments, the antisense strand comprises 2'-fluoro and 2'-O-methyl modified nucleotides and at least one phosphorothioate internucleotide linkage. In some embodiments, the 4'-carbon of the sugar of the 5'-nucleotide of the antisense strand comprises a phosphate analog. In some embodiments, each of the antisense strand and the sense strand comprises 2'-fluoro and 2'-O-methyl modified nucleotides and at least one phosphorothioate internucleotide linkage, where the 4'-carbon of the sugar of the 5'-nucleotide of the antisense strand comprises a phosphate analog, and the sense strand is conjugated to a N-acetylgalactosamine (GalNAc) moiety.

In some embodiments, a sense strand comprising a sequence as set forth in any one of SEQ ID NOs: 8-10 comprises 2'-fluoro modified nucleotides at positions 3, 8-10, 12, 13, and 17. In some embodiments, the sense strand comprises 2'-O-methyl modified nucleotides at positions 1, 2, 4-7, 11, 14-16, 18-26, and 31-36. In some embodiments, the sense strand comprises one phosphorothioate internucleotide linkage. In some embodiments, the sense strand comprises a phosphorothioate internucleotide linkage between nucleotides at positions 1 and 2. In some embodiments, the sense strand is conjugated to a N-acetylgalactosamine (GalNAc) moiety.

In some embodiments, an antisense strand comprising a sequence as set forth in any one of SEQ ID NOs: 4-6 comprises 2'-fluoro modified nucleotides at positions 2, 3, 5, 7, 8, 10, 12, 14, 16, and 19. In some embodiments, the antisense strand comprises 2'-O-methyl modified nucleotides at positions 1, 4, 6, 9, 11, 13, 15, 17, 18, and 20-22. In some embodiments, the antisense strand comprises three phosphorothioate internucleotide linkages. In some embodiments, the antisense strand comprises phosphorothioate internucleotide linkages between nucleotides at positions 1 and 2, between nucleotides at positions 2 and 3, between nucleotides at positions 3 and 4, between nucleotides at positions 20 and 21, and between nucleotides at positions 21 and 22. In some embodiments, the 4'-carbon of the sugar of the 5'-nucleotide of the antisense strand comprises a phosphate analog.

ii. Double-Stranded Oligonucleotides

There are a variety of structures of oligonucleotides that are useful for targeting HBsAg mRNA expression in the methods of the present disclosure, including RNAi, antisense, miRNA, etc. Any of the structures described herein or elsewhere may be used as a framework to incorporate or target a sequence described herein. Double-stranded oligonucleotides for targeting HBV antigen expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked.

In some embodiments, double-stranded oligonucleotides for reducing the expression of HBsAg mRNA expression engage RNA interference (RNAi). For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by Dicer to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, oligonucleotides provided herein are cleavable by Dicer enzymes. Such oligonucleotides may have an overhang (e.g., of 1, 2, or 3 nucleotides in length) in the 3' end of the sense strand. Such oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. Longer oligonucleotide designs are also available including oligonucleotides having a guide strand of 23 nucleotides and a passenger strand of 21 nucleotides, where there is a blunt end on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 21 base pair duplex region. See, for example, U.S. Pat. Nos. 9,012,138, 9,012,621, and 9,193,753, each of which are incorporated herein for their relevant disclosures.

In some embodiments, oligonucleotides as disclosed herein may comprise sense and antisense strands that are both in the range of 17 to 26 (e.g., 17 to 26, 20 to 25, 19 to 21 or 21-23) nucleotides in length. In some embodiments, the sense and antisense strands are of equal length. In some embodiments, for oligonucleotides that have sense and antisense strands that are both in the range of 21-23 nucleotides in length, a 3' overhang on the sense, antisense, or both sense and antisense strands is 1 or 2 nucleotides in length. In some embodiments, the oligonucleotide has a guide strand of 23 nucleotides and a passenger strand of 21 nucleotides, where there is a blunt end on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 21 base pair duplex region. In some embodiments, a oligonucleotide comprises a 25 nucleotide sense strand and a 27 nucleotide antisense strand that when acted upon by a dicer enzyme results in an antisense strand that is incorporated into the mature RISC.

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p 163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p 193-198), single-stranded siRNAs (Elsner; Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of HBsAg are microRNA (miRNA), short hairpin RNA (shRNA), and short siRNA (see, e.g., Hamilton et al., Embo J., 2002, 21(17): 4671-4679; see also U.S. Application No. 20090099115).

a. Antisense Strands

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments, a sense strand complementary with a guide strand may be referred to as a "passenger strand."

In some embodiments, an oligonucleotide provided herein comprises an antisense strand that is up to 50 nucleotides in length (e.g., up to 30, up to 27, up to 25, up to 21, or up to 19 nucleotides in length). In some embodiments, an oligonucleotide provided herein comprises an antisense strand that is at least 12 nucleotides in length (e.g., at least 12, at least 15, at least 19, at least 21, at least 25, or at least 27 nucleotides in length). In some embodiments, an antisense strand of an oligonucleotide disclosed herein is in the range of 12 to 50 or 12 to 30 (e.g., 12 to 30, 11 to 27, 11 to 25, 15 to 21, 15 to 27, 17 to 21, 17 to 25, 19 to 27, or 19 to 30) nucleotides in length. In some embodiments, an antisense strand of any one of the oligonucleotides disclosed herein is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, the antisense strand comprises a region of complementarity to a sequence as set forth in (shown 5' to 3'): AATCCTCACA (SEQ ID NO: 11). In some embodiments, the antisense strand comprises a sequence as set forth in (shown 5' to 3'): UGUGAGGAUU (SEQ ID NO: 12). In some embodiments, the antisense strand comprises a sequence as set forth in (shown 5' to 3'): TGTGAGGATT (SEQ ID NO: 13).

In some embodiments, an oligonucleotide for reducing expression of HBsAg mRNA can comprise an antisense strand having a region of complementarity to a sequence as set forth in SEQ ID NO: 11, and one or two non-complementary nucleotides at its 3' terminus. In some embodiments, the antisense strand comprises the nucleotide sequence set forth in any one of SEQ ID NOs: 4-6.

In some embodiments, an oligonucleotide for reducing expression of HBsAg mRNA can comprise an antisense strand that has a region of complementarity to a sequence as set forth in SEQ ID NO: 11, where the antisense strand does not have a sequence as set forth in any one of the following (shown 5' to 3'): TATTGTGAGGATTCTTGTCA (SEQ ID NO: 14); CGGTATTGTGAGGATTCTTG (SEQ ID NO: 15); TGTGAGGATTCTTGTCAACA (SEQ ID NO: 16); UAUUGUGAGGAUUUUUGUCAA (SEQ ID NO: 17); UGCGGUAUUGUGAGGAUUCTT (SEQ ID NO: 18); ACAGCATTGTGAGGATTCTTGTC (SEQ ID NO: 19); UAUUGUGAGGAUUUUUGUCAACA (SEQ ID NO: 20); AUUGUGAGGAUUUUUGUCAACAA (SEQ ID NO: 21); and UUGUGAGGAUUUUUGUCAACAAG (SEQ ID NO: 22). In some embodiments, the antisense strand differs from the nucleotide sequence set forth in SEQ ID NOs: 4, 5, or 6 by no more than three nucleotides.

b. Sense Strands

In some embodiments, a double-stranded oligonucleotide may have a sense strand of up to 40 nucleotides in length (e.g., up to 40, up to 35, up to 30, up to 27, up to 25, up to 21, up to 19, up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 35, or at least 38 nucleotides in length). In some embodiments, an oligonucleotide may have a sense strand in a range of 12 to 50 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, a sense strand of an oligonucleotide is longer than 27 nucleotides (e.g., 28, 29, 30, 31, 32, 33, 34, 35, 36, 37, 38, 39 or 40 nucleotides). In some embodiments, a sense strand of an oligonucleotide is longer than 25 nucleotides (e.g., 26, 27, 28, 29 or 30 nucleotides).

In some embodiments, a sense strand comprises a stem-loop at its 3'-end. In some embodiments, a sense strand comprises a stem-loop at its 5'-end. In some embodiments, a strand comprising a stem loop is in the range of 2 to 66 nucleotides long (e.g., 2 to 66, 10 to 52, 14 to 40, 2 to 30, 4 to 26, 8 to 22, 12 to 18, 10 to 22, 14 to 26, or 14 to 30 nucleotides long). In some embodiments, a strand comprising a stem loop is 8, 9, 10, 11, 12, 13, 14, 15, 16, 17, 18, 19, 20, 21, 22, 23, 24, 25, 26, 27, 28, 29, or 30 nucleotides in length. In some embodiments, a stem comprises a duplex of 1, 2, 3, 4, 5, 6, 7, 8, 9, 10, 11, 12, 13, or 14 nucleotides in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 1, 2, 3, 4, 5, 6, 7, 8, 9, or 10 nucleotides in length).

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides.

c. Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

d. Oligonucleotide Ends

In some embodiments, an oligonucleotide comprises sense and antisense strands, such that there is a 3'-overhang on either the sense strand or the antisense strand, or both the sense and antisense strand. In some embodiments, oligonucleotides provided herein have one 5'-end that is thermodynamically less stable compared to the other 5' end. In some embodiments, an asymmetry oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7 or 8 nucleotides in length).

Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, one or more (e.g., 2, 3, 4) terminal nucleotides of the 3' end or 5' end of a sense and/or antisense strand are modified. For example, in some embodiments, one or two terminal nucleotides of the 3' end of an antisense strand are modified. In some embodiments, the last nucleotide at the 3' end of an antisense strand is modified, e.g., comprises 2'-modification, e.g., a 2'-O-methoxyethyl. In some embodiments, the last one or two terminal nucleotides at the 3' end of an antisense strand are complementary with the target. In some embodiments, the last one or two nucleotides at the 3' end of the antisense strand are not complementary with the target.

In some embodiments, a double stranded oligonucleotide is provided that has a nicked tetraloop structure at the 3' end sense strand, and two terminal overhang nucleotides at the 3' end of its antisense strand. In some embodiments, the two terminal overhang nucleotides are GG. Typically, one or both of the two terminal GG nucleotides of the antisense strand is or are not complementary with the target.

In some embodiments, the 5' end and/or the 3' end of a sense or antisense strand has an inverted cap nucleotide.

In some embodiments, one or more (e.g., 2, 3, 4, 5, 6) modified internucleotide linkages are provided between terminal nucleotides of the 3' end or 5' end of a sense and/or antisense strand. In some embodiments, modified internucleotide linkages are provided between overhang nucleotides at the 3' end or 5' end of a sense and/or antisense strand.

e. Mismatches

In some embodiments, an oligonucleotide may have one or more (e.g., 1, 2, 3, 4, 5) mismatches between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

In some embodiments, an antisense strand may have a region of complementarity to an HBsAg transcript that contains one or more mismatches compared with a corresponding transcript sequence. A region of complementarity on an oligonucleotide may have up to 1, up to 2, up to 3, up to 4, up to 5, etc. mismatches provided that it maintains the ability to form complementary base pairs with the transcript under appropriate hybridization conditions. Alternatively, a region of complementarity of an oligonucleotide may have no more than 1, no more than 2, no more than 3, no more than 4, or no more than 5 mismatches provided that it maintains the ability to form complementary base pairs with HBsAg mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with HBsAg mRNA under appropriate hybridization conditions.

iii. Single-Stranded Oligonucleotides

In some embodiments, an oligonucleotide for reducing HBsAg expression as described herein is single-stranded oligonucleotides having complementarity with HBsAg mRNA. Such structures may include, but are not limited to single-stranded RNAi oligonucleotides. Recent efforts have demonstrated the activity of single-stranded RNAi oligonucleotides (see, e.g., Matsui et al. (May 2016) Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier, it may be advantageous for at least some of the its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every sugar is modified at the 2'-position. These modifications may be reversible or irreversible. In some embodiments, an oligonucleotide as disclosed herein has a number and type of modified nucleotides sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred to herein as a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659).

Koshkin et al., Snead et al., and Imanishi and Obika are incorporated by reference herein for their disclosures relating to sugar modifications.

In some embodiments, a nucleotide modification in a sugar comprises a 2'-modification. A 2'-modification may be 2'-aminoethyl, 2'-fluoro, 2'-O-methyl, 2'-O-methoxyethyl, and 2'-deoxy-2'-fluoro-β-d-arabinonucleic acid. Typically, the modification is 2'-fluoro, 2'-O-methyl, or 2'-O-methoxyethyl. In some embodiments, a modification in a sugar comprises a modification of the sugar ring, which may comprise modification of one or more carbons of the sugar ring. For example, a modification of a sugar of a nucleotide may comprise a 2'-oxygen of a sugar is linked to a 1'-carbon or 4'-carbon of the sugar, or a 2'-oxygen is linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) is a phosphate group or other group, which can be used, for example, to attach linkers, adapters or labels or for the direct ligation of an oligonucleotide to another nucleic acid.

b. 5' Terminal Phosphates

In some embodiments, 5'-terminal phosphate groups of oligonucleotides enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to a chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, U.S. Provisional Application No. 62/383,207, entitled 4'-Phosphate Analogs and Oligonucleotides Comprising the Same, filed on Sep. 2, 2016, and 62/393,401, filed on Sep. 12, 2016, entitled 4' Phosphate Analogs and Oligonucleotides Comprising the Same, the contents of each of which relating to phosphate analogs are incorporated herein by reference. In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—CH$_2$—PO(OH)$_2$ or —O—CH$_2$—PO(OR)$_2$, in which R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$, or a protecting group. In certain embodiments, the alkyl group is CH$_2$CH$_3$. More typically, R is independently selected from H, CH$_3$, or CH$_2$CH$_3$.

In certain embodiments, a phosphate analog attached to the oligonucleotide is a methoxy phosphonate (MOP). In certain embodiments, a phosphate analog attached to the oligonucleotide is a 5' mono-methyl protected MOP. In some embodiments, the following uridine nucleotide comprising a phosphate analog may be used, e.g., at the first position of a guide (antisense) strand:

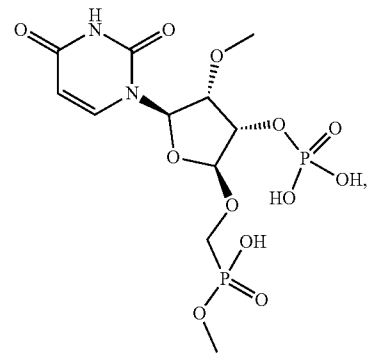 [SMILES: CO[C@@H]1[C@H](OP(=O)(O)O)[C@@H](OCP(=O)(O)OC)O[C@H]1n1ccc(=O)[nH]c1=O]

which modified nucleotide is referred to as [MePhosphonate-4O-mU] or 5'-Methoxy, Phosphonate-4'oxy-2'-O-methyluridine.

c. Modified Internucleoside Linkages

In some embodiments, phosphate modifications or substitutions may result in an oligonucleotide that comprises at least one (e.g., at least 1, at least 2, at least 3 or at least 5) modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorothioate linkage, a phosphorothioate linkage, a phosphotriester linkage, a thionoalkylphosphonate linkage, a thionoalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

d. Base Modifications

In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain a nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution that, when present in a duplex, can be positioned opposite more than one type of base without substantially altering the structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include inosine, 143-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., Nature Biotechnology, 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. J. Am. Chem. Soc. 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of a sugar, particularly when the modified nucleotide is the 3'-terminal nucleotide of the oligonucleotide. In some embodiments, the glutathione-sensitive moiety comprises a sulfonyl group. See, e.g., U.S. Prov. Appl. No. 62/378,635, entitled Compositions Comprising Reversibly Modified Oligonucleotides and Uses Thereof, which was filed on Aug. 23, 2016, the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligands.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferrin, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a targeting ligand.

In some embodiments, it is desirable to target an oligonucleotide that reduces the expression of HBV antigen to the hepatocytes of the liver of a subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to one or more bivalent GalNAc, trivalent GalNAc, or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand, where each GalNAc moiety is conjugated to one nucleotide.

In some embodiments, an oligonucleotide herein comprises a monovalent GalNac attached to a Guanidine nucleotide, referred to as [ademG-GalNAc] or 2'-aminodiethoxymethanol-Guanidine-GalNAc, as depicted below:

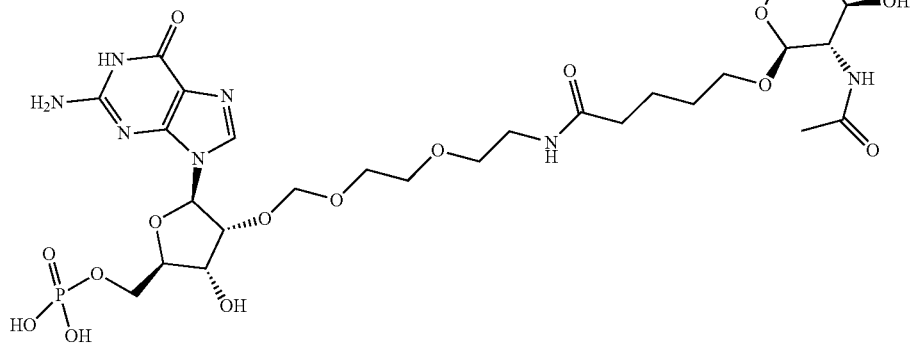

In some embodiments, an oligonucleotide herein comprises a monovalent GalNac attached to an adenine nucleotide, referred to as [ademA-GalNAc] or 2'-aminodiethoxymethanol-Adenine-GalNAc, as depicted below.

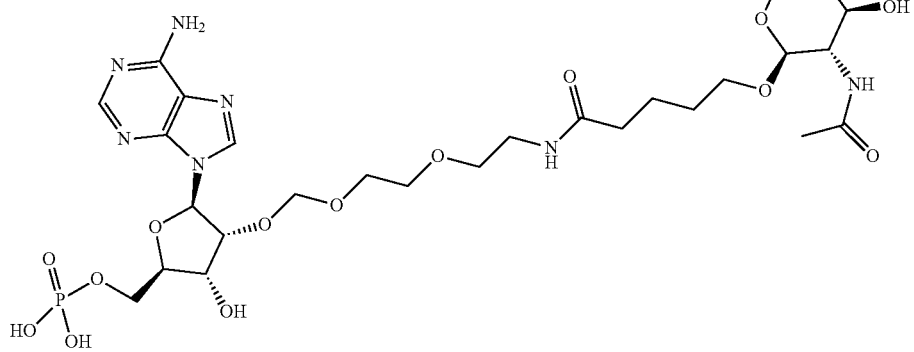

An example of such conjugation is shown below for a loop comprising from 5' to 3' the nucleotide sequence GAAA (L=linker, X=heteroatom) stem attachment points are shown. Such a loop may be present, for example, at positions 27-30 of the molecule shown in FIG. 1A. In the chemical formula International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable.

An example is shown below for a loop comprising from 5' to 3' the nucleotides GAAA, in which GalNac moieties are attached to nucleotides of the loop using an acetal linker. Such a loop may be present, for example, at positions 27-30 of the molecule shown in FIG. 10. In the chemical formula, is an attachment point to the oligonucleotide strand.

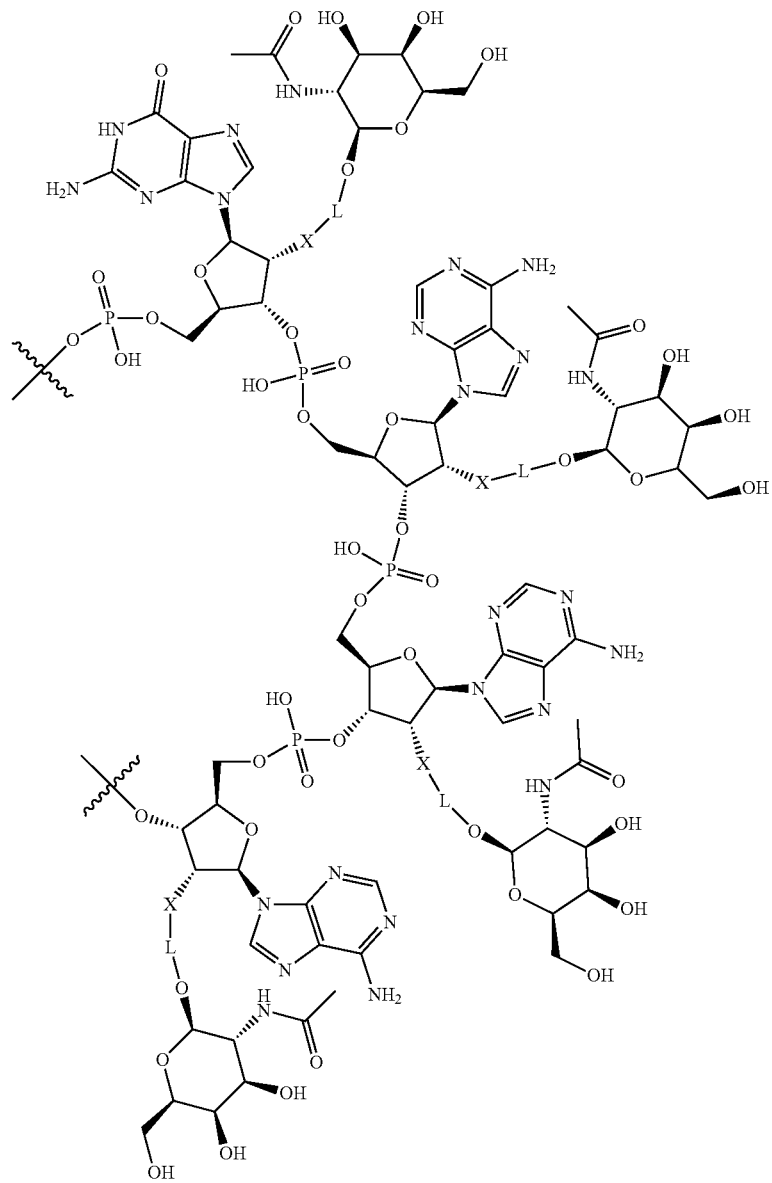

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in

is an attachment point to the oligonucleotide strand.

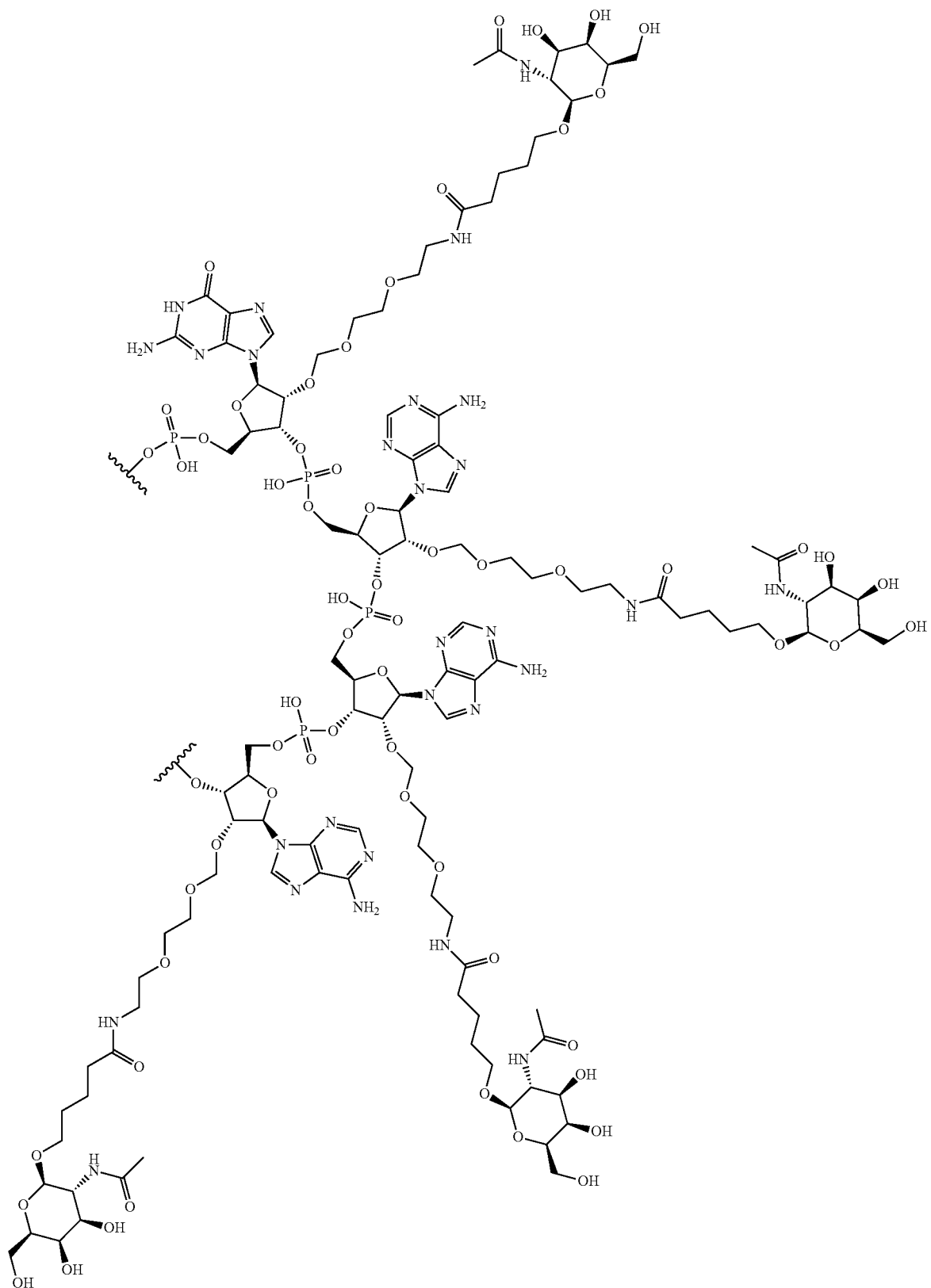 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(=O)(O)O*]

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of HBV antigen (e.g., HBsAg). Such compositions can be suitably formulated such that when administered to a subject, either into the immediate environment of a target cell or systemically, a sufficient portion of the oligonucleotides enter the cell to reduce HBV antigen expression. Any of a variety of suitable oligonucleotide formulations can be used to deliver oligonucleotides for the reduction of HBV antigen as disclosed herein. In some embodiments, an oligonucleotide is formulated in buffer solutions such as phosphate-buffered saline solutions, liposomes, micellar structures, and capsids.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., an oligonucleotide for reducing HBV antigen expression) or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing HBsAg Expression

In some embodiments, methods are provided for delivering to a cell an effective amount any one of oligonucleotides disclosed herein for purposes of reducing expression of HBsAg. Methods provided herein are useful in any appropriate cell type. In some embodiments, a cell is any cell that expresses HBV antigen (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue and skin). In some embodiments, the cell is a primary cell that has been obtained from a subject and that may have undergone a limited number of a passages, such that the cell substantially maintains its natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of HBsAg solely in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of HBV antigen expression (e.g., RNA, protein). In some embodiments, the extent to which an oligonucleotide provided herein reduces levels of expression of HBV antigen is evaluated by comparing expression levels (e.g., mRNA or protein levels) of HBV antigen to an appropriate control (e.g., a level of HBV antigen expression in a cell or population of cells to which an oligonucleotide has not been delivered or to which a negative control has been delivered). In some embodiments, an appropriate control level of HBV antigen expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of HBV antigen (e.g., HBsAg) expression in a cell. In some embodiments, the reduction in levels of HBV antigen expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of HBV antigen. The appropriate control level may be a level of HBV antigen expression in a cell or population of cells that has not been contacted with an oligonucleotide as described herein. In some embodiments, the effect of delivery of an oligonucleotide to a cell according to a method disclosed herein is assessed after a finite period of time. For example, levels of HBV antigen may be analyzed in a cell at least 8 hours, 12 hours, 18 hours, 24 hours; or at least one, two, three, four, five, six, seven, fourteen, twenty-one, twenty-eight, thirty-five, forty-two, forty-nine, fifty-six, sixty-three, seventy, seventy-seven, eighty-four, ninety-one, ninety-eight, 105, 112, 119, 126, 133, 140, or 147 days after introduction of the oligonucleotide into the cell.

In some embodiments, the reduction in the level of HBV antigen (e.g., HBsAg) expression persists for an extended period of time following administration. In some embodiments, a detectable reduction in HBsAg expression persists within a period of 7 to 70 days following administration of an oligonucleotide described herein. For example, in some embodiments, the detectable reduction persists within a period of 10 to 70, 10 to 60, 10 to 50, 10 to 40, 10 to 30, or 10 to 20 days following administration of the oligonucleotide. In some embodiments, the detectable reduction persists within a period of 20 to 70, 20 to 60, 20 to 50, 20 to 40, or 20 to 30 days following administration of the oligonucleotide. In some embodiments, the detectable reduction persists within a period of 30 to 70, 30 to 60, 30 to 50, or 30 to 40 days following administration of the oligonucleotide. In some embodiments, the detectable reduction persists within a period of 40 to 70, 40 to 60, 40 to 50, 50 to 70, 50 to 60, or 60 to 70 days following administration of the oligonucleotide.

In some embodiments, a detectable reduction in HBsAg expression persists within a period of 2 to 21 weeks following administration of an oligonucleotide described herein. For example, in some embodiments, the detectable reduction persists within a period of 2 to 20, 4 to 20, 6 to 20, 8 to 20, 10 to 20, 12 to 20, 14 to 20, 16 to 20, or 18 to 20 weeks following administration of the oligonucleotide. In some embodiments, the detectable reduction persists within a period of 2 to 16, 4 to 16, 6 to 16, 8 to 16, 10 to 16, 12 to 16, or 14 to 16 weeks following administration of the oligonucleotide. In some embodiments, the detectable reduction persists within a period of 2 to 12, 4 to 12, 6 to 12, 8 to 12, or 10 to 12 weeks following administration of the oligonucleotide. In some embodiments, the detectable reduction persists within a period of 2 to 10, 4 to 10, 6 to 10, or 8 to 10 weeks following administration of the oligonucleotide.

In some embodiments, an oligonucleotide is delivered in the form of a transgene that is engineered to express in a cell the oligonucleotides (e.g., its sense and antisense strands). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing HBsAg expression (e.g., reducing HBsAg expression) for the treatment of HBV infection in a subject. In some embodiments, the methods may comprise administering to a subject in need thereof an effective amount of any one of the oligonucleotides disclosed herein. The present disclosure provides for both prophylactic and therapeutic methods of treating a subject at risk of (or susceptible to) HBV infection and/or a disease or disorder associated with HBV infection.

In certain aspects, the disclosure provides a method for preventing in a subject, a disease or disorder as described herein by administering to the subject a therapeutic agent (e.g., an oligonucleotide or vector or transgene encoding same). In some embodiments, the subject to be treated is a subject who will benefit therapeutically from a reduction in the amount of HBsAg protein, e.g., in the liver. Subjects at risk for the disease or disorder can be identified by, for example, one or a combination of diagnostic or prognostic assays known in the art (e.g., identification of liver cirrhosis and/or liver inflammation). Administration of a prophylactic agent can occur prior to the detection of or the manifestation of symptoms characteristic of the disease or disorder, such that the disease or disorder is prevented or, alternatively, delayed in its progression.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently. For example, the dosage can be in the range of 0.1 mg/kg to 12 mg/kg. The dosage could also be in the range of 0.5 to 10 mg/kg. Alternatively, the dosage can be in the range of 1.0 to 6.0 mg/kg. The dosage could also be in the range of 3.0 to 5.0 mg/kg.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

As a non-limiting set of examples, the oligonucleotides of the instant disclosure would typically be administered quarterly (once every three months), bi-monthly (once every two months), monthly, or weekly. For example, the oligonucleotides may be administered every one, two, or three weeks. The oligonucleotides may be administered daily.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Example 1. Development of Potent Oligonucleotide Inhibitors of HBsAg Expression

HBV surface antigen was identified as a target for RNAi-based therapy to treat HBV infection. As depicted in the HBV genome organization shown in FIG. 1, HBsAg is encoded by three RNA molecules transcribed from a single ORF. Oligonucleotides were designed for purposes of silencing one or more RNA transcripts that contribute to HBsAg assembly (example RNAi target site indicated by "X" in FIG. 1). An HBsAg-targeting oligonucleotide, HBV-254, was designed and evaluated in vitro and in vivo. HBV-254 was selected and designed based on an ability to directly target mRNA transcripts for four HBV RNA species. The HBV-254 duplex oligonucleotide used in the experiments included a sense strand of a sequence as set forth in (shown 5' to 3'): GUGGUGGACUUCUCU-CAAUAGCAGCCGAAAGGCUGC (SEQ ID NO: 23); and an antisense strand of a sequence as set forth in (shown 5' to 3'): UAUUGAGAGAAGUCCACCACGG (SEQ ID NO: 24).

Each oligonucleotide, including HBV-254, was evaluated at three concentrations (1, 10, and 100 pM) in HeLa cells using the fluorescence-based reporter assay. The results reported for each plate are further shown in comparison with positive control (8, 40, and 200 pM), negative control (1 nM), and mock transfection. Oligonucleotides shown highlighted with boxes were scaled up for in vivo testing, in which HBV-219 and HBV-258 were found to be the most potent oligonucleotides among HBV-254 and those identified from the screening. HBV-219 exhibited a multi-log improvement in potency over HBV-254 and was selected for additional evaluation.

Example 2. Sequence Conservation Analysis and Engineering Mismatches to Increase Global Therapeutic Utility Several of the most potent oligonucleotides evaluated in Example 1 were compared against genome sequences for HBV genotypes A-I. The results of an initial conservation analysis are listed in Table 1. As shown, HBV-219 has relatively low percent conservation across these genomes. However, percent conservation increases significantly (from 66% to 96%) if a mismatch (MM) is introduced at position 15 of the guide strand. Genotyped hepatitis B virus (HBV) sequence data from the GenBank public database, incorporated herein by reference, was used for bioinformatics curation and alignment.

TABLE 1

Initial conservation analysis with top HBV sequences

| Oligonucleotide | Guide Strand with MM in bold | % conservation across genomes | % conservation if MM is tolerated |
|---|---|---|---|
| HBV-0217 | UUUGUGAGGAUUUUGUCAAGG (SEQ ID NO: 25) | 66 | 97 |
| HBV-0219 | UUAUUGUGAGGAUUUUUGUCGG (SEQ ID NO: 6) | 66 | 96 |
| HBV-0254 | UCUGAGAGAAGUCCACCACGGG (SEQ ID NO: 26) | 94 | 98 |
| HBV-0255 | UACUGAGAGAAGUCCACCACGG (SEQ ID NO: 27) | 95 | 99 |
| HBV-0258 | UAAAACUGAGAGAAGUCCACGG (SEQ ID NO: 28) | 94 | 98 |

Figure 2:
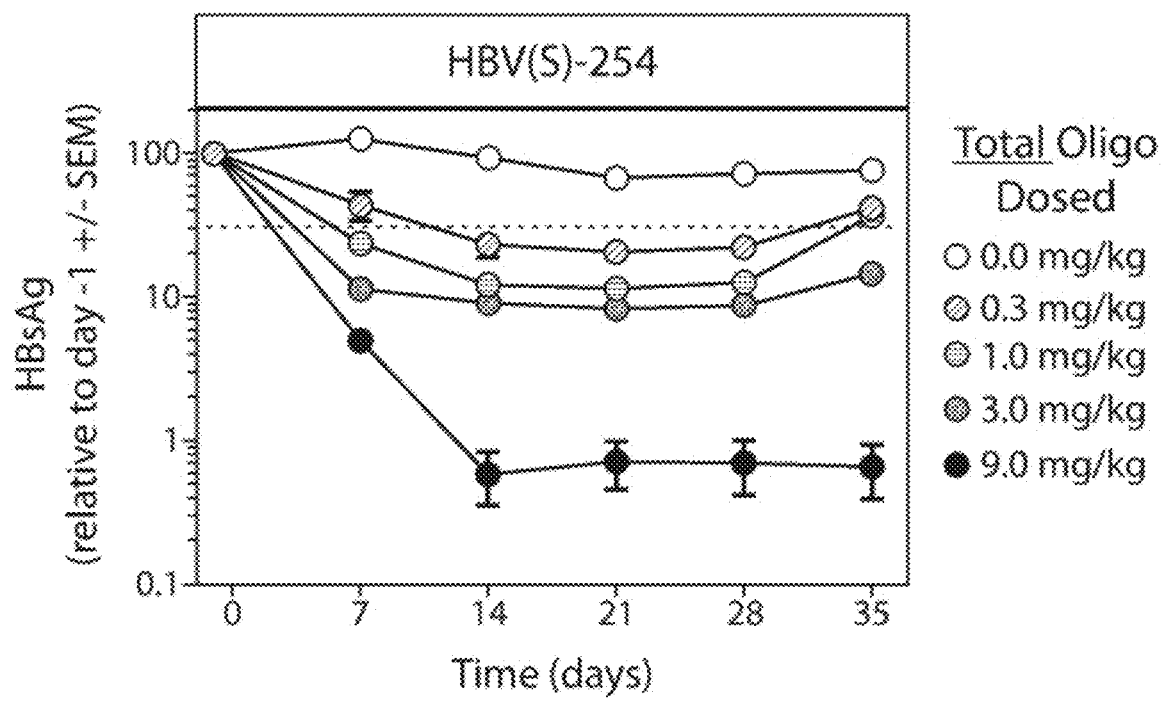
FIG. 2 shows single dose evaluation of an oligonucleotide for reducing HBsAg expression in HDI-mice.
Figure 3:
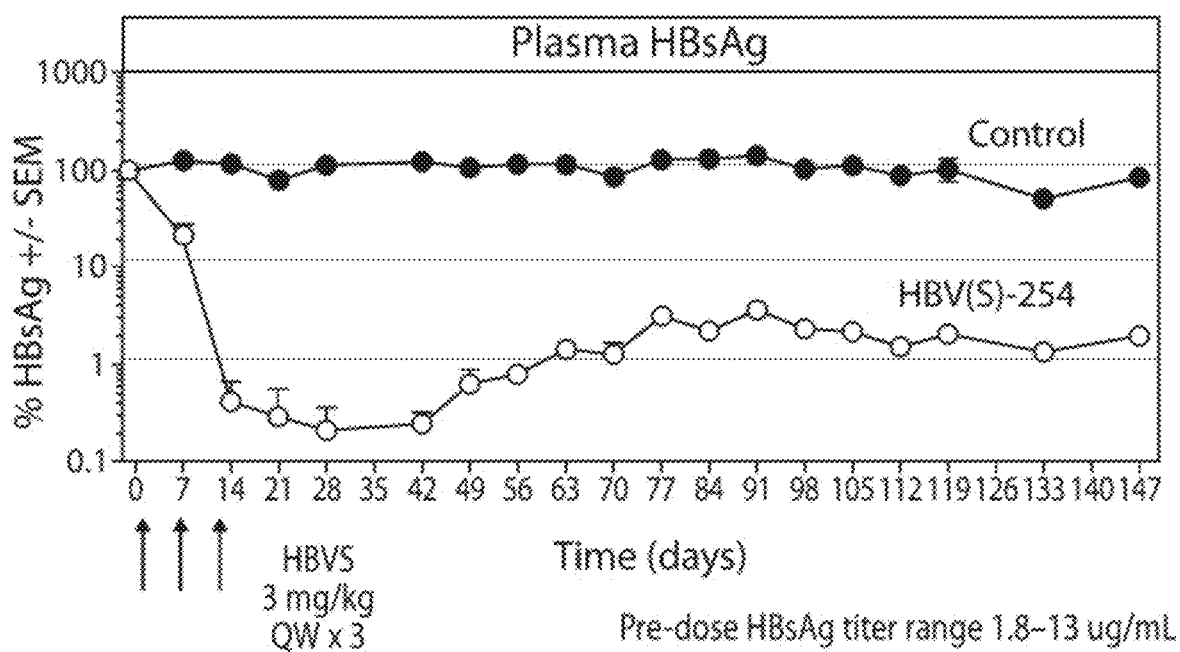
FIG. 3 is a graphical representation of plasma HBsAg levels over time during a specified dosing regimen with an HBsAg-targeting oligonucleotide. As shown in this example, the oligonucleotide demonstrated preclinical potency and maintained decreased levels well beyond the dosing period.

A single dose evaluation of oligonucleotide HBV-254 in HDI-mice was conducted, demonstrating the ability to subcutaneously target HBsAg viral transcript (FIG. 2). As shown, HBV-254 systematically reduced HBsAg levels in mice with increasing dosage. Preclinical potency was further evaluated in mice following a QW×3 dosing regimen in which HBV-254 was subcutaneously administered at 3 mg/kg (FIG. 3). The administration points are indicated by arrows in the figure. HBsAg levels were monitored in both oligonucleotide treated and untreated control mice for a period spanning 147 days. Diminished HBsAg levels persisted in treated mice throughout the entirety of the study, with expression levels (relative to control) appearing to settle at a reduced baseline at approximately two months following the first administration.

Figure 4:
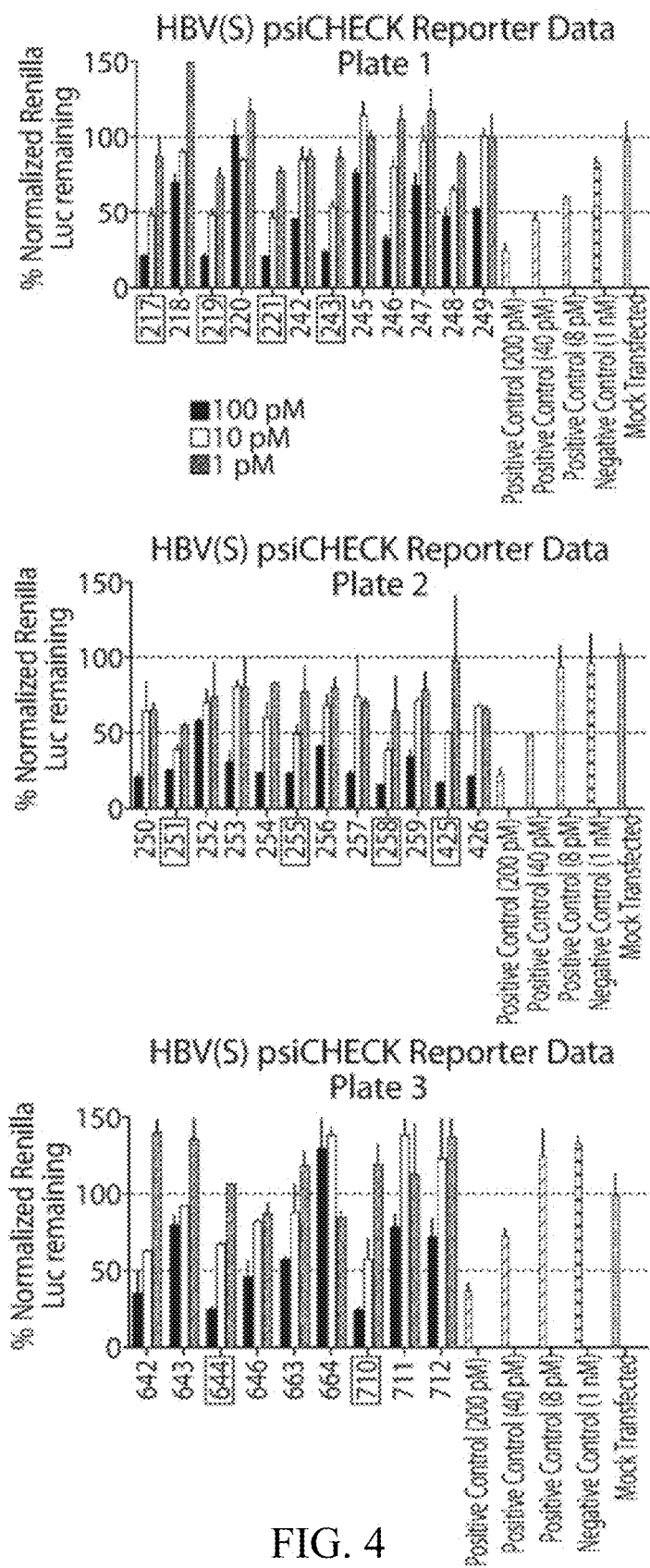
FIG. 4 shows graphs depicting the results of HBsAg mapping in HeLa cells using a reporter assay. An unmodified siRNA targeting position 254 of the HBV genome was used as a positive control at the specified concentrations. A commercially available Silencer siRNA from Thermo Fisher served as the negative control for these experiments. Error bars represent the SEM.

Additional potent HBsAg-targeting oligonucleotides were identified by in vitro screening using a psiCHECK reporter assay with oligonucleotides in unmodified tetraloop form. The results from three different plates are shown in FIG. 4.

Figure 5:
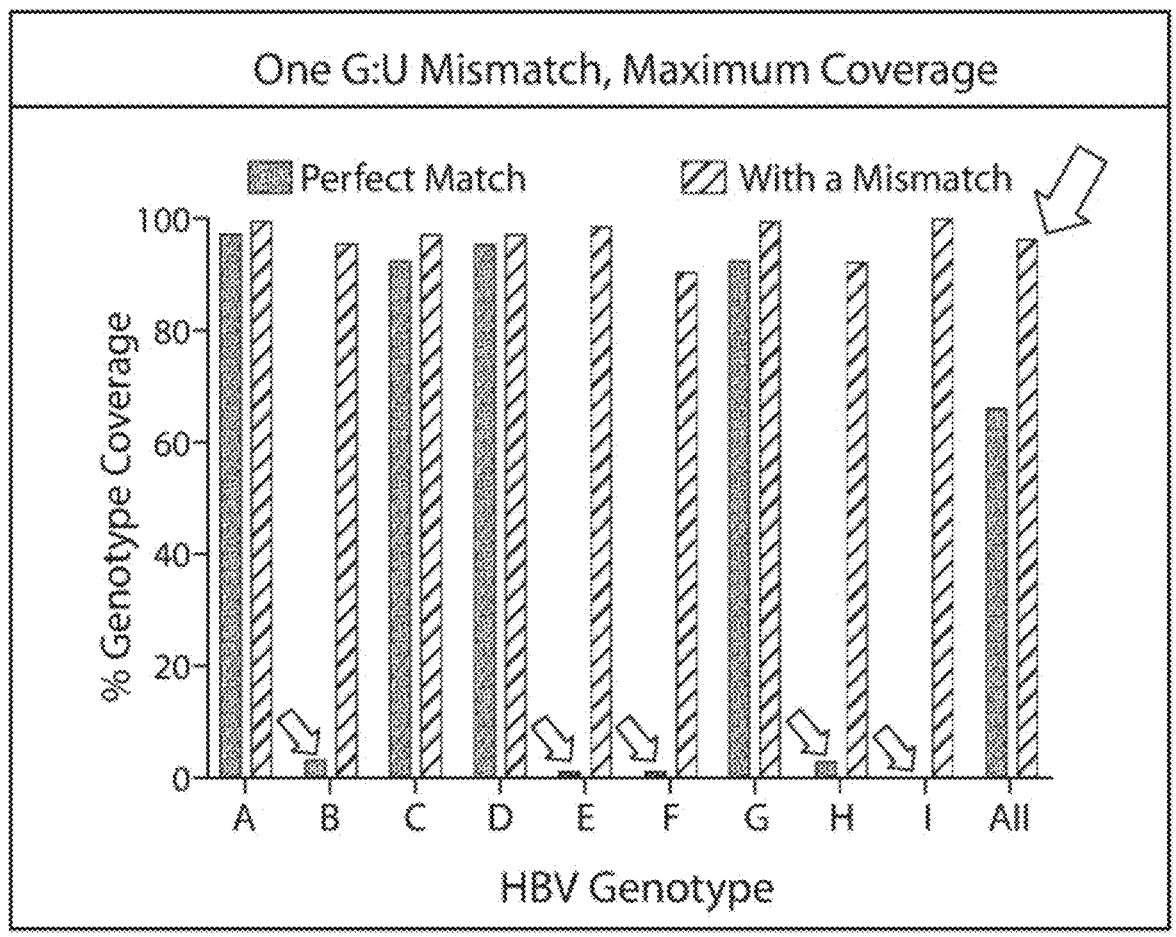
FIG. 5 shows a genotype conservation comparison showing that the designed mismatch in the HBsAg-targeting oligonucleotide, HBV-219, increases coverage across HBV genotypes.

A subsequent conservation analysis was undertaken, which focused on several of the oligonucleotides from Table 1 and involved broader searching parameters. For example, whereas the initial analysis included only full-length genome sequences, the focused analysis included full-length and partial (>80% identity to target site) sequences. Additionally, the number of genomes examined increased from 5,628 in the initial analysis to more than 17,000 genomes in the focused analysis. Results from the focused analysis were in general agreement with the trends observed in the initial analysis (FIG. 20). As shown—and further illustrated in FIG. 5—HBV-219 was predicted to be inactive against HBV genotypes B, E, F, H, and I unless mismatch at position 15 of the guide strand is tolerated.

Figure 6:
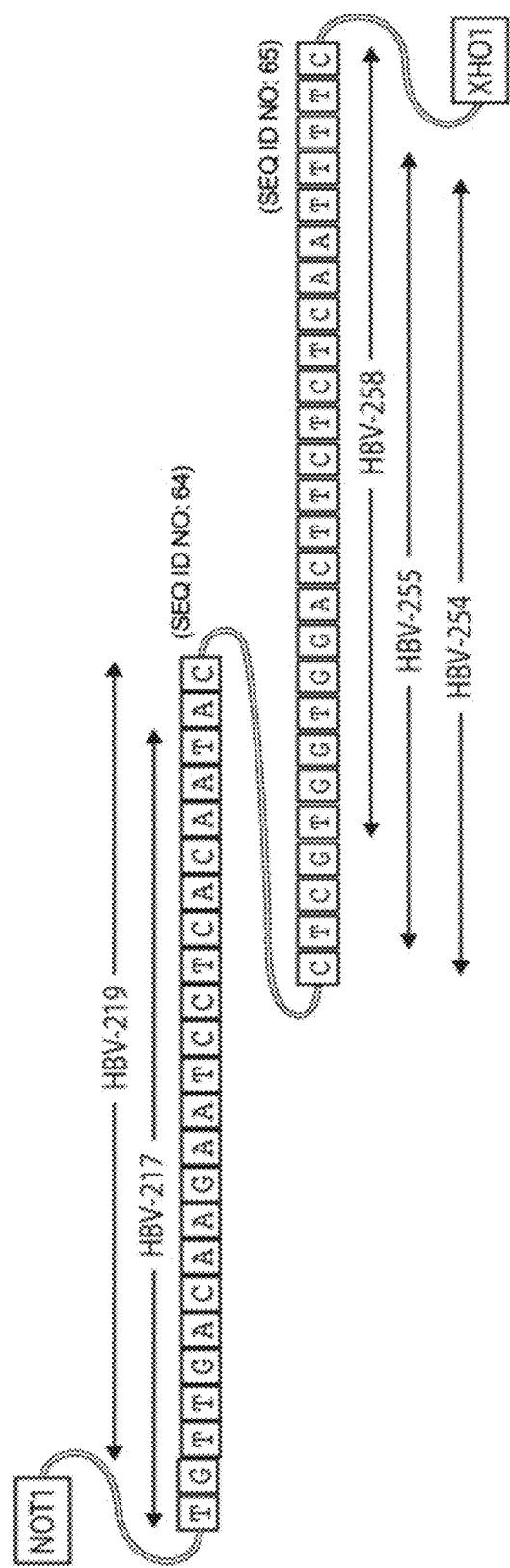
FIG. 6 illustrates a vector designed for psiCHECK2 reporter assays using HBV Genotype A as a prototype sequence.
Figure 7:
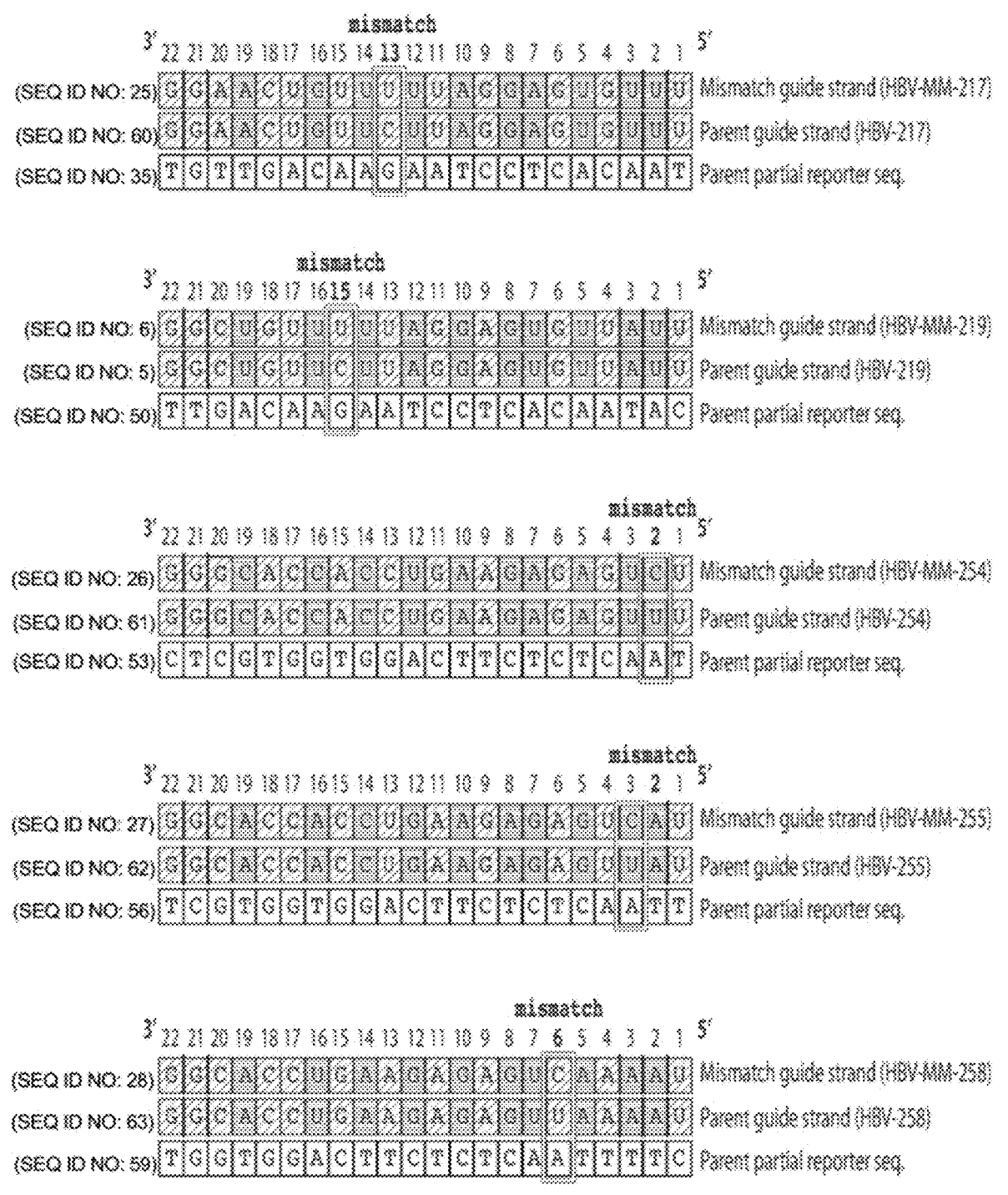

A psiCHECK-2 dual-luciferase reporter system was utilized to evaluate the effects of a mismatch at a selected position in each of HBV-217, HBV-219, HBV-254, HBV-255, and HBV-258. The psiCHECK vector enables monitoring of changes in expression of a target gene fused to a reporter gene, where active RNAi degrades the fusion construct to produce a corresponding decrease in reporter signal. The diagram in FIG. 6 generically depicts the vector utilized in these assays. The parent partial reporter sequence contained 120 base-pair fragments from Genotype A (GenBank: AM282986.1) around target sites of interest in the S ORF. Parent oligonucleotide duplex sequences have 100% homology to the reporter plasmid at corresponding sites shown in FIG. 6, whereas the mismatch oligonucleotide duplex sequences have a single mismatch to the reporter plasmid. Parent and mismatch sequences for the oligonucleotides tested are shown in FIG. 7 aligned to corresponding parent partial reporter sequences.

plate back and forth. The cells were then incubated at 37° C. in a CO2 incubator until the cells were ready to harvest and assay for the target gene. On day 3, 100 µl of Dual-Glo Reagent was added to each well, mixed and incubated for 10 minutes before reading the luminescence. A further 100 µL of Dual-Glo Stop & Glo was added to each well, mixed and incubated for 10 minutes before reading the luminescence. Dose-response curves were generated for each parent and mismatch oligonucleotide to evaluate the effects of mismatches on activity. The $EC_{50}$s values determined for each oligonucleotide are shown in Table 3 with additional specifications.

TABLE 3

Mismatch Evaluation of HBsAg-targeting oligonucleotides

| | HBV-217 | HBV-219 | HBV-254 | HBV-255 | HBV-258 |
|---|---|---|---|---|---|
| ORF Target | S | S | S | S | S |
| Sense 19-mer | TGTTGACAAGA ATCCTCACAAT (SEQ ID NO: 35) | GACAAGAATC CTCACAATA (SEQ ID NO: 29) | CGTGGTGGAC TTCTCTCAA (SEQ ID NO: 30) | TCGTGGTGGAC TTCTCTCAAT (SEQ ID NO: 36) | GTGGACTTCT CTCAATTTT (SEQ ID NO: 31) |
| Sense 19-mer w/ambiguous Base | TGTTGACAANA ATCCTCACAAT (SEQ ID NO: 37) | GACAANAATC CTCACAATA (SEQ ID NO: 32) | CGTGGTGGAC TTCTCTCAN (SEQ ID NO: 33) | TCGTGGTGGAC TTCTCTCANT (SEQ ID NO: 38) | GTGGACTTCT CTCANTTTT (SEQ ID NO: 34) |
| Guide Position of Mismatch | 13 | 15 | 2 | 3 | 6 |
| Parent $EC_{50}$s (pM) | 20 | 5 | 37 | 35 | 10 |
| MM $EC_{50}$s (PM) | 25 | 8 | 96 | 366 | >1000 |

For the example mismatch assays, the tested oligonucleotides included the same modification patterns. According to the numbering scheme shown for each oligonucleotide in FIG. 7, modifications were as follows: 5'-Methoxy, Phosphonate-4'-oxy-2'-O-methyluridine at position 1; 2'-fluoro modified nucleotides at positions 2, 3, 5, 7, 8, 10, 12, 14, 16, and 19; 2'-O-methyl modified nucleotides at positions 1, 4, 6, 9, 11, 13, 15, 17, 18, and 20-22; and phosphorothioate internucleotide linkages between nucleotides at positions 1 and 2, 2 and 3, 3 and 4, 20 and 21, and 21 and 22. Mismatched positions were different for each parent and mismatch set, and are shown in boxes in FIG. 7.

Figure 8:
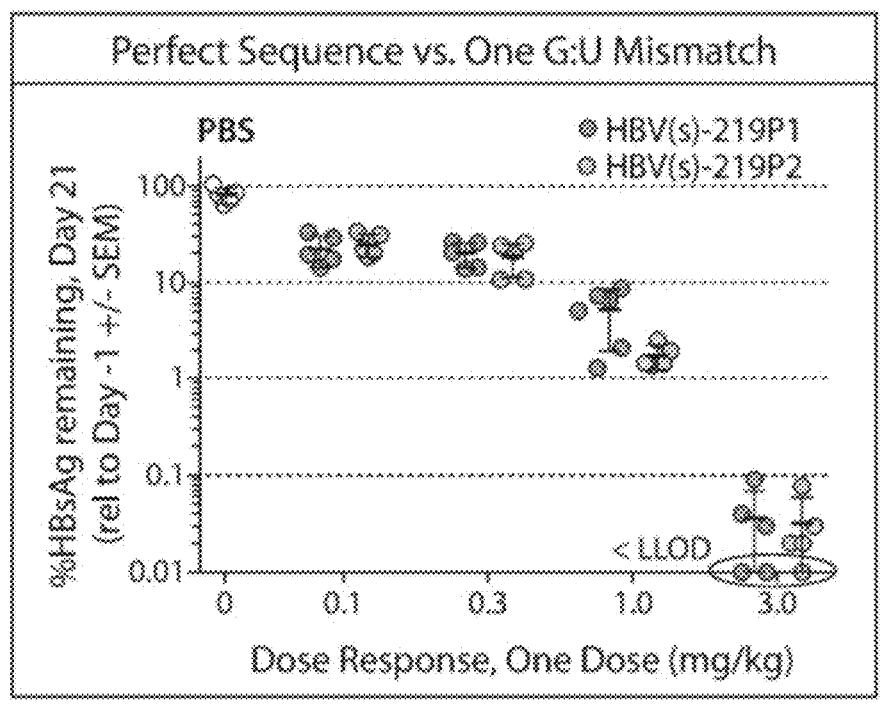
FIG. 8 shows a single-dose titration plot for an oligonucleotide evaluated in mismatch studies, which demonstrates that a mismatch in the guide strand is tolerated in vivo.
Figure 9:
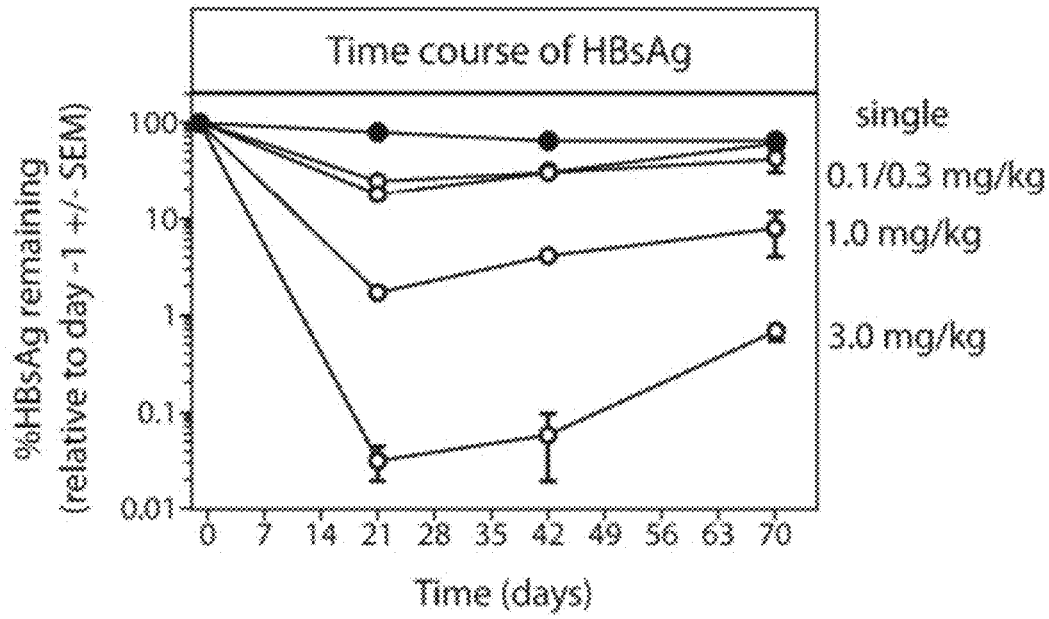
FIG. 9 shows an in vivo dose titration plot demonstrating that incorporation of a mismatch into an HBsAg-targeting oligonucleotide does not adversely affect in vivo potency.

The psiCHECK2 reporter assays with each oligonucleotide were conducted over a three-day period using a 6-point, 5-fold serial dilution starting at 1 nM transfected in HeLa cells. On day 1, 10,000 HeLa cells/well (96-well) were seeded in a black-walled, clear bottom plate (80-90% confluent). On day 2, vector DNA and RNAi molecule were diluted in the appropriate amount of Opti-MEMO I Medium without serum and gently mixed. After gently mixing Lipofectamine® 2000, 0.2 µL were diluted into 25 µL of Opti-MEMO I Medium without serum for each reaction. The dilution was mixed gently and incubated for 5 minutes at room temperature. After the 5 minute incubation, equal volumes of the diluted DNA and RNAi molecule were combined with the diluted Lipofectamine® 2000. The combined mixture was mixed gently and incubated for 20 minutes at room temperature to allow complex formation to occur. Following this, the DNA-RNAi molecule-Lipofectamine® 2000 complexes were added to each well containing cells and medium and mixed gently by rocking the As demonstrated by the relative $EC_{50}$s values, the in vitro dose-response curves for HBV-219 duplexes showed no loss of activity with a single mismatch at position 15 of the guide strand. Subsequent in vivo analysis comparing HBV-219 parent (herein designated HBV(s)-219P1) and mismatch oligonucleotides (herein designated HBV(s)-219P2) confirmed that the introduction of the mismatch produced no loss of activity (FIG. 8). As shown in the single-dose titration plot depicted in FIG. 9, the HBV-219 mismatch oligonucleotide duplex (HBV(s)-219P2) was tolerated in vivo over a 70-day period following administration.

Figure 10:
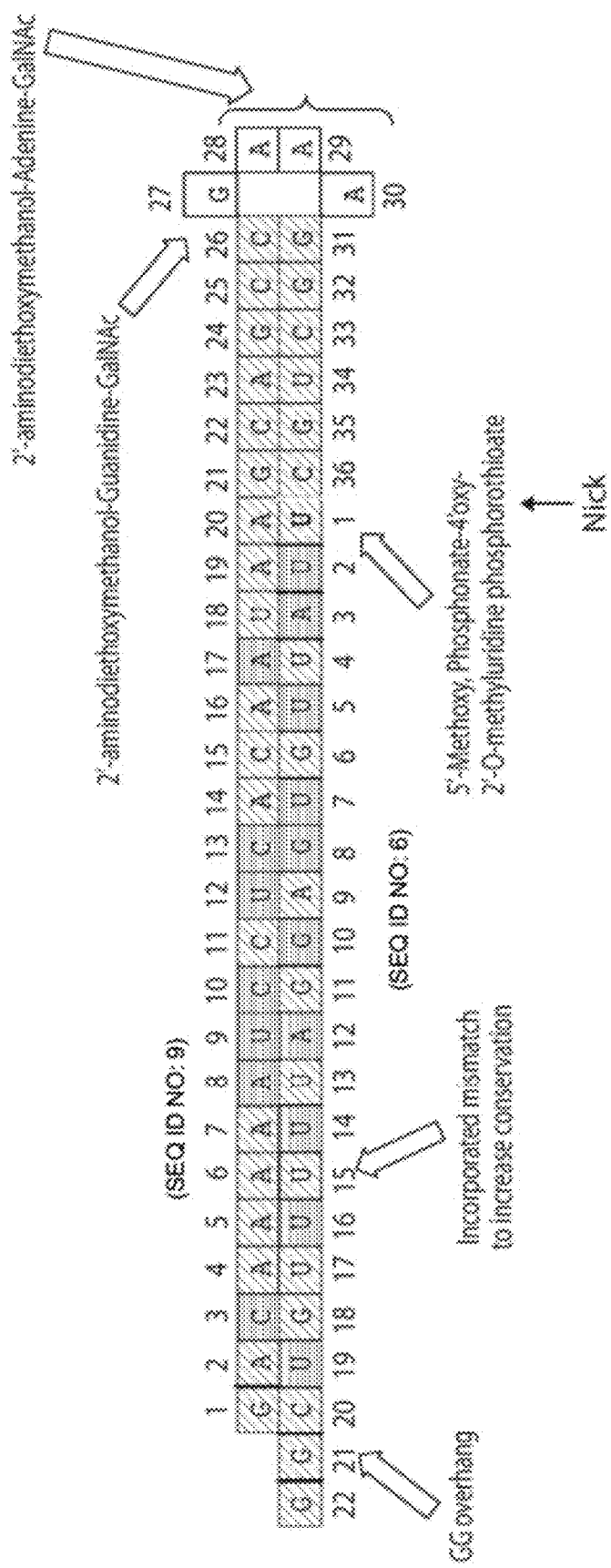
FIG. 10 shows an example of an HBsAg-targeting oligonucleotide (HBV(s)-219) with chemical modifications and in duplex form. Darker shade indicates 2'-O-methyl ribonucleotide. Lighter shade indicates 2'-fluoro-deoxyribonucleotide.

FIG. 10 illustrates an example of a modified duplex structure for HBV-219 with the incorporated mismatch (herein designated HBV(s)-219). According to the numbering scheme shown for each oligonucleotide in FIG. 7, the sense strand spans nucleotides 1 through 36 and the antisense strand spans oligonucleotides 1 through 22, the latter strand shown numbered in right-to-left orientation. The duplex form is shown with a nick between nucleotides at position 36 in the sense strand and position 1 in the antisense strand. Modifications in the sense strand were as follows: 2'-fluoro modified nucleotides at positions 3, 8-10, 12, 13, and 17; 2'-O-methyl modified nucleotides at positions 1, 2, 4-7, 11, 14-16, 18-26, and 31-36; a phosphorothioate internucleotide linkage between nucleotides at positions 1 and 2; 2'-OH nucleotides at positions 27-30; a 2'-aminodiethoxymethanol-Guanidine-GalNAc at position 27; and a 2'-aminodiethoxymethanol-Adenine-GalNAc at each of positions 28, 29, and 30. Modifications in the antisense strand were as follows: 5'-Methoxy, Phosphonate-4'-oxy-2'-O-methyluridine phosphorothioate at position 1; 2'-fluoro modified nucleotides at positions 2, 3, 5, 7, 8, 10, 12, 14, 16, and 19; 2'-O-methyl modified nucleotides at positions 1, 4, 6, 9, 11, 13, 15, 17, 18, and 20-22; and phosphorothioate internucleotide linkages between nucleotides at positions 1 and 2, 2 and 3, 3 and 4, 20 and 21, and 21 and 22. The antisense strand included an incorporated mismatch at position 15. Also as shown, the antisense strand of the duplex included a "GG" overhang spanning positions 21-22.

The details about HBV(s)-219 and the two precursors referred to above (HBV(s)-219P1 and HBV(s)-219P2) are shown in Table 4.

TABLE 4

HBV(s)-219 and precursors

| RNAi oligonucleotides | Length (sense/antisense) | Sequence/Chemical Modifications |
|---|---|---|
| HBV(s)-219 | 36/22 mer | Contains mismatch at position 15 of antisense strand. An acetal based GalNAc linker is used. Methoxy, Phosphonate-4'oxy-2'-O-methyluridine (MeMOP) is used at position 1 of antisense strand. See FIG. 10 and FIG. 19A |
| HBV(s)-219P2 | 36/22 mer | Contains mismatch at position 15 of antisense strand. A click chemistry based conjugation incorporates a triazole based GalNAc linker. Fully deprotected 5'-Phosphonate-4'oxy-2'-O-methyluridine (MOP) is used at position 1 of antisense strand. See FIG. 19B |
| HBV(s)-219P1 | 36/22 mer | Does not contain the mismatch at position 15 of antisense strand. Same chemical modifications as HBV(s)-219P2. |

Example 3: Antiviral Activity of HBV(s)-219 Precursors

The effects of treatment with the HBV(s)-219 precursors on the subcellular localization of HBV core antigen (HBcAg) were evaluated. $NOD_{scid}$ mice were subjected to a hydrodynamic injection (HDI) of a head-tail dimer of HBV genome. Treatment with the oligonucleotide was initiated 2 weeks post-HDI. Immunohistochemical staining of hepatocytes isolated from the mice following treatment showed a sharp reduction in HBV core antigen (HBcAg) expression.

Figure 11A:
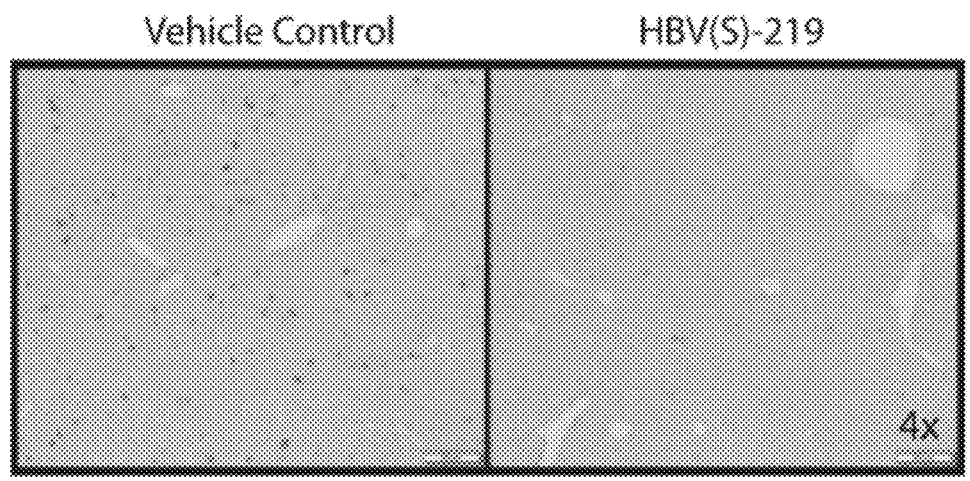
FIG. 11A depicts immunohistochemical staining results detecting the subcellular distribution of HBV core antigen (HBcAg) in hepatocytes.
Figure 11B:
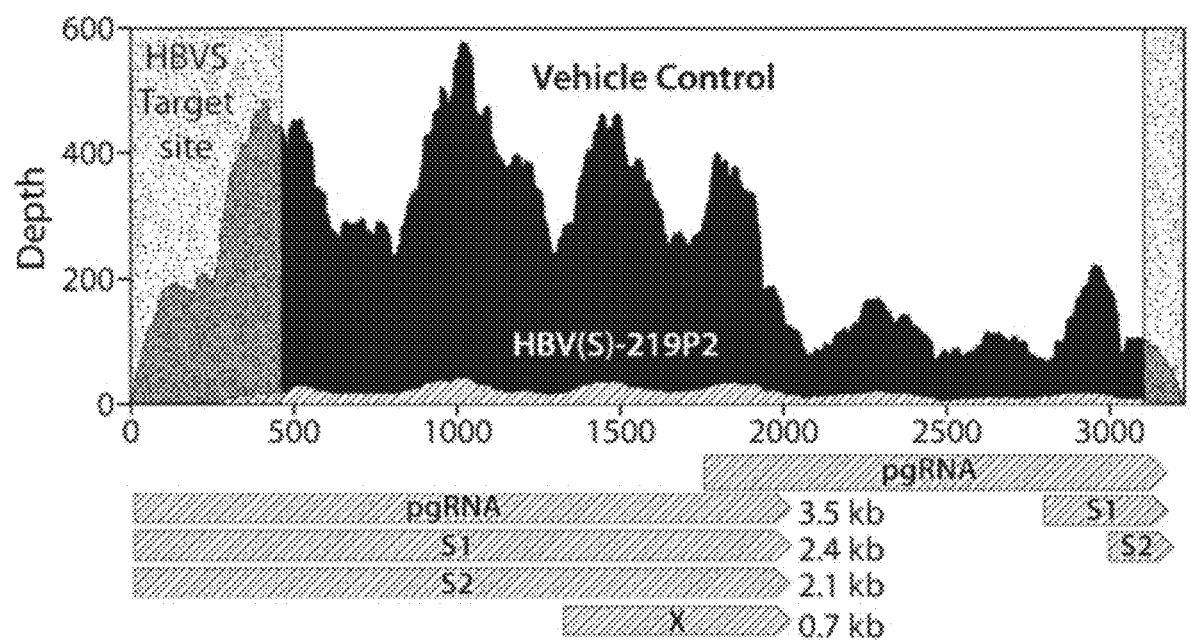
FIG. 11B depicts RNA sequencing results mapping detected RNA transcript sequences against the HBV pgRNA.

RNA sequencing was performed to examine the effects of HBsAg knockdown on overall expression of HBV viral transcripts. Hepatocytes were isolated from HDI mice four days following three, once-weekly doses at 3 mg/kg each. Total RNA was extracted from the hepatocytes and subjected to Illumina sequencing using the HiSeq Platform. FIG. 11B depicts RNA sequencing results in which detected RNA transcript sequences were mapped against the HBV RNAs. The target site of the HBV(s)-219 and its precursors is also depicted, showing that the oligonucleotide targets pgRNA (3.5 kb), S1 (2.4 kb), and S2 (2.1 kb) transcripts. The results show that, compared with vehicle controls, treatment with the HBV(s)-219P1 resulted in greater than 90% silencing of all HBV viral transcripts.

Figure 12A:
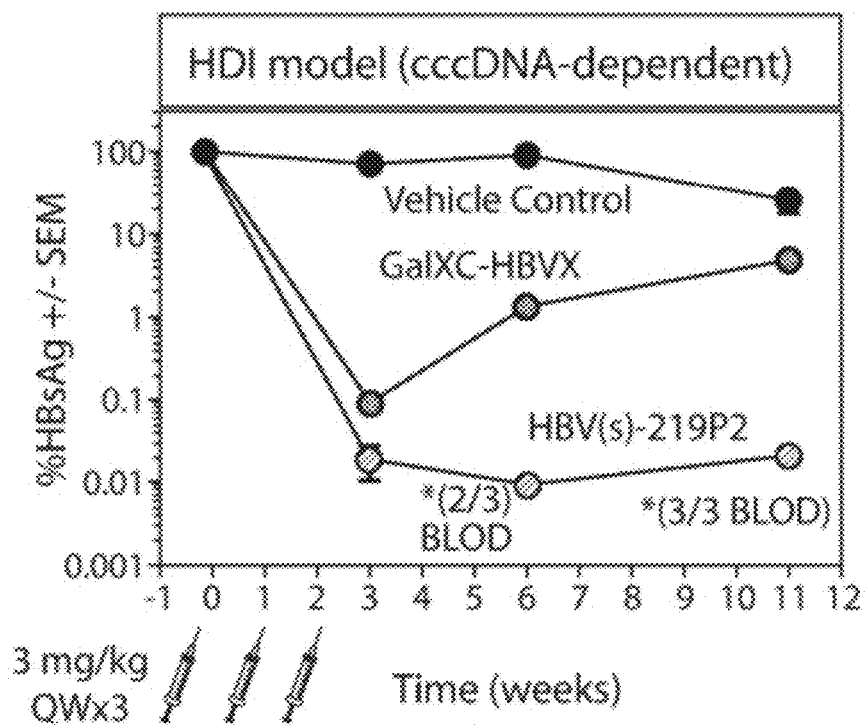
FIG. 12A depicts a time course of HBsAg mRNA expression following treatment with the HBV(s)-219 oligonucleotide precursor HBV(s)-219P2 targeting HBsAg mRNA compared with vehicle control and an RNAi oligonucleotide targeting HBxAg mRNA in a hydrodynamic injection (HDI) model of HBV.

The durational effects of the HBV(s)-219P1 oligonucleotide were examined in two different mouse models of HBV—an HDI model, which is cccDNA-dependent, and an AAV model, which is cccDNA independent. A time course (12 weeks) analysis of HBsAg mRNA expression was performed in the context of a treatment involving three once-weekly doses of 3 mg/kg with the HBV(s)-219P1 oligonucleotide targeting HBsAg mRNA compared with vehicle control and an RNAi oligonucleotide targeting HBxAg mRNA in the HDI model of HBV (FIG. 12A). The HBV(s)-219P1 oligonucleotide produced a ≥3.9 log reduction, with a relatively long duration of activity persisting for greater than 7 weeks; whereas by comparison an HBV(x) targeting oligonucleotide produced about a 3.0 log reduction, that persisted for a shorter duration.

Figure 12B:
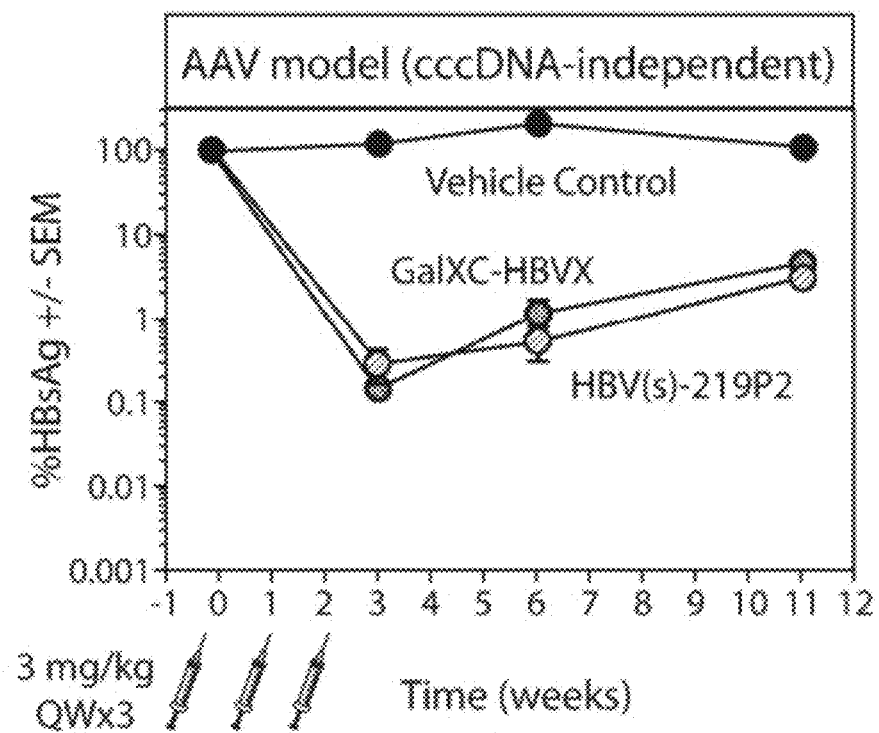
FIG. 12B depicts a time course of HBsAg mRNA expression following treatment with the HBV(s)-219 oligonucleotide precursor HBV(s)-219P2 targeting HBsAg mRNA compared with vehicle control and an RNAi oligonucleotide targeting HBxAg mRNA in an AAV-HBV model.

A further time course (12 weeks) analysis of HBsAg mRNA expression was performed in the context of a treatment involving three once-weekly doses of 3 mg/kg with the HBV(s)-219P2 oligonucleotide targeting HBsAg mRNA compared with vehicle control and an RNAi oligonucleotide targeting HBxAg mRNA in an AAV-HBV model (FIG. 12B). In this model, the HBV(s)-219P2 oligonucleotide produced a comparable log reduction and duration as an HBV(x) targeting oligonucleotide. The RNAi oligonucleotide targeting HBxAg mRNA used in FIGS. 12A and 12B has a sense strand sequence of UGCACUUCGCGUCAC-CUCUAGCAGCCGAAAGGCUGC (SEQ ID NO: 39) and an antisense strand sequence of UAGAGGUGACG-CGAAGUGCAGG (SEQ ID NO: 40). This RNAi oligonucleotide targeting HBxAg is herein designated GalXC-HBVX.

Figure 13:
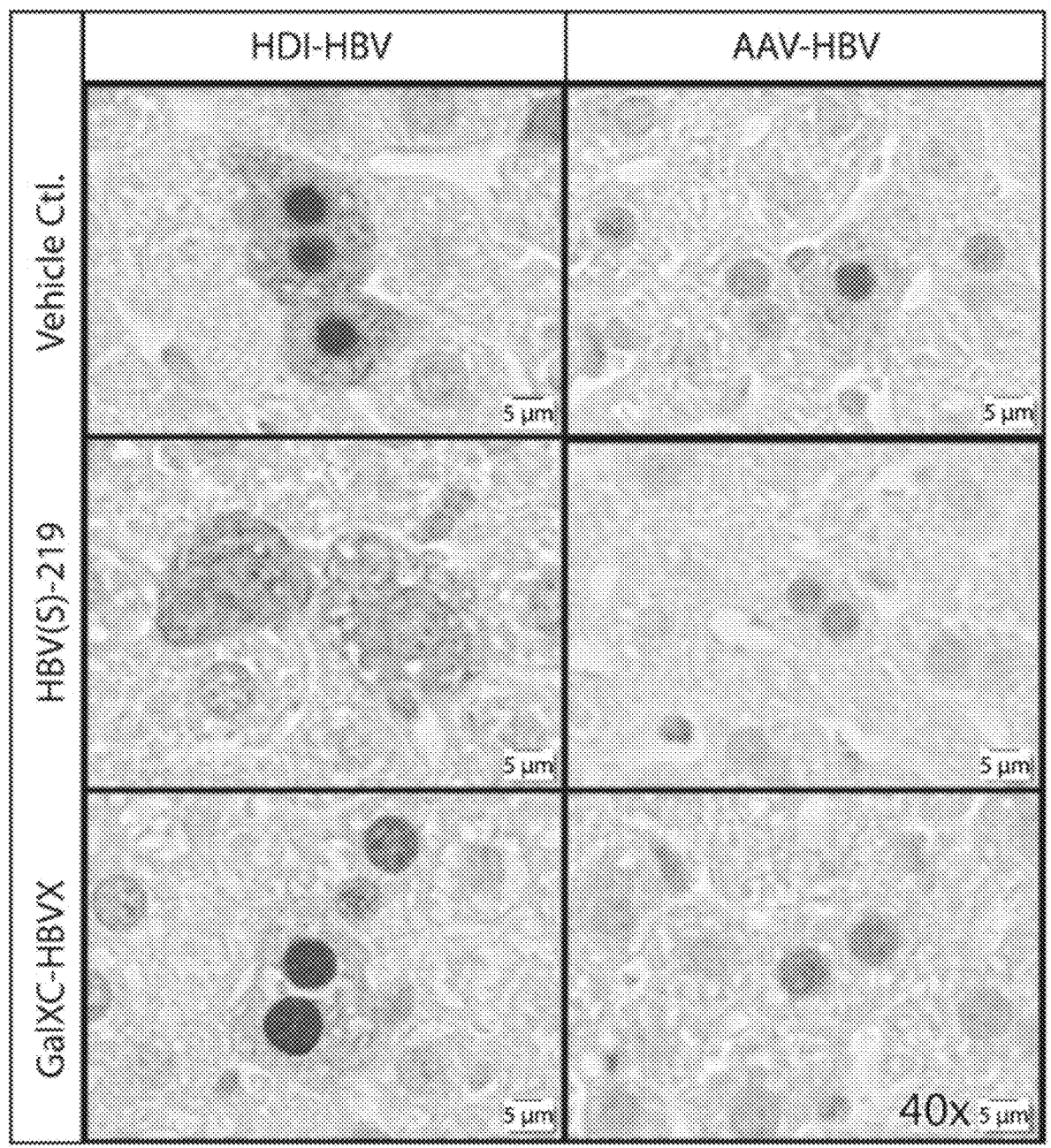
FIG. 13 shows immunohistochemical staining results showing the subcellular distribution of HBcAg in hepatocytes obtained from AAV-HBV model and HDI model of HBV following treatment with the HBV(s)-219 oligonucleotide targeting HBsAg mRNA compared with vehicle control and an RNAi oligonucleotide targeting HBxAg mRNA (GalXC-HBVX).
Figure 14A:
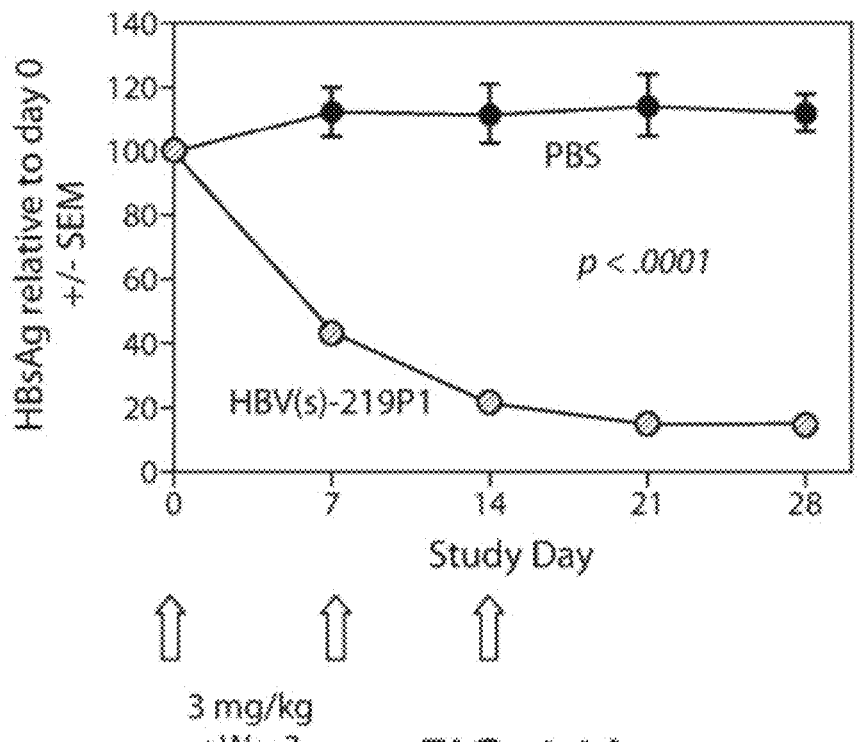
FIGS. 14A-14D show antiviral activity of HBV(s)-219 precursor 1 (HBV(s)-219 P1) in a PXB-HBV model. Cohorts of 9 mice were given 3 weekly doses of either 0 or 3 mg/kg of HBV(s)-219P1 in PBS, administered subcutaneously. Six mice from each cohort were analyzed by non-terminal mandibular cheek bleeds at each of the time points indicated (FIGS. 14A and 14B) for serum HBsAg and serum HBV DNA. At Day 28 (starting from the first dose of HBV(s)-219P1), all remaining mice were euthanized and liver biopsies were collected for hepatic HBV DNA (FIG. 14C) and hepatic cccDNA (FIG. 14D) by RT-qPCR.
Figure 14B:
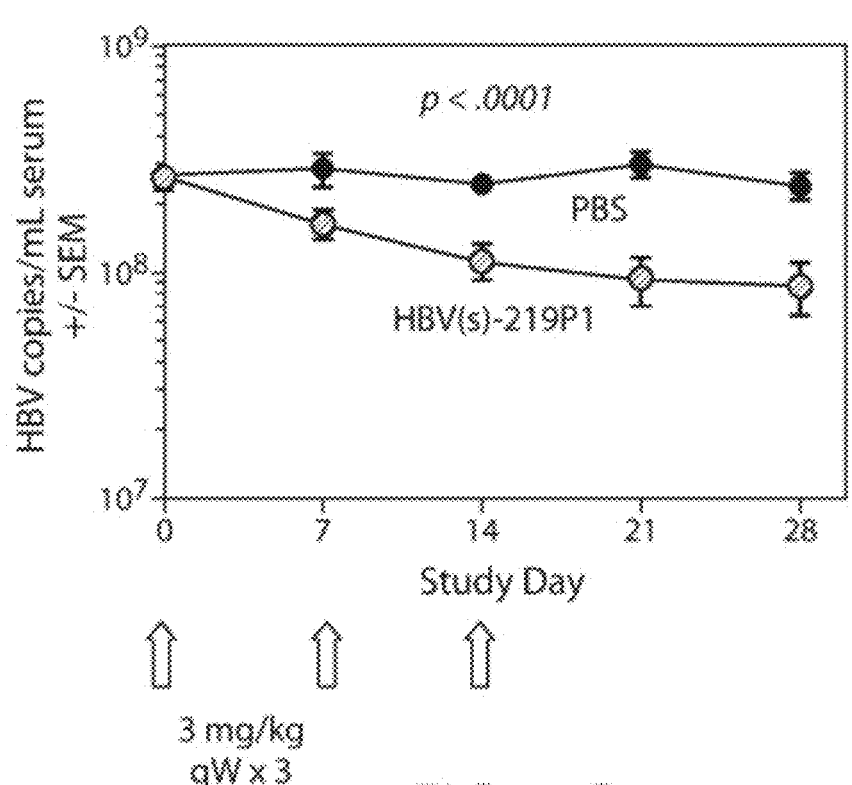
Figure 14C:
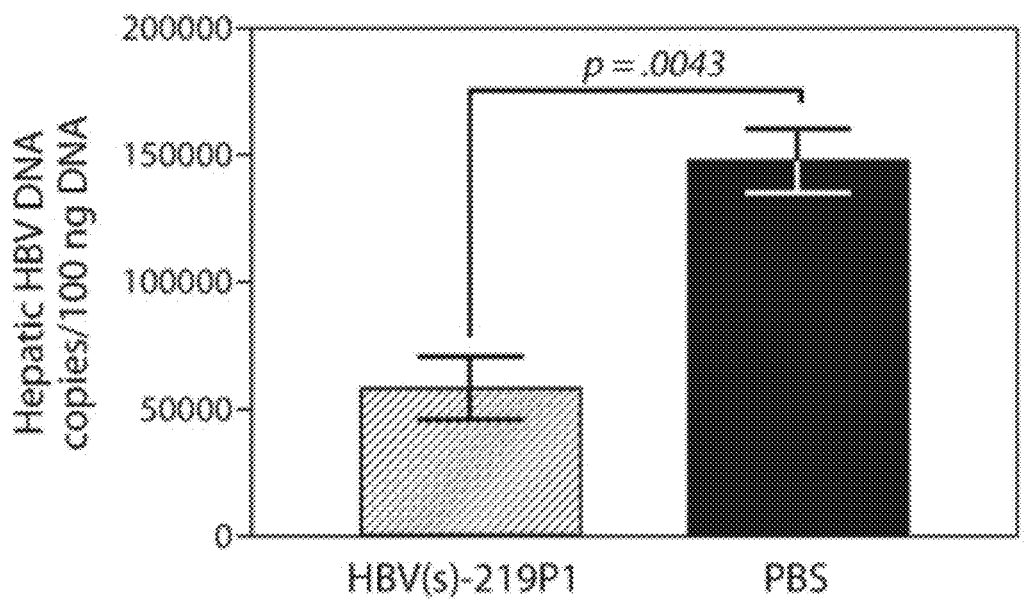
Figure 14D:
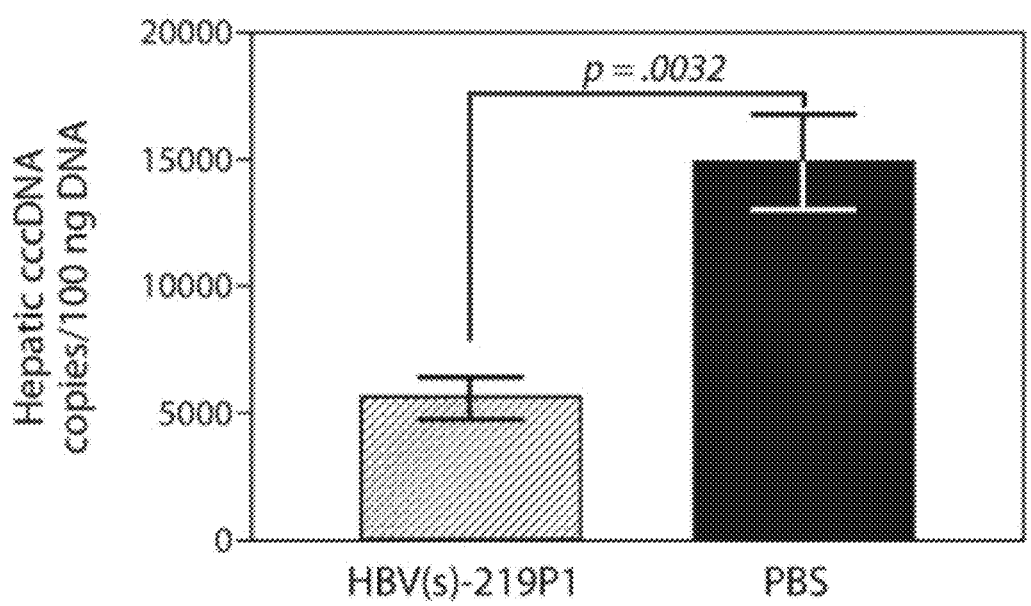

Immunohistochemical staining was performed to examine the subcellular distribution of HbcAg in hepatocytes obtained from AAV-HBV model and HDI model of HBV following treatment with the HBV(s)-219 precursor oligonucleotides as indicated above targeting HBsAg mRNA compared with vehicle control and an RNAi oligonucleotide targeting HBxAg mRNA, as described above. (FIG. 13) Residual Core protein (HBcAg) after treatment exhibited notable differences in subcellular localization between the two RNAi oligonucleotides in the HDI model, but not in AAV model.

Example 4: Evaluation of HBV(s)-219P1 in the PXB-HBV Chimeric Human Liver Model Genotype C The antiviral activity of HBV(s)-219P1 was evaluated in the PXB-HBV model, also known in the HBV literature as the chimeric human liver model. This technology is based on grafting human hepatocytes into severely immunocompromised mice, then using a genetic mechanism to poison the host murine hepatocytes (Tateno et al., 2015). This process results in mice containing livers derived from >70% human tissue, which, unlike wild type mice, can be infected with HBV (Li et al., 2014). The PXB-HBV model serves several purposes in the context of HBV(s)-219 pharmacology: (1) to confirm that the oligonucleotide can engage the human RNAi machinery (RISC) in vivo, (2) to confirm that the GalNAc-targeting ligand configuration can internalize into hepatocytes via human ASGR in vivo, and (3) to confirm efficacy in a true model of HBV infection (as opposed to an engineered model of HBV expression). Despite the limitation that the grafted human hepatocytes result in an irregular chimeric liver physiology (Tateno et al., 2015), significant antiviral efficacy can be observed in this model.

Approximately 8 weeks after the initial infection of the mice with HBV Genotype C, plasma are collected for each mouse to serve as a baseline HBsAg measurement. Then, cohorts of 9 mice each (n=3 for PK, n=6 for PD) received 3 weekly SC injections of 0 (PBS) or 3 mg/kg HBV(s)-219P1. The first day of dosing is considered Day 0. Non-terminal blood collections were performed weekly to determine the serum HBsAg and circulating HBV DNA levels in each mouse (FIGS. 14A-14D). Mice were euthanized for terminal tissue endpoints on Day 28. Day 28 liver samples were analyzed for intrahepatic HBV DNA and cccDNA levels. Significant antiviral activity was observed in all endpoints that were analyzed for mice treated with HBV(s)-219P1, including >80% reduction of HBsAg, as well as significant decreases in circulating HBV DNA, intrahepatic HBV DNA, and cccDNA (FIGS. 14A-14D). These data demonstrate that HBV(s)-219 treatment results in antiviral activity in infected human hepatocytes after systemic administration.

Example 5: HBV(s)-219P2 Potentiates the Antiviral Activity of Entecavir

The current standard of care, nucleo(s)tide analogs (e.g., Entecavir) are effective at reducing circulating HBV genomic DNA, but do not reduce circulating HBsAg. While this results in controlled viremia while on such treatment, lifelong treatment is required and a functional cure is rarely achieved. The RNAi oligonucletoides targeting the S antigen impact both the viral polymerase and HBsAg protein. In this study, the combinational effects of HBV(s)-219P2 as a monotherapy and combinational treatment with entecavir was explored in an HBV-expressing mouse (HDI model) for antiviral activity.

Mice were administered daily oral dosing of 500 ng/kg Entecavir (ETV) for 14 days. A single subcutaneous administration of HBV(s)-219P2 took place. Circulating viral load (HBV DNA) was measured by qPCR (FIG. 15A), plasma HBsAg level was measured by ELISA (FIG. 15B), and liver HBV mRNA and pgRNA levels were measured by qPCR. Clear additive effects were observed with combination therapy with HBV(s)-219P2 and ETV. The results show that ETV therapy alone shows no efficacy against circulating HBsAg or liver viral RNAs. Further, the antiviral activity of HBV(s)-219P2 as measured by HBsAg or HBV RNA is not impacted by codosing of ETV (FIGS. 15B-15C).

Figure 15A:
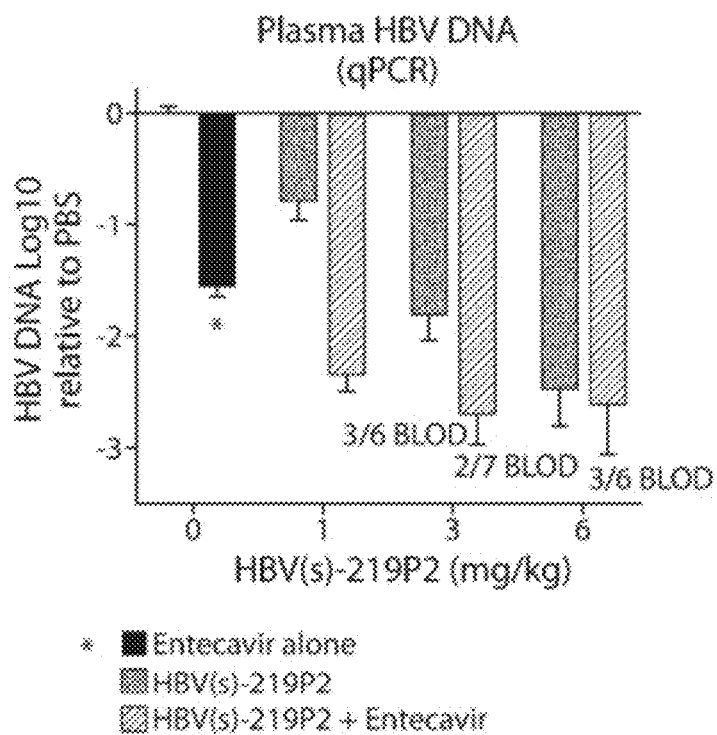
FIGS. 15A-15C show that HBV(s)-219 precursor 2 (HBV(s)-219P2) potentiates the antiviral activity of entecavir. In a HBV mouse hydrodynamic injection (HDI) model, a single dose of HBV(s)-219P2 was administered to mice subcutaneously on Day 1 followed by daily oral dosing of 500 ng/kg Entecavir (ETV) for 14 days. Circulating viral load (HBV DNA) was measured by qPCR (FIG. 15A). Plasma HBsAg leval was measured by ELISA (FIG. 15B). Liver HBV mRNA and pgRNA levels were measured by qPCR (FIG. 15C). The results show clear addive effects with combination therapy. ETV therapy alone shows no efficacy against circulating HBsAg or liver viral RNAs. The antiviral activity of HBV(s)-219P2 as measured by HBsAb or HBV RNA is not impacted by codosing of ETV. "BLOD" means "below limit of detection."
Figure 15B:
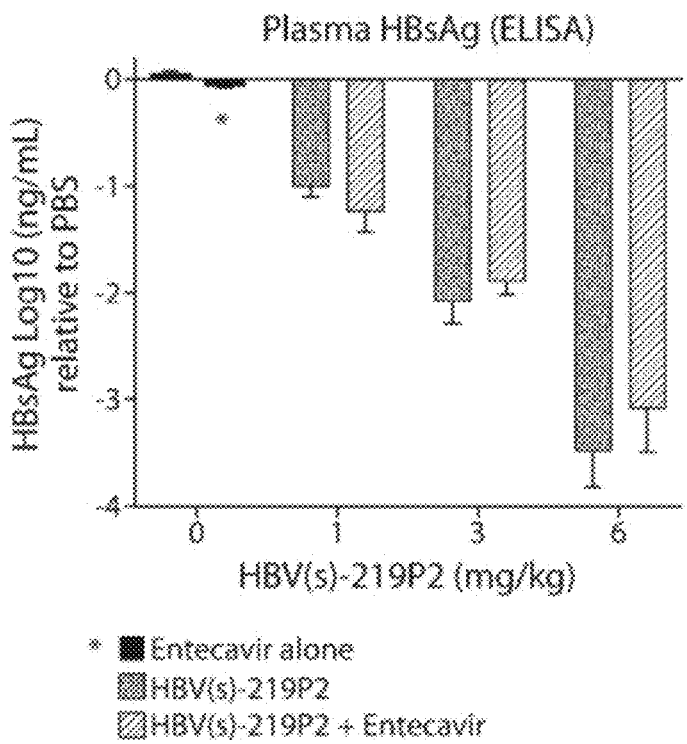
Figure 15C:
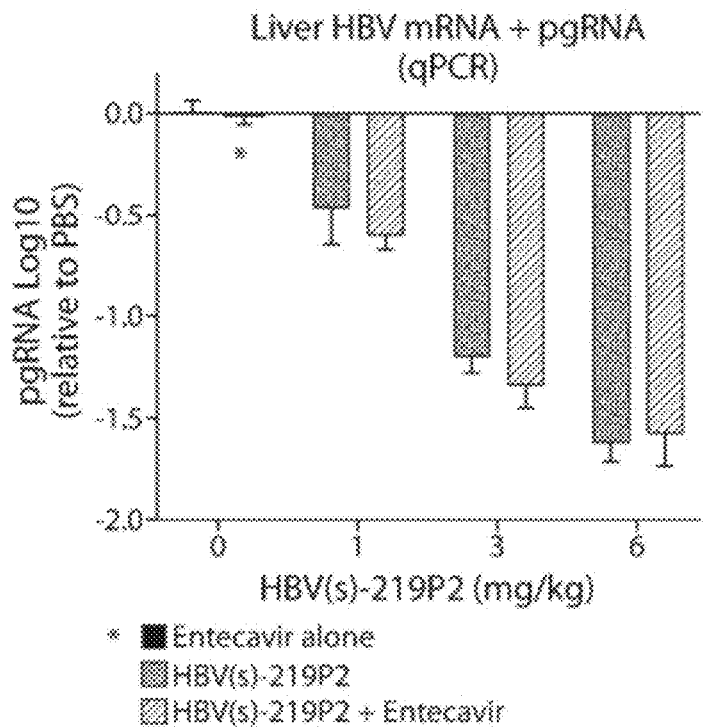

As shown in FIGS. 15A-15C, monotherapy of entecavir dosed 500 ng/kg PO daily for 14 days resulted in a mean ~1.6 log decrease in HBV DNA detected in plasma relative to PBS treated mice (n=6). No significant decrease in either circulating HBsAg, or hepatic viral RNAs was observed. Monotherapy of a single 1 mg/kg, or 3 mg/kg SC dose of HBV(s)-219P2 at day 0 resulted in a mean ~0.8 log, or ~1.8 log decrease in HBV DNA detected in plasma relative to PBS respectively (n=7). Monotherapy of a single 6 mg/kg SC dose of HBV(s)-219P2 at day 0 resulted in a mean ~2.5 log decrease in HBV DNA in plasma as well the levels in two mice falling below limit of detection (n=7). Monotherapy of a single SC dose of HBV(s)-219P2 on day 0 resulted in dose dependent decreases in in both circulating HBsAg, as well as hepatic viral RNAs. Combination therapy of entecavir dosed 500 ng/kg PO daily for 14 days and a single 1 mg/kg SC dose of HBV(s)-219P2 on day 0 resulted in additive reduction in HBV DNA detected in the plasma by a mean of ~2.3 log. Similar reductions in levels of plasma HBsAg and hepatic viral transcripts as observed with a monotherapy of a single 1 mg/kg SC dose of HBV(s)-219P2 indicating additivity in reducing plasma HBV DNA, but not circulating HBsAg, or hepatic viral transcript.

Example 6. Comparison of the Antiviral Activity of HBV(s)-219P2 and GalXC-HBVX

Figure 16A:
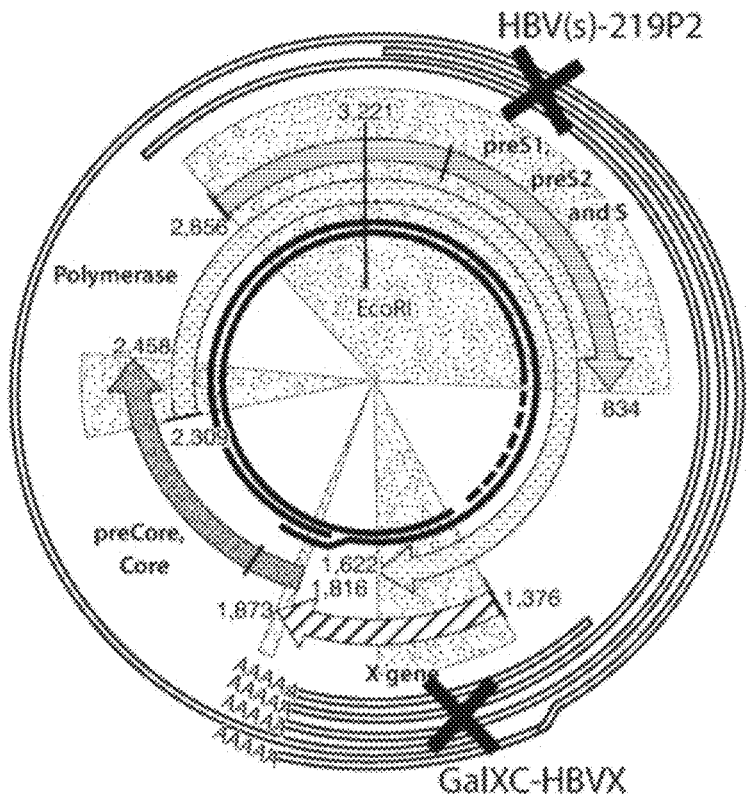
FIGS. 16A-16B show a comparison of HBsAg suppression activity of GalNac conjugated oligonucleotide targeting the S antigen (HBV(s)-219P2) or the X antigen (designated GalXC-HBVX). The result shows that HBVS-219P2 suppresses HBsAg for a longer duration than GalXC-HBVX or an equimolar combination of both RNAi Agents.
Figure 16B:
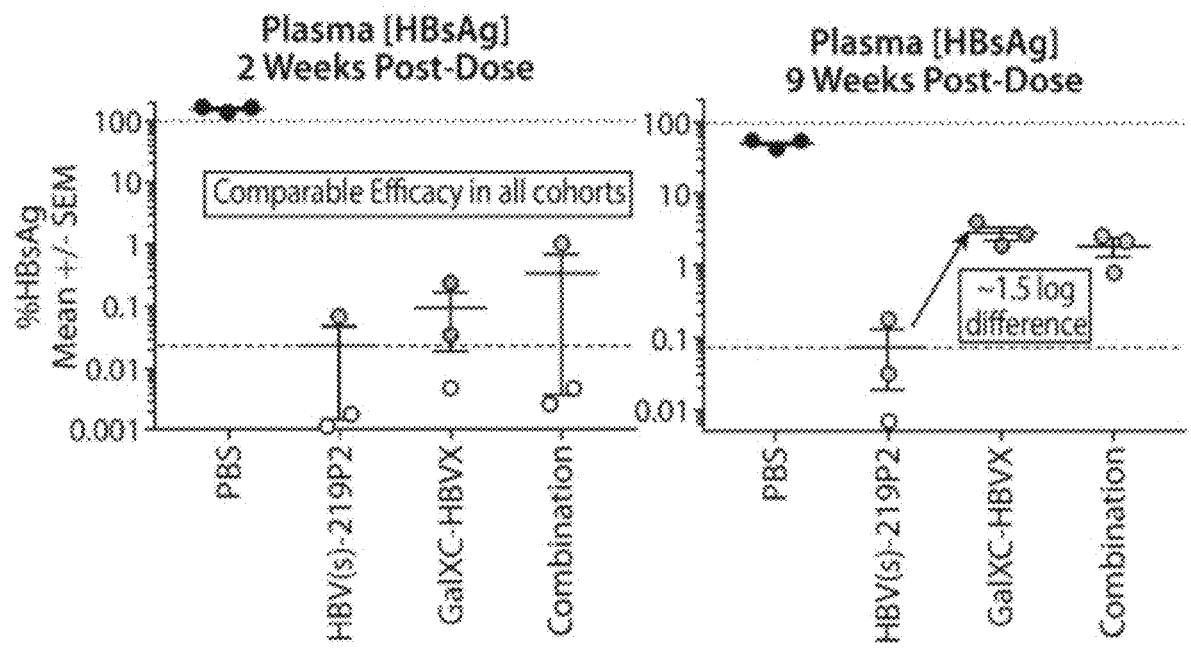

In this study, HBV-expressing mice (HDI model) were administered HBV(s)-219P2, GalXC-HBVX (same sequence as the GalXC-HBVX used in FIGS. 12A and 12B), or a combination of the two RNAi oligonucleotides and plasma HBsAg level two weeks or nine weeks post dose were monitored. As shown in FIG. 16B, similar levels of HBsAg suppression were observed 2 weeks after treatment with a single saturating 9 mg/kg SC dose of either HBV(s)-219P2, GalXC-HBVX, or a combination of both. Prolonged suppression of HBsAg was observed in mice treated with the S-targeting HBV(s)-219P2 treatment, whereas mice treated with the GalXC-HBVX, or a combination of both, had significant recovery of HBsAg 9 weeks after treatment (n=3).

Figure 17A:
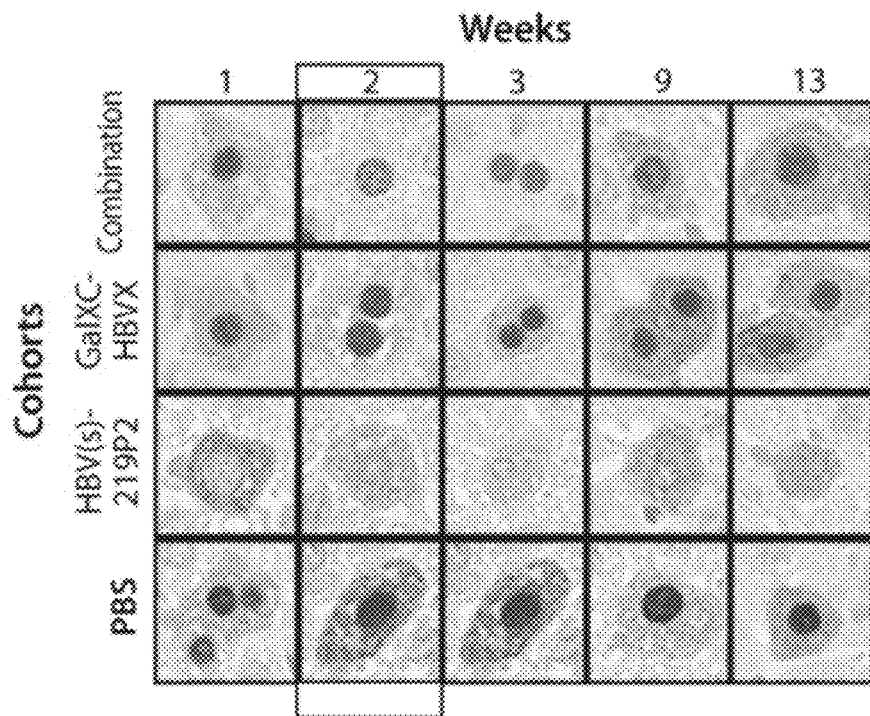
FIGS. 17A-17C show the subcellular location of HBV core antigen (HBcAg) in HBV-expressing mice treated with HBV(s)-219P2, GalXC-HBVX or a 1:1 combination.
Figure 17B:
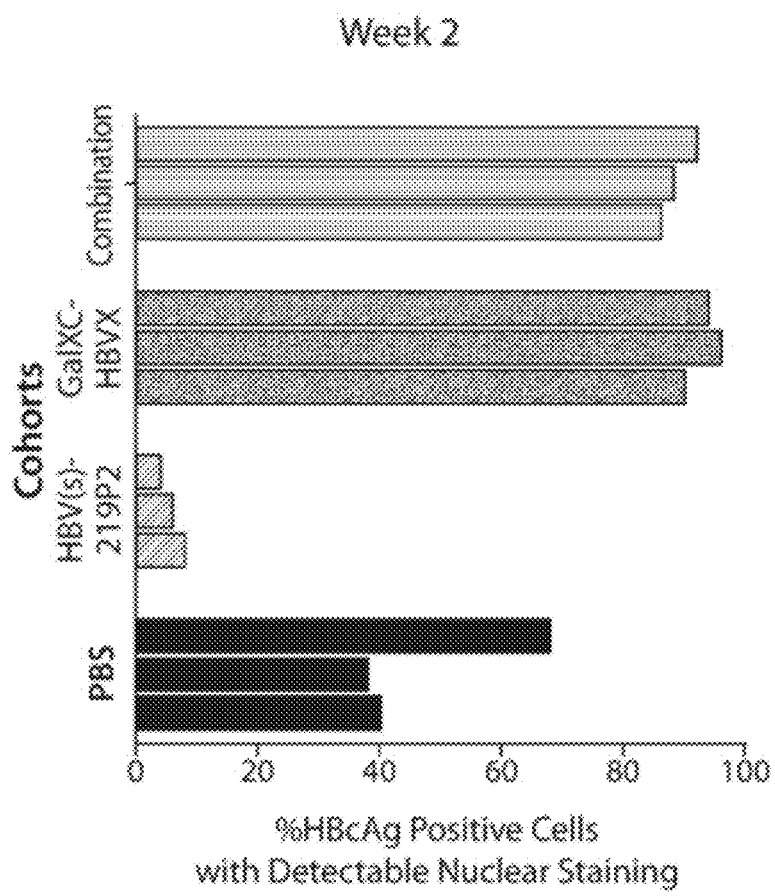
Figure 17C:
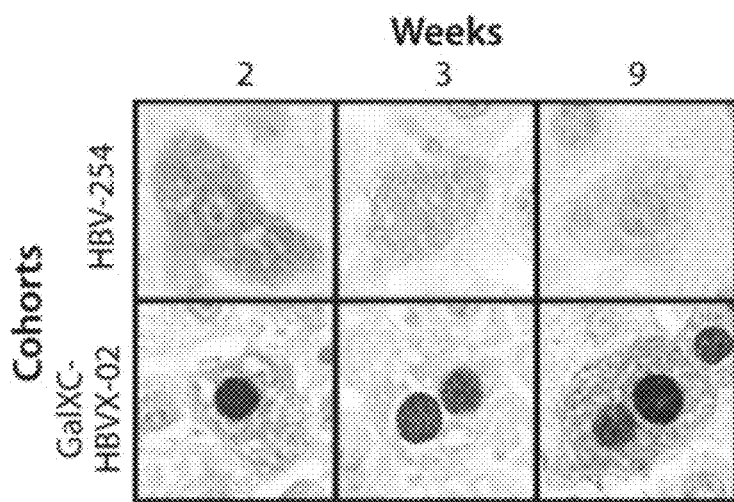

The subcellular localization of HBV Core Antigen (HBcAg) in HBV-expressing mice was also evaluated in mice receiving HBV(s)-219P2, GalXC-HBVX, or a combination of the two RNAi oligonucleotides. HBV-expressing mice (HDI model) were treated with a single saturating dose (9 mg/kg, s.c.) of HBV(s)-219P2, GalXC-HBVX or a 1:1 combination. At the time points indicated in FIG. 17A, liver sections were stained for HBcAg; representative hepatocytes are shown. Cohorts treated with HBV(s)-219P2, either as a monotherapy or in combination with GalXC-HBVX, feature nuclear HBcAg. Cohorts treated with only GalXC-HBVS show only cytosolic localization of HBcAg, reported as a favorable prognostic indicator of treatment response (Huang et al. J. Cell. Mol. Med. 2018). The percentage of HBcAg-positive-cells with nuclear staining in each animal is shown in FIG. 17B (n=3/group, 50 cells counted per animal, 2 weeks after dosing). To confirm that the effect on HBcAg subcellular localization is due to the region of the HBV transcriptome, and not to an unknown property of the RNAi sequence, alternative sequences were designed and tested, targeting within the X and S open reading frames (see FIG. 17C). HBV-254 was used in FIG. 17C. The sequence of HBV-254 is described in Example 1. The alternative oligonucleotide targeting HBxAg used in FIG. 17C has a sense strand sequence of GCACCUCUCUUUACGCG-GAAGCAGCCGAAAGGCUGC (SEQ ID NO: 41) and an antisense sequence of UUCCGCGUAAAGAGAG-GUGCGG (SEQ ID NO: 42). The two alternative RNAi oligonucleotides have different RNAi target sequences in the S or X antigen than the RNAi oligonucleotides used in FIG. 16B. However, they display the same differential effect on plasma level HBcAg, indicating that the effect is specific to targeting the S antigen per se, but not specific the oligonucleotide used.

Figure 19A:
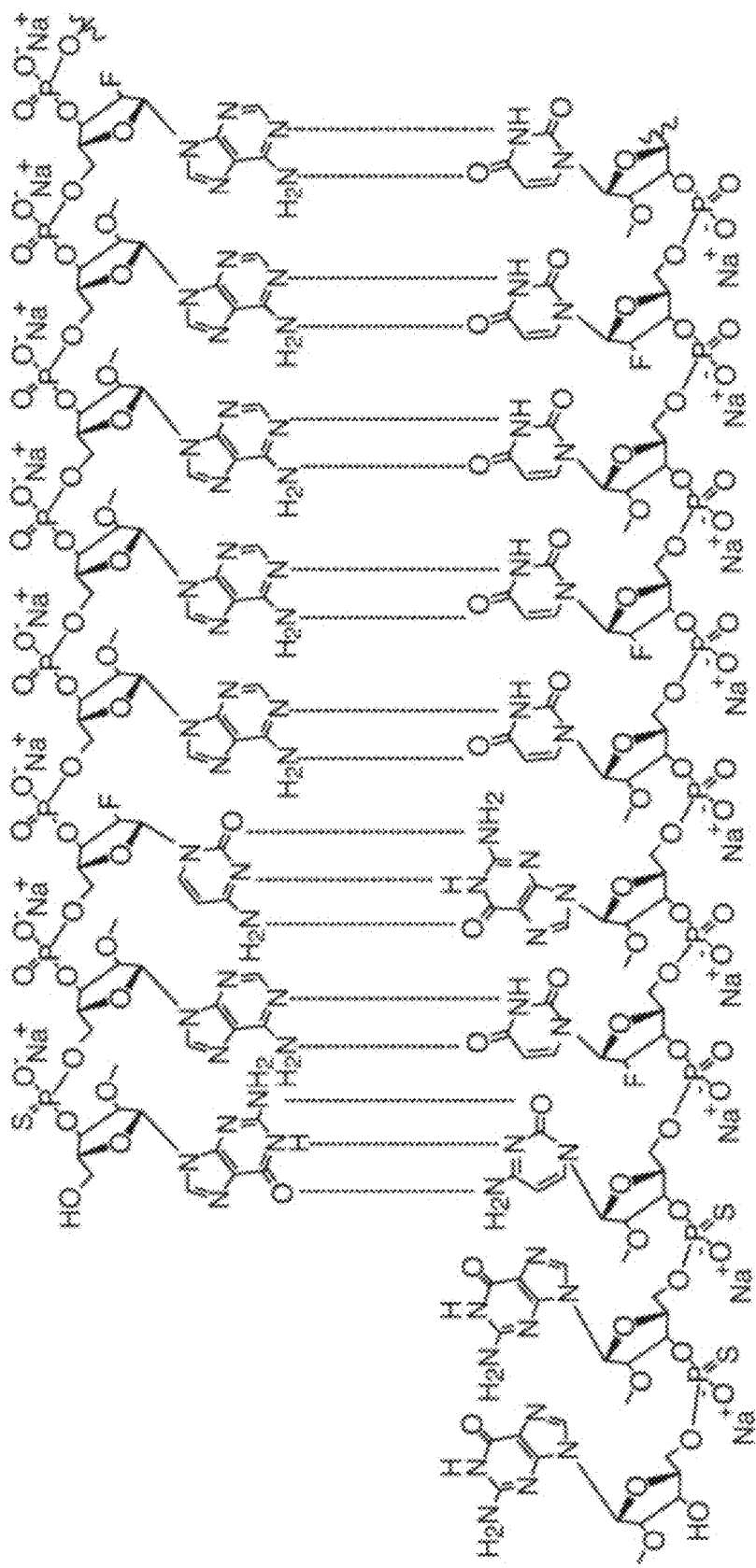
FIGS. 19A-19B shows the chemical structure of HBV(s)-219 and HBV(s)-219P2.
Figure 19B:
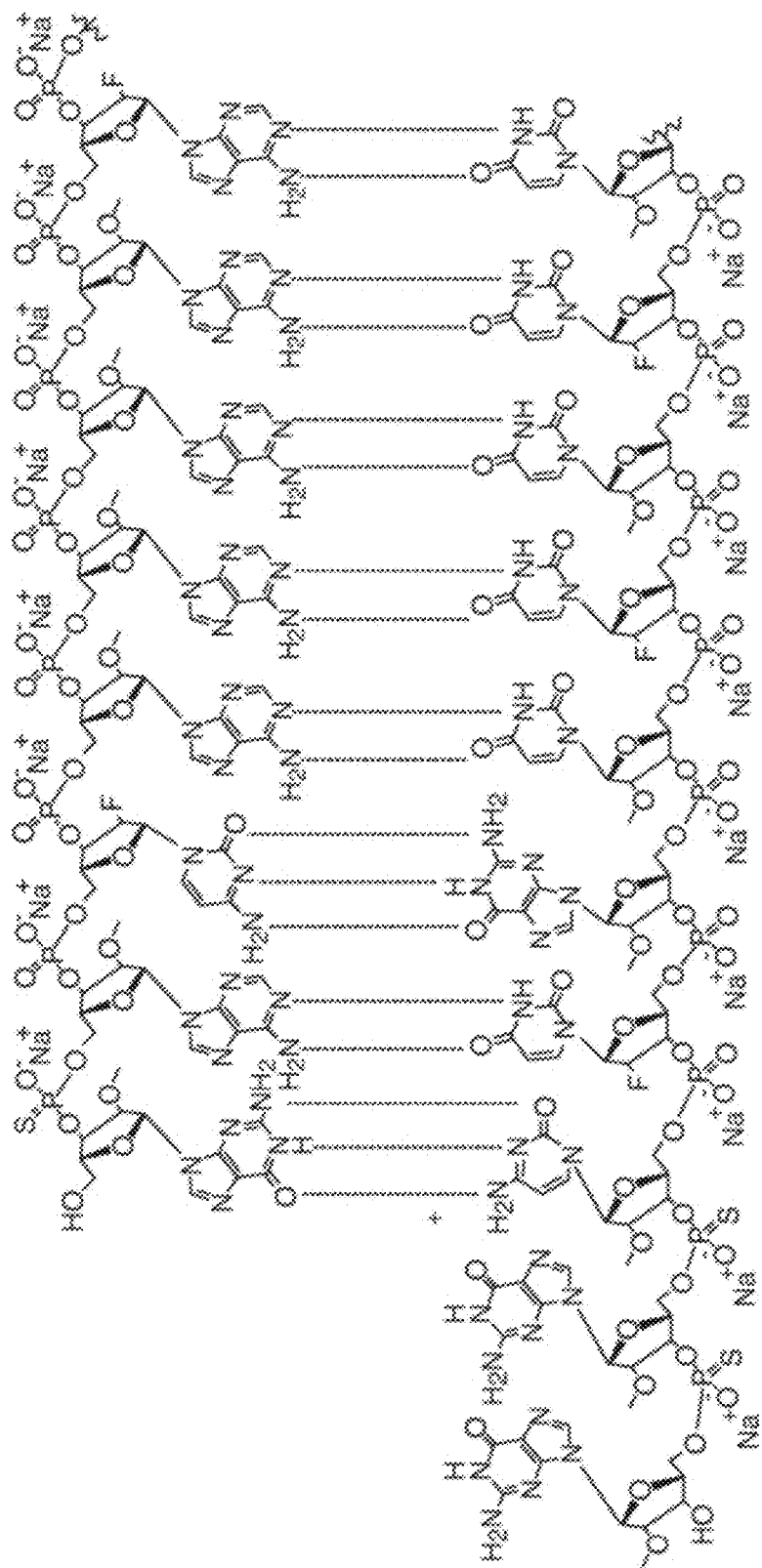

Example 7 Evaluation of the Safety, Tolerability in Healthy Human Subjects and Efficacy of HBV(s)-219 in HBV Patients This study is designed to evaluate the safety and tolerability in healthy subjects (Group A) and efficacy of HBV(s)-219 in HBV patients (Group B). The dose by cohort information is shown in FIG. 18. The molecular structure of HBV(s)-219 is shown in FIG. 10, FIG. 19A, and also illustrated below:

```
Sense Strand:
5' mG-S-mA-fC-mA-mA-mA-mA-fA-fU-fC-mC-fU-fC-mAmC-mA-fA-mU-mA-mA-mG-mC-mA-mG-mC-mC-[ademG-GalNAc]-

[ademA-GalNAc]-[ademA-GalNAc]-[ademA-GalNAc]-mG-mGmC-mU-mG-mC 3'
```

Hybridized to:

```
Antisense Strand:
5' [MePhosphonate-4O-mU]S-fU-S-fA-S-mU-fU-mG-fU-fGmA-fG-mG-fA-mU-fU-mU-fU-mU-mG-fU-mC-S-mG-S-mG 3'
```

Legend:
  mX: 2'-O-methyl ribonucleotide
  f X: 2'-fluoro-deoxyribonucleotide
  [ademA-GalNAc]: 2'-modified-GalNAc adenosine
  [adernG-GalNAc]: 2'-modified -GalNAc guanosine
  [MePhosphonate-4O-mU]:  4'-O-monomethylphosphonate-2'-O-methyl uridine
  Linkages: "-" denotes phosphodiester
  "-S-" denotes phosphorothioate
  The Patient selection criterial are shown below.
  Group A—Healthy Subjects
  Inclusion criteria:
  1. Age 18 (or age of legal consent, whichever is older) to 65 years inclusive, at the time of signing the informed consent.
  2. Overtly healthy at the time of screening as determined by medical evaluation including medical history, physical examination, and laboratory tests
    a. No symptoms of ongoing illness
    b. No clinically significant abnormalities in body temperature, pulse rate, respiratory rate, blood pressure
    c. No clinically significant cardiovascular or pulmonary disease, and no cardiovascular or pulmonary disease requiring pharmacologic medication.
  3. 12-lead electrocardiogram (ECG) within normal limits or with no clinically significant abnormalities at screening and Day −1 in the opinion of the Investigator
  4. Negative screen for alcohol or drugs of abuse at Screening Visit 1 and admission (Day −1)
  5. Non-smokers for at least 5 years preceding Screening Visit 1, with a negative urinary cotinine concentration at Screening Visit 1
  6. Body mass index (BMI) within the range 18.0-32.0 kg/m2 (inclusive).
  7. Male or Female:
    a. Male Participants:
    A male participant must agree to use contraception, during the treatment period and for at least two weeks after the dose of study intervention and refrain from donating sperm during this period.
    b. Female participants:
    A female participant is eligible to participate if she is not pregnant, not breastfeeding, and at least one of the following conditions applies: Not a woman of childbearing potential (WOCBP), OR, depending on region; a WOCBP who agrees to follow the contraceptive guidance, beginning at post-screen study enrollment continuing throughout the treatment period and for at least 12 weeks after the dose of study intervention.
  8. Capable of giving signed informed consent 1, which includes compliance with the requirements and restrictions.
  Exclusion Criteria, Group A
  1. History of any medical condition that may interfere with the absorption, distribution or elimination of study drug, or with the clinical and laboratory assessments in this study, including (but not limited to); chronic or recurrent renal disease, functional bowel disorders (e.g., frequent diarrhea or constipation), GI tract disease, pancreatitis, seizure disorder, mucocutaneous or musculoskeletal disorder, history of suicidal attempt(s) or suicidal ideation, or clinically significant depression or other neuropsychiatric disorder requiring pharmacologic intervention
  2. Poorly controlled or unstable hypertension; or sustained systolic BP >150 mmHg or diastolic BP >95 mmHg at Screen
  3. History of diabetes mellitus treated with insulin or hypoglycemic agents
  4. History of asthma requiring hospital admission within the preceding 12 months
  5. Evidence of G-6-PD deficiency as determined by the Screen result at the central study laboratory
  6. Currently poorly controlled endocrine conditions, with the exception of thyroid conditions (hyper/hypothyroidism, etc.) where any pharmacologically treated thyroid conditions are excluded
  7. A history of malignancy is allowed if the participant's malignancy has been in complete remission off chemotherapy and without additional medical or surgical interventions during the preceding three years
  8. History of multiple drug allergies or history of allergic reaction to an oligonucleotide or GalNAc
  9. History of intolerance to SC injection(s) or significant abdominal scarring that could potentially hinder study intervention administration or evaluation of local tolerability
  10. Clinically relevant surgical history
  11. History of persistent ethanol abuse (>40 gm ethanol/day) or illicit drug use within the preceding 3 years.
  12. Clinically significant illness within the 7 days prior to the administration of study intervention
  13. Donation of more than 500 mL of blood within the 2 months prior to administration of study intervention or plasma donation within 7 days prior to Screen
  14. Significant infection or known inflammatory process ongoing at Screening (in the opinion of the Investigator)
  15. History of chronic or recurrent urinary tract infection (UTI), or UTI within one month prior to Screen
  16. Scheduled for an elective surgical procedure during the conduct of this study
  17. Use of prescription medications within 4 weeks prior to the administration of study intervention
  18. Use of over-the-counter (OTC) medication or herbal supplements, excluding routine vitamins, within 7 days of first dosing, unless agreed as not clinically relevant by the Investigator and Sponsor.
  19. Has received an investigational agent within the 3 months prior to dosing or is in followup of another clinical study prior to study enrollment.
  20. Seropositive for HBV, HIV, HCV, or HDV antibody at Screening (historical testing may be used if performed within the 3 months prior to screening)
  21. Alanine aminotransferase (ALT), aspartate aminotransferase (AST), gamma-glutamyl transferase (GGT), total bilirubin, alkaline phosphatase (ALP), or albumin outside of the reference range at the Screening Visit or on admission (Day −1)

22. Complete blood count test abnormalities that are considered clinically relevant and unacceptable by the Investigator; hemoglobin <12.0 g/dL (equivalent to 120 g/L); platelets outside of the normal range.

23. Hemoglobin A1C (HbAlC) >7%

24. Any other safety laboratory test result considered clinically significant and unacceptable by the Investigator 25. Has undertaken, or plans to undertake, a significant change in exercise levels from 48 hours prior to entrance into the clinical research center until the end of study.

26. Any condition that, in the opinion of the Investigator, would make the participant unsuitable for enrollment or could interfere with participation in or completion of the study.

Group B Adults with Hepatitis B
Inclusion Criteria, Group B

1. Age 18 (or age of legal consent, whichever is older) to 65 years inclusive, at the time of signing the informed consent.

2. Chronic hepatitis B infection, documented by:
  a. clinical history compatible with CHB, based on compatible clinical information, and previous seropositivity for HBsAg and potentially other HBV serologic markers (HBeAg, HBV DNA)
  b. Serum HBsAg >1000 IU/mL at Screening for HBeAg-positive patients, or >500 IU/mL for HBeAg-negative patients
  c. Serum HBV DNA>20,000 IU/mL at Screening for treatment-naïve patients, as determined by the TaqMan™ HBV DNA v2.0 assay at the central study laboratory
  d. Serum IgM anti-HBc negative 3. Clinical history compatible with compensated liver disease, with no evidence of cirrhosis:
  a. No history of bleeding from esophageal or gastrointestinal varices
  b. No history of ascites
  c. No history of jaundice attributed to chronic liver disease
  d. No history of hepatic encephalopathy
  e. No physical stigmata of portal hypertension—spider angiomata, etc.
  f. No previous liver biopsy, hepatic imaging study, or elastography result indicating cirrhosis 4. Treatment-naïve for hepatitis B: no previous antiviral therapy for hepatitis B (no previous HBV nucleos[t]ide or interferon-containing treatment) OR continuously on nucleos(t)ide therapy (entecavir or tenofovir) for at least 12 weeks prior to the Screening visit, with satisfactory tolerance and compliance 5. Serum ALT >60 U/L (males) or >38 U/L (females) (2×ULN by American Association for the Study of Liver Diseases (AASLD) HBV guidance criteria, Terrault et al., 2016)

6. 12-lead ECG with no clinically significant abnormalities at Screening and Day −1 (in the opinion of the Investigator)

7. No other known cause of liver disease

8. No other medical condition that requires persistent medical management or chronic or recurrent pharmacologic intervention, other than well-controlled hypertension and statin management of hypercholesterolemia 9. BMI within the range 18.0-32.0 kg/m2 (inclusive)

10. Male or female
  a. Male Participants:
  A male participant must agree to use contraception during the treatment period and for at 12 weeks after the last dose of study intervention and refrain from donating sperm during this period.
  b. Female Participants:
  A female participant is eligible to participate if she is not pregnant, not breastfeeding, and at least one of the following conditions applies: Not a WOCBP OR, depending on region A WOCBP who agrees to follow the contraceptive guidance during the treatment period and for at least 12 weeks after the dose of study intervention.

11. Capable of giving signed informed consent, which includes compliance with the requirements and restrictions.

Exclusion Criterial, Group B

1. History of any medical condition that may interfere with the absorption, distribution or elimination of study drug, or with the clinical and laboratory assessments in this study, including (but not limited to); chronic or recurrent renal disease, functional bowel disorders (e.g., frequent diarrhea or constipation), GI tract disease, pancreatitis, seizure disorder, mucocutaneous or musculoskeletal disorder, history of suicidal attempt(s) or suicidal ideation, or clinically significant depression or other neuropsychiatric disorder requiring pharmacologic intervention 2. Poorly controlled or unstable hypertension 3. History of diabetes mellitus treated with insulin or hypoglycemic agents 4. History of asthma requiring hospital admission within the preceding 12 months 5. Evidence of G-6-PD deficiency as determined by the Screen result at the central study laboratory 6. Currently poorly controlled endocrine conditions, with the exception of thyroid conditions (e.g. hyper/hypothyroidism, etc.) where any pharmacologically treated thyroid conditions are excluded 7. History of chronic or recurrent UTI, or UTI within one month prior to Screen 8. History of HCC 9. History of malignancy other than HCC is allowable if the patient's malignancy has been in complete remission off chemotherapy and without additional medical or surgical interventions during the preceding three years 10. History of persistent ethanol abuse (>40 gm ethanol/day) or illicit drug use within the preceding 3 years.

11. History of intolerance to SC injection(s) or significant abdominal scarring that could potentially hinder study intervention administration or evaluation of local tolerability.

12. Receipt of a transfusion in the last 6 weeks prior to therapy or anticipated transfusions through the post-trial follow-up.

13. Donated or lost >500 mL of blood within 2 months prior to Screening, or plasma donation within 7 days prior to Screening 14. Antiviral therapy (other than entecavir or tenofovir) within 3 months of Screening or treatment with interferon in the last 3 years 15. Use within the last 6 months of (or an anticipated requirement for) anticoagulants, systemically administered corticosteroids, systemically administered immunomodulators, or systemically administered immunosuppressants 16. Use of prescription medication within 14 days prior to administration of study intervention that, in the opinion of the PI or the Sponsor, would interfere with study conduct. Topical products without systemic absorption, statins (except rosuvastatin), hypertensive medications, OTC and prescription pain medication or hormonal contraceptives (females) are acceptable.

17. Depot injection or implant of any drug within 3 months prior to administration of study intervention, with the exception of injectable/implantable birth control.

18. Persistent use of herbal supplements or systemic over-the-counter medications; participants must be willing to stop for the duration of the study period 19. Has received an investigational agent within the 3 months prior to dosing or is in followup of another clinical study prior to study enrollment.

20. Liver Elastography (i.e. FibroScan®) kPa >10.5 at Screening

21. Systolic blood pressure >150 mmHg and a diastolic blood pressure of >95 mmHg after 10 minutes supine rest, at Screening.

22. Hepatic transaminases (ALT or AST) confirmed >7×ULN at Screening

23. History of persistent or recurrent hyperbilirubinemia, unless known Gilbert's Disease or Dubin-Johnson Syndrome 24. Seropositive for antibodies to human immunodeficiency virus (HIV) or hepatitis C virus (HCV) or hepatitis delta virus (HDV)

25. Hgb <12 g/dL (males) or <11 g/dL (females)

26. Serum albumin <3.5 g/dL at screening.

27. Total WBC count <4,000 cells/pt or absolute neutrophil count (ANC) <1800 cells/μL at screening.

28. Platelet count ≤100,000 per μL at screening.

29. International normalized ratio (INR) or prothrombin time (PT) above the upper limit of the normal reference range (as per the local laboratory reference range) at screening.

30. Serum BUN or creatinine >ULN

31. Serum amylase or lipase >1.25×ULN

32. Serum HbA1c >7.0%

33. Serum alpha fetoprotein (AFP) value >100 ng/mL. If AFP at screening is >ULN but <100 ng/mL, patient is eligible if a hepatic imaging study reveals no lesions suspicious of possible HCC 34. Any other safety laboratory test result considered clinically significant and unacceptable by the Investigator 35. Has undertaken, or plans to undertake, a significant change in exercise levels from 48 hours prior to entrance into the clinical research center until the end of study.

36. Any condition that, in the opinion of the Investigator, would make the participant unsuitable for enrollment or could interfere with participation in or completion of the study.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide comprising a sense strand forming a duplex region with an antisense strand, wherein:
the sense strand consists of a sequence as set forth in GACAAAAAUCCUCACAAUAAGCAGCCGAAAGGCUGC (SEQ ID NO: 9) and comprising
2'-fluoro modified nucleotides at positions 3, 8-10, 12, 13, and 17;
2'-O-methyl modified nucleotides at positions 1, 2, 4-7, 11, 14-16, 18-26, and 31-36; and
a phosphorothioate linkage between the nucleotides at positions 1 and 2,
wherein each of the nucleotides of the -GAAA- sequence on the sense strand is conjugated to a monovalent GalNac moiety; and
the antisense strand consists of a sequence as set forth in UUAUUGUGAGGAUUUUUGUCGG (SEQ ID NO: 6) and comprising
2'-fluoro modified nucleotides at positions 2, 3, 5, 7, 8, 10, 12, 14, 16, and 19;
2'-O-methyl modified nucleotides at positions 1, 4, 6, 9, 11, 13, 15, 17, 18, and 20-22; and
phosphorothioate linkages between nucleotides at positions 1 and 2, between nucleotides at positions 2 and 3, between nucleotides at positions 3 and 4, between nucleotides at positions 20 and 21, and between nucleotides at positions 21 and 22,
wherein the 4'-carbon of the sugar of the 5'-nucleotide of the antisense strand comprises a methoxy phosphonate (MOP).

2. The oligonucleotide of claim 1, wherein the 5'-nucleotide of the antisense strand has the following structure:

3. The oligonucleotide of claim 1, wherein the -GAAA- sequence comprises the structure:

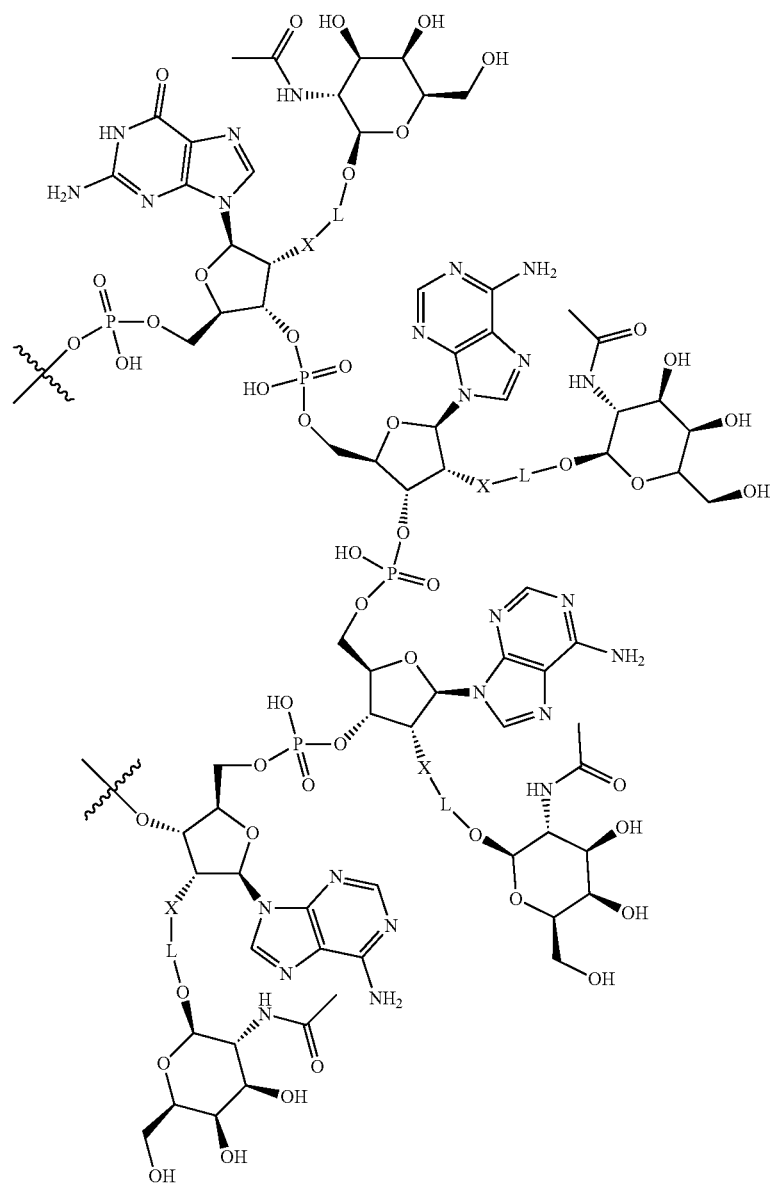

wherein:

L represents a bond, click chemistry handle, or a linker of 1 to 20, inclusive, consecutive, covalently bonded atoms in length, selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, and combinations thereof; and X is O, S, or N.

4. The oligonucleotide of claim 3, wherein L is an acetal linker.

5. The oligonucleotide of claim 3, wherein X is O.

6. The oligonucleotide of claim 3, wherein the -GAAA- sequence comprises the structure:
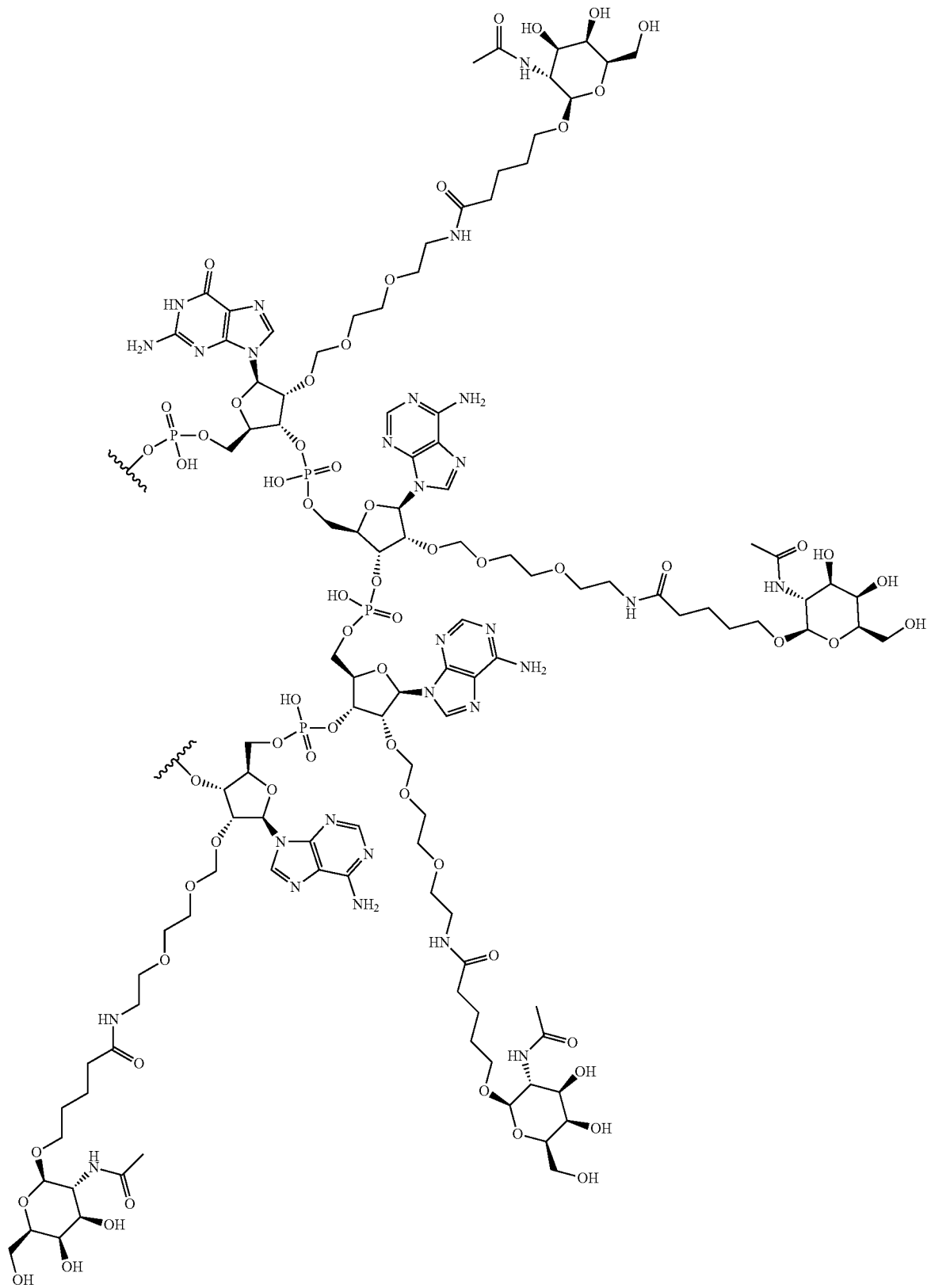 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(=O)(O)O*]

7. An oligonucleotide comprising a sense strand forming a duplex region with an antisense strand, and counterions, wherein:

the sense strand consists of a sequence as set forth in GACAAAAAUCCU-CACAAUAAGCAGCCGAAAGGCUGC (SEQ ID NO: 9) and comprising 2'-fluoro modified nucleotides at positions 3, 8-10, 12, 13, and 17;

2'-O-methyl modified nucleotides at positions 1, 2, 4-7, 11, 14-16, 18-26, and 31-36; and one phosphorothioate internucleotide linkage between the nucleotides at positions 1 and 2, wherein each of the nucleotides of the -GAAA- sequence on the sense strand is conjugated to a monovalent GalNac moiety, wherein the -GAAA- sequence comprises the structure:

and the antisense strand consists of a sequence as set forth in UUAUUGUGAGGAUUUUUGUCGG (SEQ ID NO: 6) and comprising 2'-fluoro modified nucleotides at positions 2, 3, 5, 7, 8, 10, 12, 14, 16, and 19;

2'-O-methyl modified nucleotides at positions 1, 4, 6, 9, 11, 13, 15, 17, 18, and 20-22; and five phosphorothioate internucleotide linkages between nucleotides at positions 1 and 2, between nucleotides at positions 2 and 3, between nucleotides at positions 3 and 4, between nucleotides at positions 20 and 21, and between nucleotides at positions 21 and 22, wherein the 5'-nucleotide of the antisense strand has the following structure:

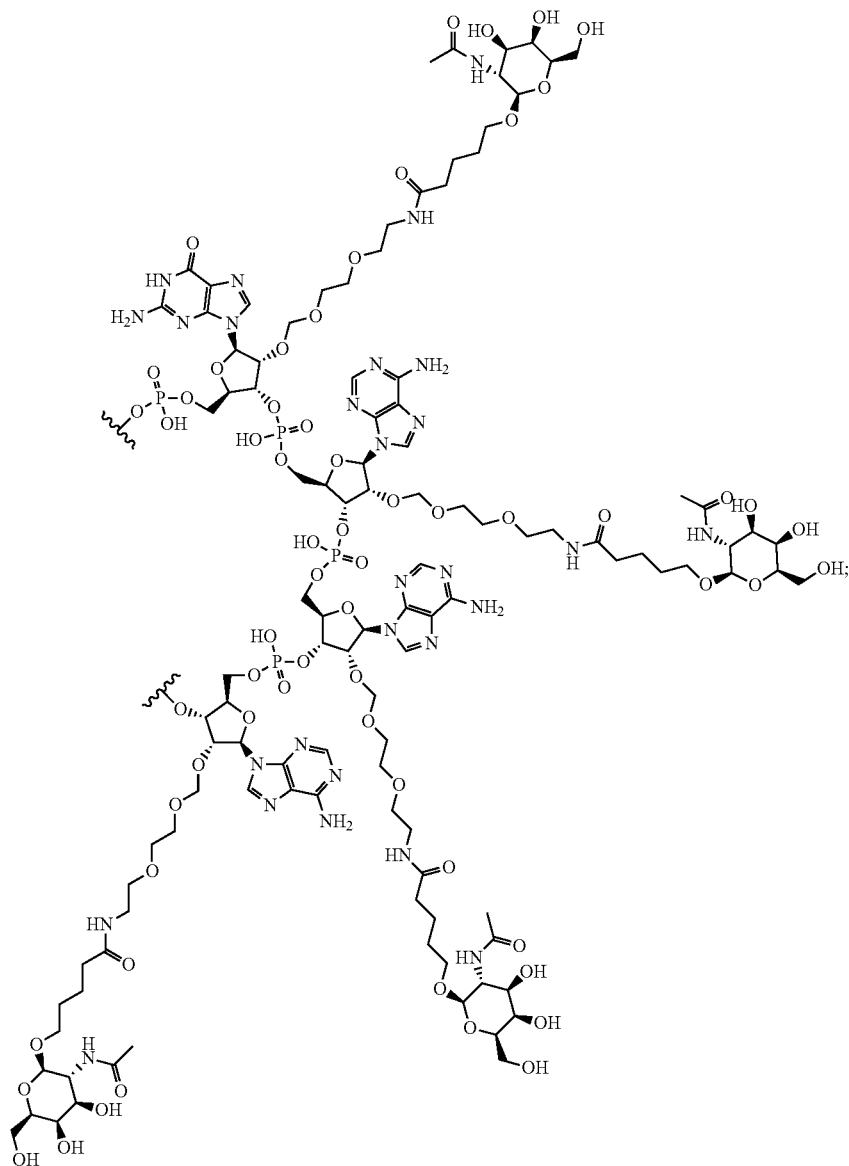 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(=O)(O)O*]

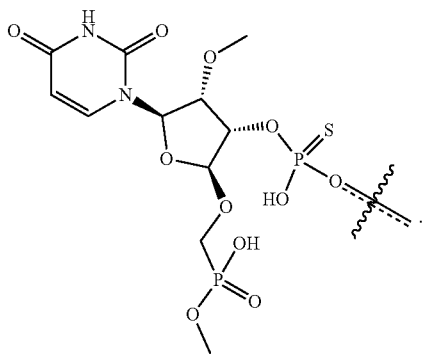

8. A composition comprising the oligonucleotide of claim 1, and a pharmaceutically acceptable carrier.

9. A composition comprising the oligonucleotide of claim 7, and a pharmaceutically acceptable carrier.

10. The composition of claim 8, further comprising a counterion.

11. The composition of claim 9, wherein the counterions comprise Na+ counterions.

12. The composition of claim 8, wherein the pharmaceutically acceptable carrier is a phosphate-buffered saline solution.

13. The composition of claim 9, wherein the pharmaceutically acceptable carrier is a phosphate-buffered saline solution.

14. An in vitro method of reducing expression of hepatitis B virus (HBV) surface antigen (HBsAg) in a cell, the method comprising delivering to the cell an oligonucleotide of claim 1.

15. The method of claim 14, wherein the cell is a hepatocyte.

16. An in vitro method of reducing expression of hepatitis B virus (HBV) surface antigen (HBsAg) in a cell, the method comprising delivering to the cell an oligonucleotide of claim 7.

17. The method of claim 16, wherein the cell is a hepatocyte.

18. A method of treating HBV infection in a subject, comprising administering to the subject the composition of claim 8.

19. The method of claim 18, wherein the composition is administered subcutaneously to the subject.

20. The method of claim 18, wherein the composition is administered intravenously to the subject.

21. The method of claim 18, wherein the pharmaceutically acceptable carrier in the composition is a solvent or dispersion medium comprising water.

22. A method of treating HBV infection in a subject, comprising administering to the subject the composition of claim 9.

23. The method of claim 22, wherein the composition is administered subcutaneously to the subject.

24. The method of claim 22, wherein the composition is administered intravenously to the subject.

25. The method of claim 22, wherein the pharmaceutically acceptable carrier in the composition is a solvent or dispersion medium comprising water.

26. A method of treating HBV infection in a subject, comprising administering to the subject the oligonucleotide of claim 7.

27. The method of claim 26, wherein the oligonucleotide is administered intravenously or subcutaneously to the subject.

* * * * *